US008158853B2

(12) United States Patent
Lepelley et al.

(10) Patent No.: US 8,158,853 B2
(45) Date of Patent: Apr. 17, 2012

(54) POLYNUCLEOTIDES ENCODING LIGNIN BIOSYNTHETIC PATHWAY ENZYMES IN COFFEE

(75) Inventors: Maud Lepelley, Tours (FR); James Gérard McCarthy, Nolzay (FR); Vincent Petiard, Tours (FR); Gerald Cheminade, Tours (FR); Steven D. Tanksley, Dryden, NY (US); Chenwei Lin, Aubumdale, MA (US)

(73) Assignees: Nestec S. A., Vevey (CH); Cornell University, Ithaca, NY (US)

( * ) Notice: Subject to any disclaimer, the term of this patent is extended or adjusted under 35 U.S.C. 154(b) by 688 days.

(21) Appl. No.: 12/083,432

(22) PCT Filed: Oct. 16, 2006

(86) PCT No.: PCT/US2006/040223
§ 371 (c)(1),
(2), (4) Date: Feb. 27, 2009

(87) PCT Pub. No.: WO2007/047518
PCT Pub. Date: Apr. 26, 2007

(65) Prior Publication Data
US 2009/0313728 A1 Dec. 17, 2009

Related U.S. Application Data

(60) Provisional application No. 60/726,812, filed on Oct. 14, 2005.

(51) Int. Cl.
*C12N 15/82* (2006.01)
*C12N 15/10* (2006.01)
*C12N 15/00* (2006.01)
*C07H 21/04* (2006.01)
*A01H 5/00* (2006.01)

(52) U.S. Cl. ........ 800/284; 800/278; 800/295; 800/287; 435/320.1; 435/468; 536/23.1; 536/23.6

(58) Field of Classification Search .................. None
See application file for complete search history.

(56) References Cited

U.S. PATENT DOCUMENTS 5,959,178 A * 9/1999 Fritig et al. .................. 800/298
6,252,135 B1 * 6/2001 Chiang et al. ................ 800/278

FOREIGN PATENT DOCUMENTS

| WO | WO 98/03535 A | 1/1998 |
| WO | WO 01/34817 A2 | 5/2001 |
| WO | WO 02/10210 A | 2/2002 |
| WO | WO 03/046163 A2 | 6/2003 |
| WO | WO 2006/036741 A | 4/2006 |

OTHER PUBLICATIONS

Campa et al 2001, December UniProt:Q8LL87.*
Campa et al 2001 GenBank Accession Q8LL87, submitted Dec. 2001, provided in alignment in text of office action.*
Database UniProt [Online], Mar. 1, 2002, "Caffeic Acid 3-0 methyltransferase (EC 2.1.1.68) (S-adenosys 1-L-methionine: caffeic acid 3-0-methyltransferase) (COMT) (CAOMT)," XP002431178, retrieved from EBI accession No. UniProt:Q8W013, Database accession No. Q8W013. The sequence has 85.9% identity with SEQ ID No. 15.
Database UniProt [Online], Nov. 1, 1999, "Caffeic acid 3-0-methyltransferase 1 (EC 2.1.1.68) (S-adenosys 1-L-methionine: caffeic acid 3-0-methyltransferase) (COMT-1) (CAOMT-1)," XP002431179 retrieved from EBI accession No. UniProt:Q9XGW0, Database accession No. Q9XGWO. The sequence has 85.9% identity with SEQ ID No. 15.
Database UniProt [Online] Jan. 1, 1998, "Putative cinnamoyl-CoA Reductase." XP002446800 retrieved from EBI accession No. UniProt:022809, Database accession No. 022809. The sequence has 65.8% identity with SEQ ID No. 19.
Database Geneseq [Online] Jun. 22, 2001, "Fibronectin fragment and fibrin related peptide SEQ ID No. 1166." XP002446801 retrieved from EBI accession No. GSP:AAB91990. The sequence has 65.8% identity with SEQ ID No: 19.
Database UniProt [Online] Sep. 13, 2004, Putative cinnamoyl-CoA Reductase (Os06g0623600 protein). XP002446802 retrieved from EBI accession No. UniProt:Q69UO2. The sequence has 58.7% identity with SEQ ID No. 19.
Database UniProt [Online] Jul. 5, 2004 "Cytochrome P450." XP002446803 retrieved from EBI accession No. UniProt:Q75W19. Database accession No. Q75W19. The sequence has 63.4% identity with SEQ ID No. 28.
Database UniProt [Online] Mar. 1, 2002, "Cytochrome P450." XP002446804 retrieved from EBI accession No. UniProt:Q8W228. Database accession No. Q8W228. The sequence has 61.4% identity with SEQ ID No. 28.
Database UniProt [Online] Jun. 1, 2001, "Ferulate-5-hydroxylase." XP002446805 retrieved from EBI accession No. UniProt;Q0C543. Database accession No. Q9C543. The sequence has 54% identity with SEQ ID No. 28.
Database Geneseq [Online] Jul. 20, 1998, "*Arabidopsis* ferulate-5-hydroxylase." XP002446806 retrieved from EBI accession No. GSP:AAQ40099. Database accession No. AAW40099. The sequence has 54% identity with SEQ ID No. 28. Database Geneseq [Online] Jun. 1, 2006, "*Eucalyptus grandis* lignification-related protein SEQ ID No. 432." XP002446807 retrieved from EBI accession No. GSP:AEG90458. Database accession No. AEG90458. The sequence has 63.5% identity with SEQ ID No. 28.
Agrawal, N. et al., "RNA Interference: Biology, Mechanism, and Applications." *Microbiol. Mol. Biol. Rev.*, vol. 67:657, 2003.
Boerjan, W. et al., "Lignin Biosynthesis.", *Annu. Rev. Plant Biol.*, vol. 54:519, 2003.
Brummelkamp, T.R. et al., "A System for Stable Expression of Short Interfering RNAs in Mammalian Cells." *Science*, vol. 296:550, 2002.
Daglia, M. et al., "In Vitro and Ex Vivo Antihydroxyl Radical Activity of Green and Roasted Coffee." *J. of Agric. Food Chem.*, vol. 52: 1700, 2004.
Delgado-Andrade, C. "Assessing the Antioxidant Activity of Malanoidins From Coffee Brews by Different Antioxidant Methods." *J. Agric. Food Chem.*, vol. 53:7832-6, 2005.
Dixon, R.A. "The Biosynthesis of Monolignols: A "Metabolic Grid", Or Independent Pathways to Guaiacyl and Syringyl Units?" *Phytochemistry*, vol. 57:1069-84, 2001.

(Continued)

*Primary Examiner* — Brent T Page
(74) *Attorney, Agent, or Firm* — Potter Anderson & Corroon LLP

(57) ABSTRACT

Polynucleotides encoding polypeptides that comprise the biosynthetic pathway for lignins in the coffee plant are disclosed. Also disclosed are methods for using these polynucleotides and polypeptides for the manipulation of flavor, aroma, and other features of coffee beans, as well as the manipulation resistance to pathogen, herbivore, and insect attack in the coffee plant.

16 Claims, 12 Drawing Sheets

OTHER PUBLICATIONS

Elbashir, S. M. et al., "Analysis of Gene Function in Somatic Mammalian Cells Using Small Interfering RNAs." *Methods*, vol. 26:199-213, 2002.

Gowri, G. et al., "Molecular Cloning and Expression of Alfalfa S-Adenosyl-L-Methionine: Caffeic Acid 3-0-Methyltransferase, A Key Enzyme of Lignin Biosynthesis." *Plant Physiol.*, vol. 97:7-14, 1991.

Hatfield, R. and Vermerris, W. "Lignin Formation in Plants. The Dilemma of Linkage Specificity." *Plant Physiol.*, vol. 126:1351-1357, 2001.

Humphreys, J. M. and Chapple, C. "Rewriting the Lignin Roadmap." *Curr. Opin. Plant Biol.* vol. 5:224-229, 2002.

Kim, S. J. et al., "Functional Reclassification of the Putative Cinnamyl Alcohol Dehydrogenase Multigene Family in *Arabidopsis.*" *Proc. Natl. Acad. Sci. U S A.*, vol. 101:1455-60, 2004.

Klahre, U. et al., "High Molecular Weight RNAs and Small Interfering RNAs Induce Systemic Posttranscriptional Gene Silencing in Plants." *Proc. Natl. Acad. Sci. U S A.* vol. 99:11981, 2002.

Logemann, E. et al., "A Novel Type of Pathogen Defense-Related Cinnamyl Alcohol Dehydrogenase." *Biol. Chem.*, vol. 38, pp. 909-913, 1997.

Marita, J. M. et al., "Variations in the Cell Wall Composition of Maize Brown Midrib Mutants." *Agric. Food Chem.*, vol. 51:1313-1321, 2003.

Marraccini, P. et al., Molecular Cloning of the Complete 11S Seed Storage Protein Gene of *Coffea arabica* and Promoter Analysis in the Transgenic Tobacco Plants. *Plant Physiol. Biochem.*, vol. 37:273-282, 1999.

Marraccini, P. et al., "Rubisco Small Subunit of *Coffea Arabica*: Cdna Sequence, Gene Cloning and Promoter Analysis in Transgenic Tobacco Plants." *Plant Physiol. Biochem.*, vol. 41:17-25, 2003.

Meyer, K. et al. "Ferulate-5-Hydroxylase From *Arabidopsis thaliana* Defines a New Family of Cytochrome P450-Dependent Monooxygenases." *Proc. Natl. Acad. Sci. U S A.*, vol. 93:6869-6874, 1996.

Piquemal, J. et al., "Down-Regulation of Caffeic Acid O-Methyltransferase in Maize Revisited Using a Transgenic Approach." *Plant Physiol.*, vol. 130:1675-1685, 2002.

Ralph, J. et al., "NMR Characterization of Altered Lignins Extracted From Tobacco Plants Down-Regulated for Lignification Enzymes Cinnamylalcohol Dehydrogenase and Cinnamoyl-Coa Reductase." *Proc. Natl. Acad. Sci U S A.*, vol. 95:12803-12808, 1998.

Ruegger, M. et al., "Regulation of Ferulate-5-Hydroxylase Expression in *Arabidopsis* in the Context of Sinapate Ester Biosynthesis." *Plant Physiol.*, vol. 119:101-110, 1999.

Sibout, R. et al., "Cinnamyl Alcohol Dehydrogenase-C and D Are the Primary Genes Involved in Lignin Biosynthesis in the Floral Stem of *Arabidopsis."* *Plant Cell*, vol. 17, pp. 2059-2076, 2005.

Spanier, A. M. et al., "Meat Flavor: Contribution of Proteins and Peptides to the Flavor of Beef." *Adv. Exp. Med. Biol.*, vol. 542:33-49, 2004.

Tuschl T. and Borkhardt, A. "Small Interfering RNAs: A Revolutionary Tool for the Analysis of Gene Function and Gene Therapy." *Mol. Interv.*, vol. 2:158-167, 2002.

Vance, C. et al., "Lignification as a Defense Mechanism of Disease Resistance." *Annu. Rev. Phytopathol.*, vol. 18:259-288, 1980.

Whetten, R. W. et al., "Recent Advances in Understanding Lignin Biosynthesis." *Annu. Rev. Plant Physiol. Plant Mol. Biol.*, vol. 49:585-609, 1998.

Wu, G. et al., "Activation of Host Defense Mechanisms by Elevated Production of H2O2 in Transgenic Plants." *Plant Physiol.*, vol. 115:427-435, 1997.

Ye, Z. H. and Varner, J. E. "Differential Expression of Two O-Methyltransferases in Lignin Biosynthesis in *Zinnia Elegans."* *Plant Physiol.*, vol. 108:459-467, 1995.

Yeretzian, C. et al., "From the Green Bean to the Cup of Coffee: Investigating Coffee Roasting by On-Line Monitoring of Volatiles." *Eur. Food Res. Technol.*, vol. 214, pp. 92-104, 2002.

Zubieta, C. et al., "Structural Basis for the Modulation of Lignin Monomer Methylation by Caffeic Acid/5-Hydroxferulic Acid 3/5-O-Methyltransferase." *Plant Cell*, vol. 14, pp. 1265-1277, 2002.

\* cited by examiner

FIG. 2
(Page 1 of 3)

FIG. 2
(Page 2 of 3)

FIG. 2
(Page 3 of 3)

FIG. 3
(Page 1 of 3)

FIG. 3
(Page 2 of 3)

FIG. 3
(Page 3 of 3)

FIG. 4
(Page 1 of 3)

FIG. 4
(Page 2 of 3)

FIG. 4
(Page 3 of 3)

FIG. 5
(Page 1 of 2)

FIG. 5
(Page 2 of 2)

SEQUENCE LISTING

<160> NUMBER OF SEQ ID NOS: 42

<210> SEQ ID NO 1
<211> LENGTH: 1314
<212> TYPE: DNA
<213> ORGANISM: Coffea canephora

<400> SEQUENCE: 1

```
acctttcct  tcgtcccgga  agcttttccc  ttcacctttg  attcctctcc  agccaaacaa     60 acctacccc  caggacattt  ctgatttctg  aagctgaagt  tggagtaaaa  agaaaaagaa    120
atcaaataat  ggcagaggag  gaagcttgct  tattcgccat  gagcctggct  agtgcatccg    180
tccttcctat  ggtactcaaa  tcagccatcg  aacttgacct  cctggagctt  atagccaagg    240
ctggtcctgg  cgcctacgtc  tccccatcgg  aactcgccgc  acagtccccc  acccacaacc    300
cggaagctcc  tatcatgctt  gatcgcatcc  tccgactcct  ggccacctac  tctgtcctcg    360
attgcaagct  caacaatctg  gccgatggtg  gcgtcgagag  gctttacggt  ctggcccctg    420
tttgcaaatt  cttgaccaag  aacgctgatg  tgtgtccat   ggcccctctt  ttgctcatga    480
atcaagataa  ggtcctcatg  gaaagctggt  atcacttaaa  ggatgcggtt  cttgatggag    540
gaatcccttt  caacaaggcc  tacggaatga  ctgcattcga  atatcacgga  accgatccca    600
gattcaacaa  ggtgtttaac  cagggaatgt  ctaatcactc  caccattacc  atgaagaaga    660
ttttggaagt  ttacagaggg  tttgagggtc  tgaagacggt  ggtcgacgtg  ggaggtggaa    720
ctggggctac  gctcaatatg  atcatcagca  aatatcccac  gatcaaggc   atcaactttg    780 agctcccgca  cgtcgtagag  gacgccccgt  ctcattccgg  ggtggagcat  gtgggtgggg    840
atatgtttgt  tagcgtccct  aaaggggatg  ccattttcat  gaagtggatt  tgccatgatt    900
ggagcgacga  ccactgccgg  aaactcttga  agaactgcta  ccaagcactt  ccggacaacg    960
ggaaggtgat  ccttgccgaa  tgtgtccttc  cggaagcccc  agacacctcg  ctcgctactc   1020
agaatgtcgt  ccacgttgat  gtcgtcatgt  tggcccacaa  ccctggtggg  aaagagagga   1080
ctgagaagga  attcgaggcc  ttggcaaagg  gggctggatt  caaagaattc  cgcaaggttt   1140
gctctgctgt  caatacctgg  atcatggagc  tgtgcaaatg  aaggcttact  tgcttgaatg   1200 aacctttgt   tttgggagac  gtcattttt   ctcttgcgtg  attggattgg  tggtttctaa   1260
tcagtatagc  cgtctactaa  tgaaccttcc  ttctgtatta  ctattatttc  acag         1314
```

<210> SEQ ID NO 2
<211> LENGTH: 893

```
<212> TYPE: DNA
<213> ORGANISM: Coffea canephora

<400> SEQUENCE: 2
aaaagatata tcttgcagtt caatgggcta ctacagatca ttggttacag gcatggtgtt    60
tcgatgacaa agactctact tgattttcat ccaatgtatg aacttgggaa ttctttgctt   120
gaaggaggga ttccatttaa tagagttcat ggaatgcacg catttgacta ccctagtaga   180
gatcccaggt ataatgagct tttcaacaag ggaatggttg gtcctacagc cataacaatg   240
aaaaaattgc ttcaacaata taaggattt gagcaccttc agacattggt tgatgttggt    300
ggtggtcttg gaataaccct tcacaagatt atatcaaaat acccttctat aagggggtatc  360
aattttgatc tttccacatgt cattgaaaac gcgccatcct atcttggagt ggaacacatt  420
ggtggagaca tgtttgaaag cgttcctgga ggagatgcta tttttatgaa gatgatactc   480
catgattgga gtgatgatca ctgcttaaag ctgctgaaga actgcttcaa agctctacca   540
gatcatggca aagtcatcgt tgttgatttg gttctacccg taaaacctga tactagtgcc   600
tttgtaaaag gcattttcca gactgatgct ctcatgatga ctcaaaatcc tggagggaaa   660
gagcgatcag aatctgatgt tcgggccttg gctatcagag ctggatttaa agacataaag   720
ttagaatgtt gtgtgggtag tcttggggtc ctggagttgt acaaatagtt atgtctgccc   780
atttggcagg ttttcattt gaagaaattt cttttgtttg cttgtatttc ttaaataatc    840
tctatttggt ctaatgagcg tagtgtttct taaaaaaaaa aaaaaaaaa aaa            893

<210> SEQ ID NO 3
<211> LENGTH: 475
<212> TYPE: DNA
<213> ORGANISM: Coffea canephora

<400> SEQUENCE: 3
cttaatcatt tcaaaatttg ccgtcaatga gtggcaatta acacaacccc cacacccaat    60
ccaatatatg ctacagtaca actaatctga atttatatac gtatgaccta gctgggatct   120
atcatcatct acagatttaa gagttaaagg tagtagcagt agtgatatgg attcttcgtc   180
aagagcaacc gacaatgttg ttgttgaagc agggctagat gagcaagaag agcaacactt   240
ctcgtacgcg atgcagctgg tcacctctgt atctttgccc atggtgctgc tggctgccat   300
ccggctcgac gtgttggagg tcattgccca agcgggtcca ggtgcccaat tgtcgccttg   360
ggacattgca gcccaggtag gtcctaaaaa cccagatgcg gctgctatgc tggatagaat   420
gctgcagctc ctggctagct actcggtgct cacctgctct gttgccgagg cggat        475

<210> SEQ ID NO 4
<211> LENGTH: 983
<212> TYPE: DNA
<213> ORGANISM: Coffea canephora

<400> SEQUENCE: 4
caagttcttt gtacagaaca aaacaaaggg aggaggttca ctaggctccg ttctgggcct    60
gcttcaagat aaggtcttca ttgacagttg gtaccaatta gaagatgcag ttcgcaaagg   120
gggagatccg tttcagggg cgcacggtac acatgcattt gaatttcttg gaagcgaccc    180
cagattcaat gaggtattca acaaggcaat gatccaccac acagctatcg tcataaacag   240
aatgcttgaa cggtacaaag gttttgagca cctcaaaact tggtagatg ttggtggtgg    300
tcttggaatg aacctcaata taatcacaac taaatacccct agtctcaagg gtattaattt   360
tgatttgcca catgttatac aacatgcacc agcctatcct ggtgttgaac atgttggagg   420
```

```
agacatgttt gaaagtgttc cacaggggga tgccattttt atgaagtgga tacttcatga      480
ttgggatgat ggtcattgct tgaagctgct gaaaaattgt tacaaggctt taccagacaa      540
tggaaaggta atagctgttg acgcaattct tcctgtggtt cctgatgata gtgcacgcga      600
caaagctact tgccaagcag atcttgttgt ggtgactcaa tatagggag gaattgagag        660 atatgaaaca gagtttcttg ccctggctac tgctgctgga tttaaaggca taagtgtgaa      720
atgttttgta tgtaacttgt gggtcatgga gttctataag tagatgactg gttcatgggg      780
cactgtactt taaaacctta aatgttgtat gttgaatgat tgccaatgtc atggtgacta      840
tctgcaatct acaacgagga aaaaaactgc aatattgacc tcgtaagaat aaatttatac      900
attgttttgt ttccgaatat gataattatg atggagttaa ggcaaaaaaa aaaaaaaaaa      960
aaaaaaaaaa aaaaaaaaaa aaa                                               983

<210> SEQ ID NO 5
<211> LENGTH: 1265
<212> TYPE: DNA
<213> ORGANISM: Coffea canephora

<400> SEQUENCE: 5
aagcagtggt aacaacgcag agtacgcggg gaaccaaaaa agaactaata ctcataataa       60 agaaagaat aaaactttat ccaccttctt gatcaatcta tagtgaatct ggtactaaaa        120
tactaatccc actactgcta caagtaagca atcagacatg gcagcgtggg aggctgagaa      180
ggccaggaca gtatgtgtta caggagcagg gggatacctg ggatcttggt tagtcaagct      240
actcctttcc cgccattata ctgttcatgc caccctcaga aatcccgagg atgagaaata      300
tgttcatctg aagaaacttg acaaagcagc tgagaaattttg aaactcttta aggctgattt    360
gctggattac aactccattt ctgcagccat caggggctgt gatggcgtat tcatgtagc       420 tagtcctgtt ccttcaggct ctgttcccaa tcctgaggtt gaacttgttg agccggctgt      480
aaagggtacc cttaatgtac tgaaggcttg ttctgaagca aatgtcaagc gcgttgtagc      540
tgtttcctct gttgctgctg ttgttgtgag tcctaatcgg cataaaggtg aaattataga      600
tgagacgtgt tggtcagacg gggaatactg caagacaaca ataactggt attgttactc       660 caagacggtt gctgaaagtg aggctttaca atatgcaaaa gaaactggcc ttgatgtttt      720
aactgtatgc ccatcctttg ttctcggccc catgcttcag catgatgtga atgctagcag      780
tctggctctt ataaagctgt tgaaagaagg atatgaagaa atagaaaaca aattccggga      840
tatggtagat gtgcgtgatg tggctgaagc actgcttttg gtttacggga gacctgaagc      900
tgaagggcgg tacatatgtt catctcacct cactacgaca aaggatacgg tggaaattct      960
gaggaaaaac tatcccaact ataagtaccc taagagattt atagaggtga aggatgatca     1020
aggccgagga aatgttagct cagaaaaatt gcagaggctg ggctggagat ataggccagt     1080
ggaagaaact cttgttgact ctgtcgaaag ctaccagcag gctgggatct tggattgatc     1140
actttctgcc ttttctgttt ttttgttaat gggacttgtg gattattttg taaaagaatt     1200
tttggatcta ttaaaagtgg aatttgtgct tgtagaaaaa aaaaaaaaaa aaaaaaaaa      1260 aaaaa                                                                  1265

<210> SEQ ID NO 6
<211> LENGTH: 1354
<212> TYPE: DNA
<213> ORGANISM: Coffea canephora

<400> SEQUENCE: 6
```

```
cctttgcctt tcattgcaga agaaattttg ttctcgcgcg cagaaatctt ctcattactt    60
accaacctca cgtctcacct aaaccaaaaa gaaagaaaa gaaagaaaa accaggtcag    120 aagcatgcct tcagtttccg gccaagtcgt ctgtgtcact ggcgccggtg gctacatcgc   180
ttcctggata gttaagctcc tccttgaaaa aggctacact gttagaggaa ctgttagaaa   240
ccctgatgat gcgaagaatg gtcacttgcg ggagctagaa ggagcaaaag agagattgac   300
actatgcaga gctgaccttc ttgattatca gagtttacgt gaagccatca aaggctgtga   360
tggggttttc cacactgctt cccccgttac ggatgatccg gaacaaatgg tggagccagc   420
ggtgattggg accaaaaatg tgatcaacgc agccgccgag gccaaggtcc ggcggatggt   480
tttcacctca tcaattggtg cggtttacat ggaccccaac agggaacctg aaaaagttgt   540
ggacgagagt tgttggagtg atcttgaatt ctgcaagaat actaagaatt ggtattgcta   600
cgggaaagct gtggcagaaa aagcagcatg ggacgaagcc aaggagaaag gggtggattt   660
ggtggtgatc aacccggtgc tggtgttggg accattgttg caaccgaccg tgaatgccag   720
tattcttcat atcctcaaat acttgactgg atctgcaaag acttatgcca actctgtgca   780
ggcctacgtg cacgttaagg atgttgcatt ggcacacgtt cttatctacg agactccctc   840
ggcatctggg agatacctct gcgccgagag cgttcttcat cgcggtgaag tggttgaaat   900
cttggccaaa ctctttccgg agtacccaat tccaaccaag tgctccgatg aaacaagacc   960
aagagcaaaa gcttacaagt tcacaaatca gaagctcaag gatttggggt ttgaattcac  1020
accggtgaaa cagtgcctat atgagacggt taaaagtctt caggagaagg ggcagatacc  1080
cctccctact cagaacgata agcccattaa aattcactac tagtctgact ttattctggt  1140
tgctattgat atcaaaatgt tagcttttta tcattgaaga agaagaagta gtagaagtat  1200
aaagaatgtt taaggttgca atccaaatcc gttgcttgtg aaccagaatg tttaaggcag  1260
tagtatttgt gctccagatt tccgtacccg atgtgaagtc tttactacct aaaaaaaaaa  1320
aaaaaaaaaa aaaaaaaaaa aaaaaaaaaa aaaa                              1354

<210> SEQ ID NO 7
<211> LENGTH: 843
<212> TYPE: DNA
<213> ORGANISM: Coffea canephora

<400> SEQUENCE: 7
agcaaacgaa gttatggtat gttctctcaa agacattggc tgaggatgct gcctggaagt    60
ttgtaaaaga gaaaggttta gacatggtaa cgataaaccc agctatggtg attgggcctc   120
tgttacagcc aacacttaac accagtgctg ctgcaatttt gaatttaata aacggtgcag   180
aaacatttcc aaattcttct atgggctggg ttgatgtcaa agatgttgct aatgcacata   240
tactatagct tttgaaaatc catctgctag tggaagatac tgcctggtcg aaagagtggt   300
acactactct gaagttgtga agatcttgcg tgaaatttat ccttcctcaa aacttccaga   360
aaagtgcgct gatgacaagc catttgtgcc gacgtaccag gtttccaagg agaaggcaaa   420
aagcttaggt cttgaattca ttccccttga gcaaagcatc aaggaaacag ttgaaagctt   480
gaaggagaag aacttttggg actcttctgc tgcactttga atatcgcccg aaacatgatg   540
aggaacatcg agagttggta gcagtgccta ttgaaaatat gttttccaaa ccctatatg    600 taccaagcct ctctgactga cgttacatgc atccacagag atttagaatc tacatatgaa   660
acaataaagt actcgtcttt tttgctatac tgaaaatttg aacaggaaat atccttttgt   720
gtttcctgct gcaaattcaa ggatatagca atgatgagta gatttagtg cgtaattata   780
```

```
tgttggacga gaatttataa aatcaaggag cagcattcct tgtaaaaaaa aaaaaaaaa     840 aaa                                                                  843

<210> SEQ ID NO 8
<211> LENGTH: 1457
<212> TYPE: DNA
<213> ORGANISM: Coffea canephora

<400> SEQUENCE: 8
atcgattacc agaaatgtgt acaaatagac caaacccctta caaaatctttt gtctgttgga    60 acaagatctg tgtttgttgg aacaagaatt cacactctgc actcattttt tcacagaaaa   120
ggcggcaata atgaagacag tgtgtgtaac aggggcttcg ggctacatag catcatggct   180
tgtcaagttc ttgctccagc gtggttacac tgtcaaggca tctgttcgtg acctcaatga   240
tccaaagaaa gtagaacact tgcttgcact tgatggagct aaggagagac ttcagttgtt   300
caaagcaaac ctactggagg aaggttcctt tgatgctgcg attgatggtt gtgatggtgt   360
ttttcatatg gcctctcctt tctaccatac agtcactgat cctcaggctg aattgattga   420
tcctgctcta aaagggactc ttagtgttct gggatcatgt gcaaaatctc catctgttaa   480
aagagtggtt ttaacatcct ctatagctgc agttgccttc aacggcaagc ctcgtactcc   540
ggacgtggtg gttgatgaga cttggtggtc tcttcctgaa ttttgcaagc aaatgaagtt   600
atggtatgtt ctctcaaaga cattggctga ggatgctgcc tggaagtttg taaaagagaa   660
aggtttagac atggtaacga taaacccagc tatggtgatt gggcctctgt tacagccaac   720
acttaacacc agtgctgctg caattttgaa tttaataaac ggtgcagaaa catttccaaa   780
ttcttctatg ggctgggttg atgtcaaaga tgttgctaat gcacatattc tagcttttga   840
aaatccatct gctagtggaa gatactgcct ggttgaaaga gtggtacact actctgaagt   900
tgtgaacatc ttgcgtgaaa tttatccttc ctcaaaactt ccagaaaagt gcgctgatga   960
caagccattt gtgccgacgt accaggtttc caaggagaag gcaaaaagct taggtcttga  1020
attcattccc gttgagcaaa gcatcaagga aacagttgaa agcttgaagg agaagaactt  1080
tttgaactct tctgctgcac tttgaatatc acccgaaaca tgatgaggaa catcgagagt  1140
tggtagcatt gcctatttaa aatatgttgt ccaaactcct atatgtacca agcccgtctg  1200
actggcgtta catgcatcca cagagattta gaatctacat atgagacaat aaagtactcg  1260
tcttttttgc tatactgaaa atttgaacag gaaatatcct tttgtttttc ctgctgcaaa  1320
ttcaaggata tagcaatgat gagtagattt tagtgcgtaa ttatatgttg gacgagaatt  1380
tataaaatca aggagcacgc atttccttgt aatatcaggg taacgacttt ataaattaaa  1440
aaaaaaaaaa aaaaaaa                                                 1457

<210> SEQ ID NO 9
<211> LENGTH: 1521
<212> TYPE: DNA
<213> ORGANISM: Coffea canephora

<400> SEQUENCE: 9
ccaccaaaca ctttcttctc cacctatcat cggcgcctta attctgccaa tacacaaaac    60
tcctccattg ttttcattc catcgacttt tgtcatcatc tacttctctc tcaaccaaga   120
aaatccccaa aaaaatactg caaatgtttt agcaatataa cccagcagga gaaaagtcaa   180
cacttctgag ccctttaaa ggttacagaa acttaggagc agaggaaggg ggggagccat   240
cgcagcttgg cgctgccgtt ttcgccctgc tttcttcagc aaataaccct tgaaaaagag   300
```

```
acagaatgag cggagcggga aaggtggtgt gcgtgacagg agcatcagga tacatagctt    360
cttggttgat caagatgttg cttcatcgtg gttataccgt caaagcttca gttcgtgacc    420
tcaatgatcc aaaaaagaca gaattttttga tggcactgga tggagccaag gaaagacttc   480
acttgtttca tgcaaactta gtggaagagg gatcctttga tgcaatagtt gatggatgtg    540
aaggtgtttt tcatactgca tctccaatcc ttcatccagc gagtgtgacc aatccacaga    600
tagagcaatt ggatcctgca ctaaagggaa cactgaatgt gctgcgatct tgtgctagag    660
tttcatctat caaaagagtg gttttaacat cttctatgag agcagtgaca tgtaatcggg    720
aactaaagga tggtgttgta gttgatgaaa gttggtttgc agatccaaca tactgtgagg    780
agcgcaagtt gtggtatcca ctatcaaaga ttttggcaga gaatgctgct tgggaattct    840
caaaggagca tggtattgat atggttgcaa tcataccagg aatggtcatt ggtcccatct    900
tgcagcctta tcccagttta actgcaggaa tggtcctgaa cgtagtaaaa ggagctgcat    960
cgttctatac cgcgcgcatg agatgggttg atgttagaga tgttgcatat gcacatattc   1020 tagccttttga agtcccttct gccagtggaa gatattgtgt agttgaggga tttgcactgt   1080
ggactgagtt tatcaagact ctgaatgaat tgtatcctac tctccaactg tcagatgagt   1140
gttctactag tactccccta gttgagccac actacgaatt atcaaatgag aaagcaaagg   1200 gtttgggat tgagttcatt cctttcgacg tttgcctcaa ggataccatc gaaagcttca    1260
aagagaagaa cttggttaac ttctgaacaa aattcctaag cagactgaga ttggaaaata   1320
tacagtatcc aactattcat tctcttgtgt gagagtaaac tcttaaaagt atgggactgg   1380
tgaactttta ttgtagttga taattgtctc tggtactttt attgaactga tcgaacttta   1440
attgtagcaa tatgaaacca tgggaggggct atgccaagga aggcttaatc caaaaaaaaa   1500
aaaaaaaaaa aaaaaaaaaa a                                             1521

<210> SEQ ID NO 10
<211> LENGTH: 1309
<212> TYPE: DNA
<213> ORGANISM: Coffea canephora

<400> SEQUENCE: 10
ctttaagcag tggtaacaac gcagagtacg cggggagtc tgccagatgg atggatactc      60
tcatatccat tctgctacta atggccccgt aaggtgatcc ttggatgcaa ggctgacagg    120
taacaaattc gctcacaaaa agagcttgga gaagaatgag tggaccagga gaggataaag    180
tggtgtgtgt gactggagct tcgggttaca tagcttcatg gctggtcaag cagctacttg    240
gccggggtta tacagttaaa gcttctgttc gagatgccaa tgatccaaga aagacggaac    300
atttgacgtc acttgatgga gccaaggaga gactgaagtt gtttcaggcg aacttacttg    360
atgatggatc ctttgatgaa atagttcaag gatgtactgg cgttttttcat accgcttctc    420 ctgttaattt ttcggttagc gatccgaaga aagaattgct agaccctgca gtaaagggaa    480
cactgaacct gcttcaatca tgtgcaaaag tttcatctat cagaagagta atcctgacat    540
cttctacggc tgcagttctg gcaaaaccag agctaaataa agattcattt gttgacgaaa    600
gttggttttc taaccatca tactgtgagg agcaaaagat gtggtatcaa ctgtcaaaaa      660
ctttagcaga ggatgctgct tggaaattct caaaggagca tggcattgac atggtttcaa    720
tcaatccagg atgggtcttt ggtcccattt tgcagccttc tatcaatcta agtgcaggat    780
tggtcctgga tgtagtaaat gggtctcaat catttcctga tgcatgtgtt ggatggattg    840
atgttagaga tgttgcctgt gcacatattc atgcctttga aatccttct gctaatggaa     900
```

```
gatattgtgt agttgggaaa aatgtgcact ggtccgagat cgtcaagatt ctgaggcaac      960
ttttccctac tcttcaactt ccaaataaag gttctcctaa tagcaccttc ggtatgggag     1020
aattcgaagt gtcaatggag aaaacaaaag gtttgggaat caatttcatt ccattggaag     1080
tgagcctgaa ggacactgtt gaaagtttca tggagaagaa ttttattact ttttaaatca     1140
agaacggttt aaatttgtaa gaatttgtgt tcctaaaaca atcataaaga ttatttgtta     1200
tagttcatgg agttgtataa ttaaaaaaat tagtcaatgt tcgtaccatc tgttgtatct     1260
attgtaatta ttgattcttg gaaaaaaaaa aaaaaaaaa aaaaaaaa                   1309
```

<210> SEQ ID NO 11
<211> LENGTH: 717
<212> TYPE: DNA
<213> ORGANISM: Coffea canephora
<220> FEATURE:
<221> NAME/KEY: misc_feature
<222> LOCATION: (310)..(310)
<223> OTHER INFORMATION: n is a, c, g, or t

<400> SEQUENCE: 11

```
gctgaatgtg ctacagtctt gtgccaaagt tcaatctatc aaaagagtga ttttaacgtc       60
ttctattgca gcagttatat acaaagatga attaaaggac ggtgtcatag ttgacgaaag      120
ttggttttca gttccattat actgtgaaga gcacaagtta tggtatcaac tatcaaaaat      180
tttggcagag aatgctgctt gggatttctc aaaggagcat ggtattgaca tgattgcaat      240
taatccagga atggtcaccg gtcccttctt gcagccttct gccactttga gtgcagaagt      300
gatcttgagn cctagtaaat gtggaagata ttgcgtagtt gagagaactg caggctgctg      360
tgagcttatc aggattctga ctgaactctt cccaactctc cagttgccag ataaatattc      420
taatggcagt cccctaattc agctgaaata tgatgtatca aatgaaaaag taaaaggttt      480
gggcattgag ttcatgcctt tggaggtgag cctcaaggat actatcgaaa gcttcataga      540
gatgaaatta gttagccttt gaatcatggc attcatgtac tgtcatcaac ttgaaattgt      600
ttatatccaa gtttggaaaa cattcaattt caaacttctc attcttgttt gtacaaggta      660
cgcgattcag attatatata aagtagctaa attgtaaata aaaaaaaaa aaaaaaa         717
```

<210> SEQ ID NO 12
<211> LENGTH: 744
<212> TYPE: DNA
<213> ORGANISM: Coffea canephora

<400> SEQUENCE: 12

```
gccacacaaa aggtcgttat tcccctctca attccctctc tcggccctcg tctttcccta       60
aaacaaaaaa aatttccagc acacttccac tacacaaaca cacaccaata agaaactttc      120
cctcaccctc tcggctctat ctctccattt tttcaattca cacaacacac ccacaaacaa      180
ttcaaacaca acatagcaag caacaaagga ttaaagcttg ggagttcctt caaccatttg      240
gccgagaaac tcctacttgg attgaggaaa aagagacaga atgagcggag cgggaaaggt      300
ggtgtgcgtg acaggagcat caggatacat agcttcttgg ttgatcaaga tgttgcttca      360
tcgtggttat accgtcaaag cttcagttcg tgacctcaat gatccaaaaa agacagaatt      420
tttgatggca ctggatggag ccaaggaaag acttcacttg tttcatgcaa acttattgga      480
agatggatcc tttgatgcaa tagttgatgg atgtgaaggt gttttcata ctgcatctaa      540 caatccttca tccagcgagt gtgaccaatc gaaatagagc aattgcatcc tgcccaaaag      600
gaaaaactga aatgtccgtt atctagagca agagctaatt caaatcatcg gataggattt      660
```

```
aaaatactac aaagaaaaaa tcgcgcttgt aattcgaaac taaataaagc tgttggaagt      720
gcaccaaaac tccttataaa tcaa                                             744

<210> SEQ ID NO 13
<211> LENGTH: 697
<212> TYPE: DNA
<213> ORGANISM: Coffea canephora

<400> SEQUENCE: 13
aaactcacac atttacaatc aatcacagag agaatgagcg gagcagggaa ggtggttggt       60
gtgacgggag cttcagggta cgtagcttca tggctggtga agctgctgct tgagcggggt      120
tacactgtta aagcttccgt tcgtgacctc aatgatccag acaacacaga acatttgatt      180
tcacttgatg gagccaagga aaggcttcac ttgtttgttg ctgacttgat gaaagatgga      240
tcatttgatg aaatggttga tggatgtgaa ggtgtttttc atactgcatc tccattcaaa      300
cctgtagtta gtgatccaga ggcagaattg ttggaccctg cggtgaaggg aactctgaat      360
gtgctacaat catgtgcaag agtttcatct gtcaaaagag tggtagtgac atcttctata      420
gcctcggttg catacaaccg agaagcgaag gatggtgttg tagttgatga agttggtttt      480
tcagagccat catactgtga agaacgcaag ctctggtatg tactttcaaa aacgttggca      540
gagactgctg catggaagtt ctcaaaggag catggcattg atatgattac aattcatcca      600
tcatggatca ttggtcctca tttgcagcct tctatcaata caagtgtgca attgatcctg      660
aacctactaa atggggatga atcatttcct tacgcaa                               697

<210> SEQ ID NO 14
<211> LENGTH: 934
<212> TYPE: DNA
<213> ORGANISM: Coffea canephora

<400> SEQUENCE: 14
tttgaatttg atcgccgcca catcaaagca gttttggtgg acttgcttac tgcagcaatg       60
gacactacag ctacaactgt tgaatggata ctcgcggagc tcttgaaaaa ccccgagta      120 atgaagaaag tccagcaaga attggacgaa aaagtaggcc tacacaggat ggttgaggaa      180
tcagaattgg aaaaccctgac atacttagac atggttgtaa aggaagcatt aaggctccat      240
cctgttgtac cattacttct tcctcatgca gccttggagg attgcatagt tgacggtttc      300
catataccga aagattcccg agtgacgatc aatgctggga cgatcggaag agatccaaat      360
gcatggtctg atcctgagaa gtttacacca gagagattta ttgggagcaa catagatgta      420
agaggacatg atttccagct tattcccttt ggctcaggca gaagaatctg ccctggaatg      480
cagttggggc taactgtggt ccgtcttatg ttggcacgaa tggtgcattg tttcaattgg      540
gaacttccaa atgggatgct gccttcagag ctagacatga ccgaggaatt tggccttgtg      600
atgaccaggg ccaagcatct gatggctatt ccaacatatc gattgagcaa atgattaagc      660
aggtcttgag agatgcatgc tatttctata ttgcacctta tatattaagg tctactytgc      720
taagttcttg aaatgataaa tggttgtcaa gaataggtag gtattcatga cagaaccaag      780
tacttttaaa agcttcttct tttgtcactt ataaagtatg aaagatggaa tcttttttcac      840 aaaattctgt acagtttaaa taaggattac tgcattttty ttttatattc tcttataaag      900
tatgcatgtt aatttgaaaa aaaaaaaaaa aaaa                                  934

<210> SEQ ID NO 15
<211> LENGTH: 350
```

```
<212> TYPE: PRT
<213> ORGANISM: Coffea canephora

<400> SEQUENCE: 15

Met Ala Glu Glu Glu Ala Cys Leu Phe Ala Met Ser Leu Ala Ser Ala
1               5                   10                  15

Ser Val Leu Pro Met Val Leu Lys Ser Ala Ile Glu Leu Asp Leu Leu
            20                  25                  30

Glu Leu Ile Ala Lys Ala Gly Pro Gly Ala Tyr Val Ser Pro Ser Glu
        35                  40                  45

Leu Ala Ala Gln Leu Pro Thr His Asn Pro Glu Ala Pro Ile Met Leu
    50                  55                  60

Asp Arg Ile Leu Arg Leu Leu Ala Thr Tyr Ser Val Leu Asp Cys Lys
65                  70                  75                  80

Leu Asn Asn Leu Ala Asp Gly Gly Val Glu Arg Leu Tyr Gly Leu Ala
                85                  90                  95

Pro Val Cys Lys Phe Leu Thr Lys Asn Ala Asp Gly Val Ser Met Ala
            100                 105                 110

Pro Leu Leu Leu Met Asn Gln Asp Lys Val Leu Met Glu Ser Trp Tyr
        115                 120                 125

His Leu Lys Asp Ala Val Leu Asp Gly Gly Ile Pro Phe Asn Lys Ala
    130                 135                 140

Tyr Gly Met Thr Ala Phe Glu Tyr His Gly Thr Asp Pro Arg Phe Asn
145                 150                 155                 160

Lys Val Phe Asn Gln Gly Met Ser Asn His Ser Thr Ile Thr Met Lys
                165                 170                 175

Lys Ile Leu Glu Val Tyr Arg Gly Phe Glu Gly Leu Lys Thr Val Val
            180                 185                 190

Asp Val Gly Gly Gly Thr Gly Ala Thr Leu Asn Met Ile Ile Ser Lys
        195                 200                 205

Tyr Pro Thr Ile Lys Gly Ile Asn Phe Glu Leu Pro His Val Val Glu
    210                 215                 220

Asp Ala Pro Ser His Ser Gly Val Glu His Val Gly Gly Asp Met Phe
225                 230                 235                 240

Val Ser Val Pro Lys Gly Asp Ala Ile Phe Met Lys Trp Ile Cys His
                245                 250                 255

Asp Trp Ser Asp Asp His Cys Arg Lys Leu Leu Lys Asn Cys Tyr Gln
            260                 265                 270

Ala Leu Pro Asp Asn Gly Lys Val Ile Leu Ala Glu Cys Val Leu Pro
        275                 280                 285

Glu Ala Pro Asp Thr Ser Leu Ala Thr Gln Asn Val Val His Val Asp
    290                 295                 300

Val Val Met Leu Ala His Asn Pro Gly Gly Lys Glu Arg Thr Glu Lys
305                 310                 315                 320

Glu Phe Glu Ala Leu Ala Lys Gly Ala Gly Phe Lys Glu Phe Arg Lys
                325                 330                 335

Val Cys Ser Ala Val Asn Thr Trp Ile Met Glu Leu Cys Lys
            340                 345                 350

<210> SEQ ID NO 16
<211> LENGTH: 223
<212> TYPE: PRT
<213> ORGANISM: Coffea canephora

<400> SEQUENCE: 16

Tyr Glu Leu Gly Asn Ser Leu Leu Glu Gly Gly Ile Pro Phe Asn Arg
```

```
                1               5                   10                  15
Val His Gly Met His Ala Phe Asp Tyr Pro Ser Arg Asp Pro Arg Tyr
                    20                  25                  30

Asn Glu Leu Phe Asn Lys Gly Met Val Gly Pro Thr Ala Ile Thr Met
                35                  40                  45

Lys Lys Leu Leu Gln Gln Tyr Lys Gly Phe Glu His Leu Gln Thr Leu
            50                  55                  60

Val Asp Val Gly Gly Leu Gly Ile Thr Leu His Lys Ile Ile Ser
65                  70                  75                  80

Lys Tyr Pro Ser Ile Arg Gly Ile Asn Phe Asp Leu Pro His Val Ile
                    85                  90                  95

Glu Asn Ala Pro Ser Tyr Leu Gly Val Glu His Ile Gly Gly Asp Met
                100                 105                 110

Phe Glu Ser Val Pro Gly Gly Asp Ala Ile Phe Met Lys Met Ile Leu
            115                 120                 125

His Asp Trp Ser Asp Asp His Cys Leu Lys Leu Leu Lys Asn Cys Phe
        130                 135                 140

Lys Ala Leu Pro Asp His Gly Lys Val Ile Val Val Asp Leu Val Leu
145                 150                 155                 160

Pro Val Lys Pro Asp Thr Ser Ala Phe Val Lys Gly Ile Phe Gln Thr
                165                 170                 175

Asp Ala Leu Met Met Thr Gln Asn Pro Gly Gly Lys Glu Arg Ser Glu
                180                 185                 190

Ser Asp Val Arg Ala Leu Ala Ile Arg Ala Gly Phe Lys Asp Ile Lys
            195                 200                 205

Leu Glu Cys Cys Val Gly Ser Leu Gly Val Leu Glu Leu Tyr Lys
        210                 215                 220

<210> SEQ ID NO 17
<211> LENGTH: 103
<212> TYPE: PRT
<213> ORGANISM: Coffea canephora

<400> SEQUENCE: 17

Met Asp Ser Ser Ser Arg Ala Thr Asp Asn Val Val Glu Ala Gly
1               5                   10                  15

Leu Asp Glu Gln Glu Gln His Phe Ser Tyr Ala Met Gln Leu Val
                20                  25                  30

Thr Ser Val Ser Leu Pro Met Val Leu Leu Ala Ala Ile Arg Leu Asp
            35                  40                  45

Val Leu Glu Val Ile Ala Gln Ala Gly Pro Gly Ala Gln Leu Ser Pro
50                  55                  60

Trp Asp Ile Ala Ala Gln Val Gly Pro Lys Asn Pro Asp Ala Ala Ala
65                  70                  75                  80

Met Leu Asp Arg Met Leu Gln Leu Leu Ala Ser Tyr Ser Val Leu Thr
                85                  90                  95

Cys Ser Val Ala Glu Ala Asp
            100

<210> SEQ ID NO 18
<211> LENGTH: 253
<212> TYPE: PRT
<213> ORGANISM: Coffea canephora

<400> SEQUENCE: 18

Lys Phe Phe Val Gln Asn Lys Thr Lys Gly Gly Gly Ser Leu Gly Ser
1               5                   10                  15
```

Val Leu Gly Leu Leu Gln Asp Lys Val Phe Ile Asp Ser Trp Tyr Gln
            20                  25                  30

Leu Glu Asp Ala Val Arg Lys Gly Asp Pro Phe His Arg Ala His
        35                  40                  45

Gly Thr His Ala Phe Glu Phe Leu Gly Ser Asp Pro Arg Phe Asn Glu
        50                  55                  60

Val Phe Asn Lys Ala Met Ile His His Thr Ala Ile Val Ile Asn Arg
65                  70                  75                  80

Met Leu Glu Arg Tyr Lys Gly Phe Glu His Leu Lys Thr Leu Val Asp
                85                  90                  95

Val Gly Gly Gly Leu Gly Met Asn Leu Asn Ile Ile Thr Thr Lys Tyr
                100                 105                 110

Pro Ser Leu Lys Gly Ile Asn Phe Asp Leu Pro His Val Ile Gln His
            115                 120                 125

Ala Pro Ala Tyr Pro Gly Val Glu His Val Gly Gly Asp Met Phe Glu
130                 135                 140

Ser Val Pro Gln Gly Asp Ala Ile Phe Met Lys Trp Ile Leu His Asp
145                 150                 155                 160

Trp Asp Asp Gly His Cys Leu Lys Leu Leu Lys Asn Cys Tyr Lys Ala
                165                 170                 175

Leu Pro Asp Asn Gly Lys Val Ile Ala Val Asp Ala Ile Leu Pro Val
            180                 185                 190

Val Pro Asp Asp Ser Ala Arg Asp Lys Ala Thr Cys Gln Ala Asp Leu
        195                 200                 205

Val Val Val Thr Gln Tyr Arg Gly Gly Ile Glu Arg Tyr Glu Thr Glu
210                 215                 220

Phe Leu Ala Leu Ala Thr Ala Ala Gly Phe Lys Gly Ile Ser Val Lys
225                 230                 235                 240

Cys Phe Val Cys Asn Leu Trp Val Met Glu Phe Tyr Lys
                245                 250

<210> SEQ ID NO 19
<211> LENGTH: 326
<212> TYPE: PRT
<213> ORGANISM: Coffea canephora

<400> SEQUENCE: 19

Met Ala Ala Trp Glu Ala Glu Lys Ala Arg Thr Val Cys Val Thr Gly
1               5                   10                  15

Ala Gly Gly Tyr Leu Gly Ser Trp Leu Val Lys Leu Leu Leu Ser Arg
            20                  25                  30

His Tyr Thr Val His Ala Thr Leu Arg Asn Pro Glu Asp Glu Lys Tyr
        35                  40                  45

Val His Leu Lys Lys Leu Asp Lys Ala Ala Glu Asn Leu Lys Leu Phe
    50                  55                  60

Lys Ala Asp Leu Leu Asp Tyr Asn Ser Ile Ser Ala Ala Ile Arg Gly
65                  70                  75                  80

Cys Asp Gly Val Phe His Val Ala Ser Pro Val Pro Ser Gly Ser Val
                85                  90                  95

Pro Asn Pro Glu Val Glu Leu Val Glu Pro Ala Val Lys Gly Thr Leu
            100                 105                 110

Asn Val Leu Lys Ala Cys Ser Glu Ala Asn Val Lys Arg Val Val Ala
        115                 120                 125

Val Ser Ser Val Ala Ala Val Val Ser Pro Asn Arg His Lys Gly
130                 135                 140

Glu Ile Ile Asp Glu Thr Cys Trp Ser Asp Gly Glu Tyr Cys Lys Thr
145                 150                 155                 160

Thr Asn Asn Trp Tyr Cys Tyr Ser Lys Thr Val Ala Glu Ser Glu Ala
            165                 170                 175

Leu Gln Tyr Ala Lys Glu Thr Gly Leu Asp Val Leu Thr Val Cys Pro
        180                 185                 190

Ser Phe Val Leu Gly Pro Met Leu Gln His Asp Val Asn Ala Ser Ser
    195                 200                 205

Leu Ala Leu Ile Lys Leu Leu Lys Glu Gly Tyr Glu Glu Ile Glu Asn
210                 215                 220

Lys Phe Arg Asp Met Val Asp Val Arg Asp Val Ala Glu Ala Leu Leu
225                 230                 235                 240

Leu Val Tyr Gly Arg Pro Glu Ala Glu Gly Arg Tyr Ile Cys Ser Ser
                245                 250                 255

His Leu Thr Thr Thr Lys Asp Thr Val Glu Ile Leu Arg Lys Asn Tyr
            260                 265                 270

Pro Asn Tyr Lys Tyr Pro Lys Arg Phe Ile Glu Val Lys Asp Asp Gln
        275                 280                 285

Gly Arg Gly Asn Val Ser Ser Glu Lys Leu Gln Arg Leu Gly Trp Arg
290                 295                 300

Tyr Arg Pro Val Glu Glu Thr Leu Val Asp Ser Val Glu Ser Tyr Gln
305                 310                 315                 320

Gln Ala Gly Ile Leu Asp
                325

<210> SEQ ID NO 20
<211> LENGTH: 332
<212> TYPE: PRT
<213> ORGANISM: Coffea canephora

<400> SEQUENCE: 20

Met Pro Ser Val Ser Gly Gln Val Val Cys Val Thr Gly Ala Gly Gly
1               5                   10                  15

Tyr Ile Ala Ser Trp Ile Val Lys Leu Leu Glu Lys Gly Tyr Thr
            20                  25                  30

Val Arg Gly Thr Val Arg Asn Pro Asp Asp Ala Lys Asn Gly His Leu
        35                  40                  45

Arg Glu Leu Glu Gly Ala Lys Glu Arg Leu Thr Leu Cys Arg Ala Asp
    50                  55                  60

Leu Leu Asp Tyr Gln Ser Leu Arg Glu Ala Ile Lys Gly Cys Asp Gly
65                  70                  75                  80

Val Phe His Thr Ala Ser Pro Val Thr Asp Asp Pro Glu Gln Met Val
                85                  90                  95

Glu Pro Ala Val Ile Gly Thr Lys Asn Val Ile Asn Ala Ala Ala Glu
            100                 105                 110

Ala Lys Val Arg Arg Met Val Phe Thr Ser Ser Ile Gly Ala Val Tyr
        115                 120                 125

Met Asp Pro Asn Arg Glu Pro Glu Lys Val Val Asp Glu Ser Cys Trp
    130                 135                 140

Ser Asp Leu Glu Phe Cys Lys Asn Thr Lys Asn Trp Tyr Cys Tyr Gly
145                 150                 155                 160

Lys Ala Val Ala Glu Lys Ala Ala Trp Asp Glu Ala Lys Glu Lys Gly
                165                 170                 175

Val Asp Leu Val Val Ile Asn Pro Val Leu Val Leu Gly Pro Leu Leu
            180                 185                 190

```
Gln Pro Thr Val Asn Ala Ser Ile Leu His Ile Leu Lys Tyr Leu Thr
            195                 200                 205

Gly Ser Ala Lys Thr Tyr Ala Asn Ser Val Gln Ala Tyr Val His Val
            210                 215                 220

Lys Asp Val Ala Leu Ala His Val Leu Ile Tyr Glu Thr Pro Ser Ala
225                 230                 235                 240

Ser Gly Arg Tyr Leu Cys Ala Glu Ser Val Leu His Arg Gly Glu Val
            245                 250                 255

Val Glu Ile Leu Ala Lys Leu Phe Pro Glu Tyr Pro Ile Pro Thr Lys
            260                 265                 270

Cys Ser Asp Glu Thr Arg Pro Arg Ala Lys Ala Tyr Lys Phe Thr Asn
            275                 280                 285

Gln Lys Leu Lys Asp Leu Gly Phe Glu Phe Thr Pro Val Lys Gln Cys
            290                 295                 300

Leu Tyr Glu Thr Val Lys Ser Leu Gln Glu Lys Gly Gln Ile Pro Leu
305                 310                 315                 320

Pro Thr Gln Asn Asp Lys Pro Ile Lys Ile His Tyr
            325                 330

<210> SEQ ID NO 21
<211> LENGTH: 171
<212> TYPE: PRT
<213> ORGANISM: Coffea canephora

<400> SEQUENCE: 21

Gln Thr Lys Leu Trp Tyr Val Leu Ser Lys Thr Leu Ala Glu Asp Ala
1               5                   10                  15

Ala Trp Lys Phe Val Lys Glu Lys Gly Leu Asp Met Val Thr Ile Asn
            20                  25                  30

Pro Ala Met Val Ile Gly Pro Leu Leu Gln Pro Thr Leu Asn Thr Ser
            35                  40                  45

Ala Ala Ala Ile Leu Asn Leu Ile Asn Gly Ala Glu Thr Phe Pro Asn
        50                  55                  60

Ser Ser Met Gly Trp Val Asp Val Lys Asp Val Ala Asn Ala Tyr Thr
65                  70                  75                  80

Ile Ala Phe Glu Asn Pro Ser Ala Ser Gly Arg Tyr Cys Leu Val Glu
                85                  90                  95

Arg Val Val His Tyr Ser Glu Val Val Lys Ile Leu Arg Glu Ile Tyr
            100                 105                 110

Pro Ser Ser Lys Leu Pro Glu Lys Cys Ala Asp Asp Lys Pro Phe Val
            115                 120                 125

Pro Thr Tyr Gln Val Ser Lys Glu Lys Ala Lys Ser Leu Gly Leu Glu
        130                 135                 140

Phe Ile Pro Leu Glu Gln Ser Ile Lys Glu Thr Val Glu Ser Leu Lys
145                 150                 155                 160

Glu Lys Asn Phe Leu Asp Ser Ser Ala Ala Leu
                165                 170

<210> SEQ ID NO 22
<211> LENGTH: 324
<212> TYPE: PRT
<213> ORGANISM: Coffea canephora

<400> SEQUENCE: 22

Met Lys Thr Val Cys Val Thr Gly Ala Ser Gly Tyr Ile Ala Ser Trp
1               5                   10                  15
```

-continued

```
Leu Val Lys Phe Leu Leu Gln Arg Gly Tyr Thr Val Lys Ala Ser Val
         20                  25                  30

Arg Asp Leu Asn Asp Pro Lys Lys Val Glu His Leu Leu Ala Leu Asp
         35                  40                  45

Gly Ala Lys Glu Arg Leu Gln Leu Phe Lys Ala Asn Leu Leu Glu Glu
50                   55                  60

Gly Ser Phe Asp Ala Ala Ile Asp Gly Cys Asp Gly Val Phe His Met
65                   70                  75                  80

Ala Ser Pro Phe Tyr His Thr Val Thr Asp Pro Gln Ala Glu Leu Ile
                 85                  90                  95

Asp Pro Ala Leu Lys Gly Thr Leu Ser Val Leu Gly Ser Cys Ala Lys
                100                 105                 110

Ser Pro Ser Val Lys Arg Val Val Leu Thr Ser Ser Ile Ala Ala Val
                115                 120                 125

Ala Phe Asn Gly Lys Pro Arg Thr Pro Asp Val Val Asp Glu Thr
        130                 135                 140

Trp Trp Ser Leu Pro Glu Phe Cys Lys Gln Met Lys Leu Trp Tyr Val
145                 150                 155                 160

Leu Ser Lys Thr Leu Ala Glu Asp Ala Ala Trp Lys Phe Val Lys Glu
                165                 170                 175

Lys Gly Leu Asp Met Val Thr Ile Asn Pro Ala Met Val Ile Gly Pro
                180                 185                 190

Leu Leu Gln Pro Thr Leu Asn Thr Ser Ala Ala Ala Ile Leu Asn Leu
        195                 200                 205

Ile Asn Gly Ala Glu Thr Phe Pro Asn Ser Ser Met Gly Trp Val Asp
210                 215                 220

Val Lys Asp Val Ala Asn Ala His Ile Leu Ala Phe Glu Asn Pro Ser
225                 230                 235                 240

Ala Ser Gly Arg Tyr Cys Leu Val Glu Arg Val Val His Tyr Ser Glu
                245                 250                 255

Val Val Asn Ile Leu Arg Glu Ile Tyr Pro Ser Ser Lys Leu Pro Glu
                260                 265                 270

Lys Cys Ala Asp Asp Lys Pro Phe Val Pro Thr Tyr Gln Val Ser Lys
        275                 280                 285

Glu Lys Ala Lys Ser Leu Gly Leu Glu Phe Ile Pro Val Glu Gln Ser
290                 295                 300

Ile Lys Glu Thr Val Glu Ser Leu Lys Glu Lys Asn Phe Leu Asn Ser
305                 310                 315                 320

Ser Ala Ala Leu

<210> SEQ ID NO 23
<211> LENGTH: 326
<212> TYPE: PRT
<213> ORGANISM: Coffea canephora

<400> SEQUENCE: 23

Met Ser Gly Ala Gly Lys Val Val Cys Val Thr Gly Ala Ser Gly Tyr
1                 5                   10                  15

Ile Ala Ser Trp Leu Ile Lys Met Leu Leu His Arg Gly Tyr Thr Val
         20                  25                  30

Lys Ala Ser Val Arg Asp Leu Asn Asp Pro Lys Lys Thr Glu Phe Leu
         35                  40                  45

Met Ala Leu Asp Gly Ala Lys Glu Arg Leu His Leu Phe His Ala Asn
50                   55                  60

Leu Val Glu Glu Gly Ser Phe Asp Ala Ile Val Asp Gly Cys Glu Gly
```

```
                65                  70                  75                  80
Val Phe His Thr Ala Ser Pro Ile Leu His Pro Ala Ser Val Thr Asn
                    85                  90                  95

Pro Gln Ile Glu Gln Leu Asp Pro Ala Leu Lys Gly Thr Leu Asn Val
                    100                 105                 110

Leu Arg Ser Cys Ala Arg Val Ser Ile Lys Arg Val Val Leu Thr
                    115                 120                 125

Ser Ser Met Arg Ala Val Thr Cys Asn Arg Glu Leu Lys Asp Gly Val
        130                 135                 140

Val Val Asp Glu Ser Trp Phe Ala Asp Pro Thr Tyr Cys Glu Glu Arg
145                 150                 155                 160

Lys Leu Trp Tyr Pro Leu Ser Lys Ile Leu Ala Glu Asn Ala Ala Trp
                    165                 170                 175

Glu Phe Ser Lys Glu His Gly Ile Asp Met Val Ala Ile Ile Pro Gly
                    180                 185                 190

Met Val Ile Gly Pro Ile Leu Gln Pro Tyr Pro Ser Leu Thr Ala Gly
                195                 200                 205

Met Val Leu Asn Val Val Lys Gly Ala Ala Ser Phe Tyr Thr Ala Arg
        210                 215                 220

Met Arg Trp Val Asp Val Arg Asp Val Ala Tyr Ala His Ile Leu Ala
225                 230                 235                 240

Phe Glu Val Pro Ser Ala Ser Gly Arg Tyr Cys Val Val Glu Gly Phe
                    245                 250                 255

Ala Leu Trp Thr Glu Phe Ile Lys Thr Leu Asn Glu Leu Tyr Pro Thr
                    260                 265                 270

Leu Gln Leu Ser Asp Glu Cys Ser Thr Ser Thr Pro Leu Val Glu Pro
                    275                 280                 285

His Tyr Glu Leu Ser Asn Glu Lys Ala Lys Gly Leu Gly Ile Glu Phe
                290                 295                 300

Ile Pro Phe Asp Val Cys Leu Lys Asp Thr Ile Glu Ser Phe Lys Glu
305                 310                 315                 320

Lys Asn Leu Val Asn Phe
                325

<210> SEQ ID NO 24
<211> LENGTH: 326
<212> TYPE: PRT
<213> ORGANISM: Coffea canephora

<400> SEQUENCE: 24

Met Ser Gly Pro Gly Glu Asp Lys Val Val Cys Val Thr Gly Ala Ser
1               5                   10                  15

Gly Tyr Ile Ala Ser Trp Leu Val Lys Gln Leu Leu Gly Arg Gly Tyr
                    20                  25                  30

Thr Val Lys Ala Ser Val Arg Asp Ala Asn Asp Pro Arg Lys Thr Glu
                    35                  40                  45

His Leu Thr Ser Leu Asp Gly Ala Lys Glu Arg Leu Lys Leu Phe Gln
                50                  55                  60

Ala Asn Leu Leu Asp Asp Gly Ser Phe Asp Glu Ile Val Gln Gly Cys
65                  70                  75                  80

Thr Gly Val Phe His Thr Ala Ser Pro Val Asn Phe Ser Val Ser Asp
                    85                  90                  95

Pro Lys Lys Glu Leu Leu Asp Pro Ala Val Lys Gly Thr Leu Asn Leu
                    100                 105                 110

Leu Gln Ser Cys Ala Lys Val Ser Ser Ile Arg Arg Val Ile Leu Thr
```

```
            115                 120                 125
Ser Ser Thr Ala Ala Val Leu Ala Lys Pro Glu Leu Asn Lys Asp Ser
    130                 135                 140

Phe Val Asp Glu Ser Trp Phe Ser Asn Pro Ser Tyr Cys Glu Glu Gln
145                 150                 155                 160

Lys Met Trp Tyr Gln Leu Ser Lys Thr Leu Ala Glu Asp Ala Ala Trp
                165                 170                 175

Lys Phe Ser Lys Glu His Gly Ile Asp Met Val Ser Ile Asn Pro Gly
            180                 185                 190

Trp Val Phe Gly Pro Ile Leu Gln Pro Ser Ile Asn Leu Ser Ala Gly
        195                 200                 205

Leu Val Leu Asp Val Val Asn Gly Ser Gln Ser Phe Pro Asp Ala Cys
    210                 215                 220

Val Gly Trp Ile Asp Val Arg Asp Val Ala Cys Ala His Ile His Ala
225                 230                 235                 240

Phe Glu Ile Pro Ser Ala Asn Gly Arg Tyr Cys Val Val Gly Lys Asn
                245                 250                 255

Val His Trp Ser Glu Ile Val Lys Ile Leu Arg Gln Leu Phe Pro Thr
            260                 265                 270

Leu Gln Leu Pro Asn Lys Gly Ser Pro Asn Ser Thr Phe Gly Met Gly
        275                 280                 285

Glu Phe Glu Val Ser Met Glu Lys Thr Lys Gly Leu Gly Ile Asn Phe
    290                 295                 300

Ile Pro Leu Glu Val Ser Leu Lys Asp Thr Val Glu Ser Phe Met Glu
305                 310                 315                 320

Lys Asn Phe Ile Thr Phe
                325

<210> SEQ ID NO 25
<211> LENGTH: 183
<212> TYPE: PRT
<213> ORGANISM: Coffea canephora

<400> SEQUENCE: 25

Leu Asn Val Leu Gln Ser Cys Ala Lys Val Gln Ser Ile Lys Arg Val
1               5                   10                  15

Ile Leu Thr Ser Ser Ile Ala Ala Val Ile Tyr Lys Asp Glu Leu Lys
            20                  25                  30

Asp Gly Val Ile Val Asp Glu Ser Trp Phe Ser Val Pro Leu Tyr Cys
        35                  40                  45

Glu Glu His Lys Leu Trp Tyr Gln Leu Ser Lys Ile Leu Ala Glu Asn
    50                  55                  60

Ala Ala Trp Asp Phe Ser Lys Glu His Gly Ile Asp Met Ile Ala Ile
65                  70                  75                  80

Asn Pro Gly Met Val Thr Gly Pro Phe Leu Gln Pro Ser Ala Thr Leu
                85                  90                  95

Ser Ala Glu Val Ile Leu Pro Ser Lys Cys Gly Arg Tyr Cys Val Val
            100                 105                 110

Glu Arg Thr Ala Gly Cys Cys Glu Leu Ile Arg Ile Leu Thr Glu Leu
        115                 120                 125

Phe Pro Thr Leu Gln Leu Pro Asp Lys Tyr Ser Asn Gly Ser Pro Leu
    130                 135                 140

Ile Gln Leu Lys Tyr Asp Val Ser Asn Glu Lys Val Lys Gly Leu Gly
145                 150                 155                 160

Ile Glu Phe Met Pro Leu Glu Val Ser Leu Lys Asp Thr Ile Glu Ser
```

```
                    165                 170                 175

Phe Ile Glu Met Lys Leu Val
                180

<210> SEQ ID NO 26
<211> LENGTH: 86
<212> TYPE: PRT
<213> ORGANISM: Coffea canephora

<400> SEQUENCE: 26

Met Ser Gly Ala Gly Lys Val Val Cys Val Thr Gly Ala Ser Gly Tyr
1               5                   10                  15

Ile Ala Ser Trp Leu Ile Lys Met Leu Leu His Arg Gly Tyr Thr Val
            20                  25                  30

Lys Ala Ser Val Arg Asp Leu Asn Asp Pro Lys Lys Thr Glu Phe Leu
        35                  40                  45

Met Ala Leu Asp Gly Ala Lys Glu Arg Leu His Leu Phe His Ala Asn
    50                  55                  60

Leu Leu Glu Asp Gly Ser Phe Asp Ala Ile Val Asp Gly Cys Glu Gly
65                  70                  75                  80

Val Phe His Thr Ala Ser
                85

<210> SEQ ID NO 27
<211> LENGTH: 221
<212> TYPE: PRT
<213> ORGANISM: Coffea canephora

<400> SEQUENCE: 27

Met Ser Gly Ala Gly Lys Val Val Gly Val Thr Gly Ala Ser Gly Tyr
1               5                   10                  15

Val Ala Ser Trp Leu Val Lys Leu Leu Leu Glu Arg Gly Tyr Thr Val
            20                  25                  30

Lys Ala Ser Val Arg Asp Leu Asn Asp Pro Asp Asn Thr Glu His Leu
        35                  40                  45

Ile Ser Leu Asp Gly Ala Lys Glu Arg Leu His Leu Phe Val Ala Asp
    50                  55                  60

Leu Met Lys Asp Gly Ser Phe Asp Glu Met Val Asp Gly Cys Glu Gly
65                  70                  75                  80

Val Phe His Thr Ala Ser Pro Phe Lys Pro Val Val Ser Asp Pro Glu
                85                  90                  95

Ala Glu Leu Leu Asp Pro Ala Val Lys Gly Thr Leu Asn Val Leu Gln
            100                 105                 110

Ser Cys Ala Arg Val Ser Ser Val Lys Arg Val Val Thr Ser Ser
            115                 120                 125

Ile Ala Ser Val Ala Tyr Asn Arg Glu Ala Lys Asp Gly Val Val Val
    130                 135                 140

Asp Glu Ser Trp Phe Ser Glu Pro Ser Tyr Cys Glu Glu Arg Lys Leu
145                 150                 155                 160

Trp Tyr Val Leu Ser Lys Thr Leu Ala Glu Thr Ala Ala Trp Lys Phe
                165                 170                 175

Ser Lys Glu His Gly Ile Asp Met Ile Thr Ile His Pro Ser Trp Ile
            180                 185                 190

Ile Gly Pro His Leu Gln Pro Ser Ile Asn Thr Ser Val Gln Leu Ile
        195                 200                 205

Leu Asn Leu Leu Asn Gly Asp Glu Ser Phe Pro Tyr Ala
    210                 215                 220
```

<210> SEQ ID NO 28
<211> LENGTH: 217
<212> TYPE: PRT
<213> ORGANISM: Coffea canephora

<400> SEQUENCE: 28

```
Phe Glu Phe Asp Arg Arg His Ile Lys Ala Val Leu Val Asp Leu Leu
1               5                   10                  15

Thr Ala Ala Met Asp Thr Thr Ala Thr Thr Val Glu Trp Ile Leu Ala
            20                  25                  30

Glu Leu Leu Lys Asn Pro Arg Val Met Lys Lys Val Gln Gln Glu Leu
        35                  40                  45

Asp Glu Lys Val Gly Leu His Arg Met Val Glu Glu Ser Glu Leu Glu
    50                  55                  60

Asn Leu Thr Tyr Leu Asp Met Val Val Lys Glu Ala Leu Arg Leu His
65                  70                  75                  80

Pro Val Val Pro Leu Leu Pro His Ala Ala Leu Glu Asp Cys Ile
                85                  90                  95

Val Asp Gly Phe His Ile Pro Lys Asp Ser Arg Val Thr Ile Asn Ala
            100                 105                 110

Trp Thr Ile Gly Arg Asp Pro Asn Ala Trp Ser Asp Pro Glu Lys Phe
        115                 120                 125

Thr Pro Glu Arg Phe Ile Gly Ser Asn Ile Asp Val Arg Gly His Asp
    130                 135                 140

Phe Gln Leu Ile Pro Phe Gly Ser Gly Arg Arg Ile Cys Pro Gly Met
145                 150                 155                 160

Gln Leu Gly Leu Thr Val Val Arg Leu Met Leu Ala Arg Met Val His
                165                 170                 175

Cys Phe Asn Trp Glu Leu Pro Asn Gly Met Leu Pro Ser Glu Leu Asp
            180                 185                 190

Met Thr Glu Glu Phe Gly Leu Val Met Thr Arg Ala Lys His Leu Met
        195                 200                 205

Ala Ile Pro Thr Tyr Arg Leu Ser Lys
    210                 215
```

<210> SEQ ID NO 29
<211> LENGTH: 350
<212> TYPE: PRT
<213> ORGANISM: Coffea canephora

<400> SEQUENCE: 29

```
Met Ala Glu Glu Glu Ala Cys Leu Phe Ala Met Ser Leu Ala Ser Ala
1               5                   10                  15

Ser Val Leu Pro Met Val Leu Lys Ser Ala Ile Glu Leu Asp Leu Leu
            20                  25                  30

Glu Leu Ile Ala Lys Ala Gly Pro Gly Ala Tyr Val Ser Pro Ser Glu
        35                  40                  45

Leu Ala Ala Gln Leu Pro Thr His Asn Pro Glu Ala Pro Ile Met Leu
    50                  55                  60

Asp Arg Ile Leu Arg Leu Leu Ala Thr Tyr Ser Val Leu Asp Cys Lys
65                  70                  75                  80

Leu Asn Asn Leu Ala Asp Gly Gly Val Glu Arg Leu Tyr Gly Leu Ala
                85                  90                  95

Pro Val Cys Lys Phe Leu Thr Lys Asn Ala Asp Gly Val Ser Met Ala
            100                 105                 110
```

```
Pro Leu Leu Leu Met Asn Gln Asp Lys Val Leu Met Glu Ser Trp Tyr
        115                 120                 125

His Leu Lys Asp Ala Val Leu Asp Gly Gly Ile Pro Phe Asn Lys Ala
    130                 135                 140

Tyr Gly Met Thr Ala Phe Glu Tyr His Gly Thr Asp Pro Arg Phe Asn
145                 150                 155                 160

Lys Val Phe Asn Gln Gly Met Ser Asn His Ser Thr Ile Thr Met Lys
                165                 170                 175

Lys Ile Leu Glu Val Tyr Arg Gly Phe Glu Gly Leu Lys Thr Val Val
            180                 185                 190

Asp Val Gly Gly Gly Thr Gly Ala Thr Leu Asn Met Ile Ile Ser Lys
        195                 200                 205

Tyr Pro Thr Ile Lys Gly Ile Asn Phe Glu Leu Pro His Val Val Glu
    210                 215                 220

Asp Ala Pro Ser His Ser Gly Val Glu His Val Gly Gly Asp Met Phe
225                 230                 235                 240

Val Ser Val Pro Lys Gly Asp Ala Ile Phe Met Lys Trp Ile Cys His
                245                 250                 255

Asp Trp Ser Asp Asp His Cys Arg Lys Leu Leu Lys Asn Cys Tyr Gln
            260                 265                 270

Ala Leu Pro Asp Asn Gly Lys Val Ile Leu Ala Glu Cys Val Leu Pro
        275                 280                 285

Glu Ala Pro Asp Thr Ser Leu Ala Thr Gln Asn Val Val His Val Asp
    290                 295                 300

Val Val Met Leu Ala His Asn Pro Gly Gly Lys Glu Arg Thr Glu Lys
305                 310                 315                 320

Glu Phe Glu Ala Leu Ala Lys Gly Ala Gly Phe Lys Glu Phe Arg Lys
                325                 330                 335

Val Cys Ser Ala Val Asn Thr Trp Ile Met Glu Leu Cys Lys
            340                 345                 350

<210> SEQ ID NO 30
<211> LENGTH: 350
<212> TYPE: PRT
<213> ORGANISM: Coffea canephora

<400> SEQUENCE: 30

Met Ala Glu Glu Ala Cys Leu Phe Ala Met Ser Leu Ala Ser Ala
1               5                   10                  15

Ser Val Leu Pro Met Val Leu Lys Ser Ala Ile Glu Leu Asp Leu Leu
            20                  25                  30

Glu Leu Ile Ala Lys Ala Gly Pro Gly Ala Tyr Val Ser Pro Ser Glu
        35                  40                  45

Leu Ala Ala Gln Leu Pro Thr His Asn Pro Glu Ala Pro Ile Met Leu
    50                  55                  60

Asp Arg Ile Leu Arg Leu Leu Ala Thr Tyr Ser Val Leu Asp Cys Lys
65                  70                  75                  80

Leu Asn Asn Leu Ala Asp Gly Gly Val Glu Arg Leu Tyr Gly Leu Ala
                85                  90                  95

Pro Val Cys Lys Phe Leu Thr Lys Asn Ala Asp Gly Val Ser Met Ala
            100                 105                 110

Pro Leu Leu Leu Met Asn Gln Asp Lys Val Leu Met Glu Ser Trp Tyr
        115                 120                 125

His Leu Lys Asp Ala Val Leu Asp Gly Gly Ile Pro Phe Asn Lys Ala
    130                 135                 140
```

```
Tyr Gly Met Thr Ala Phe Glu Tyr His Gly Thr Asp Pro Arg Phe Asn
145                 150                 155                 160

Lys Val Phe Asn Gln Gly Met Ser Asn His Ser Thr Ile Thr Met Lys
                165                 170                 175

Lys Ile Leu Glu Val Tyr Arg Gly Phe Glu Gly Leu Lys Thr Val Val
            180                 185                 190

Asp Val Gly Gly Gly Thr Gly Ala Thr Leu Asn Met Ile Ile Ser Lys
            195                 200                 205

Tyr Pro Thr Ile Lys Gly Ile Asn Phe Glu Leu Pro His Val Val Glu
        210                 215                 220

Asp Ala Pro Ser His Pro Gly Val Glu His Val Gly Gly Asp Met Phe
225                 230                 235                 240

Val Ser Val Pro Lys Gly Asp Ala Ile Phe Met Lys Trp Ile Cys His
                245                 250                 255

Asp Trp Ser Asp Asp His Cys Arg Lys Leu Leu Arg Asn Cys Tyr Gln
            260                 265                 270

Ala Leu Pro Asp Asn Gly Lys Val Ile Leu Ala Glu Cys Val Leu Pro
        275                 280                 285

Glu Ala Pro Asp Thr Ser Leu Ala Thr Gln Asn Val Val His Val Asp
290                 295                 300

Val Val Met Leu Ala His Asn Pro Gly Gly Lys Glu Arg Thr Glu Lys
305                 310                 315                 320

Glu Phe Glu Ala Leu Ala Lys Gly Ala Gly Phe Lys Glu Phe Arg Lys
                325                 330                 335

Val Cys Ser Ala Val Asn Thr Trp Ile Met Glu Leu Cys Lys
            340                 345                 350

<210> SEQ ID NO 31
<211> LENGTH: 365
<212> TYPE: PRT
<213> ORGANISM: Medicago sativa

<400> SEQUENCE: 31

Met Gly Ser Thr Gly Glu Thr Gln Ile Thr Pro Thr His Ile Ser Asp
1               5                   10                  15

Glu Glu Ala Asn Leu Phe Ala Met Gln Leu Ala Ser Ala Ser Val Leu
                20                  25                  30

Pro Met Ile Leu Lys Ser Ala Leu Glu Leu Asp Leu Leu Glu Ile Ile
            35                  40                  45

Ala Lys Ala Gly Pro Gly Ala Gln Ile Ser Pro Ile Glu Ile Ala Ser
        50                  55                  60

Gln Leu Pro Thr Thr Asn Pro Asp Ala Pro Val Met Leu Asp Arg Met
65                  70                  75                  80

Leu Arg Leu Leu Ala Cys Tyr Ile Ile Leu Thr Cys Ser Val Arg Thr
                85                  90                  95

Gln Gln Asp Gly Lys Val Gln Arg Leu Tyr Gly Leu Ala Thr Val Ala
            100                 105                 110

Lys Tyr Leu Val Lys Asn Glu Asp Gly Val Ser Ile Ser Ala Leu Asn
        115                 120                 125

Leu Met Asn Gln Asp Lys Val Leu Met Glu Ser Trp Tyr His Leu Lys
130                 135                 140

Asp Ala Val Leu Asp Gly Gly Ile Pro Phe Asn Lys Ala Tyr Gly Met
145                 150                 155                 160

Thr Ala Phe Glu Tyr His Gly Thr Asp Pro Arg Phe Asn Lys Val Phe
                165                 170                 175
```

```
Asn Lys Gly Met Ser Asp His Ser Thr Ile Thr Met Lys Lys Ile Leu
            180                 185                 190

Glu Thr Tyr Thr Gly Phe Glu Gly Leu Lys Ser Leu Val Asp Val Gly
        195                 200                 205

Gly Gly Thr Gly Ala Val Ile Asn Thr Ile Val Ser Lys Tyr Pro Thr
    210                 215                 220

Ile Lys Gly Ile Asn Phe Asp Leu Pro His Val Ile Glu Asp Ala Pro
225                 230                 235                 240

Ser Tyr Pro Gly Val Glu His Val Gly Gly Asp Met Phe Val Ser Ile
                245                 250                 255

Pro Lys Ala Asp Ala Val Phe Met Lys Trp Ile Cys His Asp Trp Ser
            260                 265                 270

Asp Glu His Cys Leu Lys Phe Leu Lys Asn Cys Tyr Glu Ala Leu Pro
        275                 280                 285

Asp Asn Gly Lys Val Ile Val Ala Glu Cys Ile Leu Pro Val Ala Pro
    290                 295                 300

Asp Ser Ser Leu Ala Thr Lys Gly Val Val His Ile Asp Val Ile Met
305                 310                 315                 320

Leu Ala His Asn Pro Gly Gly Lys Glu Arg Thr Gln Lys Glu Phe Glu
                325                 330                 335

Asp Leu Ala Lys Gly Ala Gly Phe Gln Gly Phe Lys Val His Cys Asn
            340                 345                 350

Ala Phe Asn Thr Tyr Ile Met Glu Phe Leu Lys Lys Val
        355                 360                 365

<210> SEQ ID NO 32
<211> LENGTH: 364
<212> TYPE: PRT
<213> ORGANISM: Nicotiana tabacum

<400> SEQUENCE: 32

Met Glu Ser Ser Thr Lys Ser Gln Ile Pro Thr Gln Ser Glu Glu Glu
1               5                   10                  15

Arg Asn Cys Thr Tyr Ala Met Gln Leu Leu Ser Ser Ser Val Leu Pro
            20                  25                  30

Phe Val Leu His Ser Thr Ile Gln Leu Glu Val Phe Glu Ile Leu Ala
        35                  40                  45

Lys Ser Asn Asp Thr Lys Leu Ser Ala Ser Gln Ile Val Ser Gln Ile
    50                  55                  60

Pro Asn Cys Thr Lys Pro Glu Ala Pro Thr Met Leu Asn Arg Met Leu
65                  70                  75                  80

Tyr Val Leu Ala Ser Tyr Ser Leu Phe Thr Cys Ser Ile Val Glu Asp
                85                  90                  95

Glu Lys Asn Asn Gly Gly Gln Lys Arg Val Tyr Gly Leu Ser Gln Val
            100                 105                 110

Gly Lys Phe Phe Val Lys Asn Glu Asn Gly Ala Ser Met Gly Pro Leu
        115                 120                 125

Leu Ala Leu Leu Gln Asn Lys Val Phe Ile Asn Ser Trp Phe Glu Leu
    130                 135                 140

Lys Asp Ala Val Leu Glu Gly Gly Val Pro Phe Asp Arg Val His Gly
145                 150                 155                 160

Val His Ala Phe Glu Tyr Pro Lys Ser Asp Pro Lys Phe Asn Asp Val
                165                 170                 175

Phe Asn Lys Ala Met Ile Asn His Thr Thr Val Val Met Lys Lys Ile
            180                 185                 190
```

```
Leu Glu Asn Tyr Lys Gly Phe Glu Asn Leu Lys Thr Leu Val Asp Val
        195                 200                 205
Gly Gly Gly Leu Gly Val Asn Leu Lys Met Ile Thr Ser Lys Tyr Pro
210                 215                 220
Thr Ile Lys Gly Thr Asn Phe Asp Leu Pro His Val Val Gln His Ala
225                 230                 235                 240
Pro Ser Tyr Pro Gly Val Glu His Val Gly Gly Asp Met Phe Glu Ser
                245                 250                 255
Val Pro Glu Gly Asp Ala Ile Phe Met Lys Trp Ile Leu His Asp Trp
            260                 265                 270
Ser Asp Ser His Asn Leu Lys Leu Leu Lys Asn Cys Tyr Lys Ala Leu
        275                 280                 285
Pro Asp Asn Gly Lys Val Ile Val Val Glu Ala Ile Leu Pro Val Lys
290                 295                 300
Pro Asp Ile Asp Thr Ala Val Val Gly Val Ser Gln Cys Asp Leu Ile
305                 310                 315                 320
Met Met Ala Gln Asn Pro Gly Gly Lys Glu Arg Ser Glu Glu Glu Phe
                325                 330                 335
Arg Ala Leu Ala Thr Glu Ala Gly Phe Lys Gly Val Asn Leu Ile Cys
            340                 345                 350
Cys Val Cys Asn Phe Trp Val Met Glu Phe Cys Lys
        355                 360

<210> SEQ ID NO 33
<211> LENGTH: 354
<212> TYPE: PRT
<213> ORGANISM: Zinnia elegans

<400> SEQUENCE: 33

Met Gly Ser Asn Gln Asp Asp Gln Ala Phe Leu Phe Ala Met Gln Leu
1               5                   10                  15
Ala Ser Ala Ser Val Leu Pro Met Val Leu Lys Thr Ala Ile Glu Leu
            20                  25                  30
Asp Leu Leu Glu Thr Ile Ala Lys Ala Gly Pro His Gly Ser Val Ser
        35                  40                  45
Ser Ser Glu Leu Val Ala Gln Leu Pro Lys Val Asn Asn Pro Glu Ala
    50                  55                  60
Pro Val Met Ile Asp Arg Ile Cys Ser Leu Leu Ala Ser Tyr Ser Val
65                  70                  75                  80
Leu Thr Cys Thr Leu Lys Glu Thr Ala Asp Gly Cys Ala Glu Arg Phe
                85                  90                  95
Tyr Gly Leu Ala Pro Val Cys Lys Phe Leu Ile Lys Asn Asp Ala Gly
            100                 105                 110
Val Ser Leu Ala Pro Leu Leu Leu Met Asn Gln Asp Lys Val Leu Met
        115                 120                 125
Glu Ser Trp Tyr Tyr Leu Lys Asp Pro Val Leu Asp Gly Gly Ile Pro
    130                 135                 140
Phe Asn Lys Ala Tyr Gly Met Ser Ala Phe Glu Tyr His Gly Lys Asp
145                 150                 155                 160
Gln Arg Phe Asn Lys Val Phe Asn Ser Gly Met Phe Asn His Ser Thr
                165                 170                 175
Met Thr Met Lys Lys Ile Val Glu Leu Tyr Asn Gly Phe Ser Gly Leu
            180                 185                 190
Lys Thr Leu Val Asp Val Gly Gly Gly Thr Gly Ala Ser Leu Asn Met
        195                 200                 205
```

```
Ile Thr Ser Lys His Lys Ser Leu Lys Gly Ile Asn Phe Asp Leu Pro
        210                 215                 220

His Val Ile Ala Asp Ala Thr Thr Tyr Gln Gly Ile Glu His Val Gly
225                 230                 235                 240

Gly Asp Met Phe Glu Ser Val Pro Lys Gly Asp Ala Ile Phe Met Lys
                    245                 250                 255

Trp Ile Leu His Asp Trp Ser Asp Ala His Cys Leu Gln Val Leu Lys
                260                 265                 270

Asn Cys Tyr Lys Ser Leu Pro Glu Asn Gly Lys Val Ile Val Ala Glu
            275                 280                 285

Cys Ile Leu Pro Glu Ala Pro Asp Thr Thr Pro Ala Thr Gln Asn Val
290                 295                 300

Ile His Ile Asp Val Ile Met Leu Ala His Asn Pro Gly Gly Lys Glu
305                 310                 315                 320

Arg Thr Glu Lys Glu Phe Glu Ala Leu Ala Lys Gly Ala Gly Phe Lys
                325                 330                 335

Gly Phe Asn Lys Ala Ala Cys Ala Leu Asn Thr Trp Val Met Glu Phe
                340                 345                 350

Cys Lys

<210> SEQ ID NO 34
<211> LENGTH: 317
<212> TYPE: PRT
<213> ORGANISM: Eucalyptus gunnii

<400> SEQUENCE: 34

Met Pro Val Asp Ala Leu Pro Gly Ser Gly Gln Thr Val Cys Val Thr
1               5                   10                  15

Gly Ala Gly Gly Phe Ile Ala Ser Trp Ile Val Lys Leu Leu Leu Glu
                20                  25                  30

Arg Gly Tyr Thr Val Arg Gly Thr Val Arg Asn Pro Asp Asp Pro Lys
            35                  40                  45

Asn Gly His Leu Arg Glu Leu Glu Gly Ala Ser Glu Arg Leu Thr Leu
50                  55                  60

Tyr Lys Gly Asp Leu Met Asp Tyr Gly Ser Leu Glu Glu Ala Ile Lys
65                  70                  75                  80

Gly Cys Asp Gly Val Val His Thr Ala Ser Pro Val Thr Asp Asp Pro
                85                  90                  95

Glu Gln Met Val Glu Pro Ala Val Ile Gly Thr Lys Asn Val Ile Val
            100                 105                 110

Ala Ala Ala Glu Ala Lys Val Arg Arg Val Val Phe Thr Ser Ser Ile
        115                 120                 125

Gly Ala Val Thr Met Asp Pro Asn Arg Gly Pro Asp Val Val Val Asp
    130                 135                 140

Glu Ser Cys Trp Ser Asp Leu Glu Phe Cys Lys Ser Thr Lys Asn Trp
145                 150                 155                 160

Tyr Cys Tyr Gly Lys Ala Val Ala Glu Lys Ala Ala Trp Pro Glu Ala
                165                 170                 175

Lys Glu Arg Gly Val Asp Leu Val Val Ile Asn Pro Val Leu Val Leu
            180                 185                 190

Gly Pro Leu Leu Gln Ser Thr Ile Asn Ala Ser Ile Ile His Ile Leu
        195                 200                 205

Lys Tyr Leu Thr Gly Ser Ala Lys Thr Tyr Ala Asn Ser Val Gln Ala
    210                 215                 220

Tyr Val His Val Lys Asp Val Ala Leu Ala His Val Leu Val Leu Glu
```

```
                225                 230                 235                 240
Thr Pro Ser Ala Ser Gly Arg Tyr Leu Cys Ala Glu Ser Val Leu His
                245                 250                 255

Arg Gly Asp Val Val Glu Ile Leu Ala Lys Phe Phe Pro Glu Tyr Asn
            260                 265                 270

Val Pro Thr Lys Ser Lys Leu Ser Arg Ala Cys Arg Lys Ala Thr
        275                 280                 285

Tyr Pro Ser Pro Pro Arg Lys Ile Arg Cys Val Phe Arg Asp Asp
    290                 295                 300

Leu Arg Ser Ile Thr Val His Ile Cys Asn Pro Glu Lys
305                 310                 315

<210> SEQ ID NO 35
<211> LENGTH: 357
<212> TYPE: PRT
<213> ORGANISM: Triticum aestivum

<400> SEQUENCE: 35

Met Pro Ile Glu Ala Ala Asp Asn Val Pro Ala Glu Leu Pro Gly His
1               5                   10                  15

Gly Arg Thr Val Cys Val Thr Gly Ala Gly Gly Phe Ile Ala Ser Trp
            20                  25                  30

Leu Val Lys Arg Leu Leu Gln Lys Gly Tyr Asn Val Arg Gly Thr Val
        35                  40                  45

Arg Asn Pro Val Asp Pro Lys Asn Asp His Leu Arg Ala Phe Asp Gly
    50                  55                  60

Ala Ala Asp Arg Leu Val Leu Arg Ala Asp Leu Met Glu Pro Glu
65              70                  75                  80

Thr Leu Val Glu Ala Phe Thr Gly Cys Glu Gly Ile Phe His Ala Ala
                85                  90                  95

Ser Pro Val Thr Asp Asp Pro Glu Lys Met Ile Glu Pro Ala Ile Arg
            100                 105                 110

Gly Thr Lys Tyr Val Ile Thr Ala Ala Ala Asp Met Gly Ile Lys Arg
        115                 120                 125

Val Val Phe Thr Ser Thr Ile Gly Thr Val Tyr Met Asn Pro Asn Arg
    130                 135                 140

Asp Pro Ser Lys Pro Val Asp Asp Thr Cys Trp Ser Asp Leu Glu Tyr
145                 150                 155                 160

Cys Lys Lys Thr Ala Asn Trp Tyr Cys Tyr Ala Lys Thr Val Ala Glu
                165                 170                 175

Gln Asp Ala Leu Glu Thr Ala Arg Gln Arg Gly Ile Glu Leu Ile Val
            180                 185                 190

Val Asn Pro Val Leu Val Leu Gly Pro Leu Leu Gln Pro Thr Val Asn
        195                 200                 205

Ala Ser Thr Glu His Val Met Lys Tyr Leu Thr Gly Ser Ala Lys Thr
    210                 215                 220

Tyr Val Asn Ala Ala Gln Ala Tyr Val His Val Lys Asp Val Ala Glu
225                 230                 235                 240

Ala His Val Arg Val Tyr Glu Ala Pro Gly Ala His Gly Arg Tyr Ile
                245                 250                 255

Cys Ala Glu Gly Thr Thr Leu His Arg Gly Glu Leu Cys Arg Val Leu
            260                 265                 270

Cys Lys Leu Phe Pro Glu Tyr Pro Val Pro Thr Lys Cys Lys Asp Glu
        275                 280                 285

Val Asn Pro Pro Val Lys Gly Tyr Lys Phe Thr Asn Gln Arg Leu Lys
```

```
                290             295             300
Asp Leu Gly Met Glu Phe Val Pro Val Leu Gln Ser Ile Tyr Glu Thr
305                 310                 315                 320

Val Lys Ser Leu Gln Glu Lys Gly Met Leu Pro Val Leu Pro Pro Gly
                325                 330                 335

Asp Asp Val Arg Asp Asn Leu His Glu Gln Leu Met Met Lys Pro Ala
                340                 345                 350

Gln Leu Leu Arg Asn
            355

<210> SEQ ID NO 36
<211> LENGTH: 332
<212> TYPE: PRT
<213> ORGANISM: Lycopersicon esculentum

<400> SEQUENCE: 36

Met Pro Ser Glu Ser Gly Lys Val Val Cys Val Thr Gly Ala Gly Gly
1               5                   10                  15

Phe Ile Ala Ser Trp Leu Val Lys Leu Leu Glu Lys Gly Tyr Thr
            20                  25                  30

Val Arg Gly Thr Val Arg Asn Pro Asp Asp Ser Lys Asn Gly His Leu
        35                  40                  45

Lys Glu Leu Glu Gly Ala Lys Glu Arg Leu Ile Leu Arg Ala Asp
    50                  55                  60

Leu Leu Asp Tyr Gln Ser Leu Arg Glu Ala Ile Tyr Gly Cys Asp Gly
65                  70                  75                  80

Val Phe His Thr Ala Ser Pro Val Thr Asp Asp Pro Glu Gln Met Val
                85                  90                  95

Glu Pro Ala Val Ile Gly Thr Lys Asn Val Ile Thr Ala Ala Ala Glu
            100                 105                 110

Thr Lys Val Arg Arg Val Val Phe Thr Ser Ser Ile Gly Thr Val Tyr
        115                 120                 125

Met Asp Pro Asn Arg Ala Pro Asp Lys Val Val Asp Glu Thr Cys Trp
130                 135                 140

Ser Asp Leu Asp Tyr Cys Lys Asn Thr Lys Asn Trp Tyr Cys Tyr Gly
145                 150                 155                 160

Lys Thr Val Ala Glu Lys Thr Ala Arg Asp Glu Ala Arg Glu Lys Gly
                165                 170                 175

Val Asp Leu Val Val Ile Asn Pro Val Leu Val Leu Gly Pro Leu Leu
            180                 185                 190

Gln Pro Thr Val Asn Ala Ser Val Leu His Ile Leu Lys Tyr Leu Thr
        195                 200                 205

Gly Ser Ala Lys Thr Tyr Ala Asn Ser Ile Gln Ala Tyr Val His Val
210                 215                 220

Lys Asp Val Ala Leu Ala His Ile Leu Leu Tyr Glu Ala Pro Ser Ala
225                 230                 235                 240

Ser Gly Arg Tyr Ile Cys Ala Glu Arg Val Leu His Arg Gly Asp Val
                245                 250                 255

Val Glu Ile Leu Ala Lys Phe Phe Pro Glu Tyr Pro Ile Pro Thr Lys
            260                 265                 270

Cys Ser Asp Glu Thr Arg Pro Arg Ala Lys Pro Tyr Ile Phe Thr Asn
        275                 280                 285

Gln Lys Leu Lys Asp Leu Gly Leu Glu Phe Thr Pro Val Lys Gln Cys
290                 295                 300

Leu Tyr Glu Thr Val Lys Ser Leu Gln Glu Lys Gly His Leu Pro Val
```

```
                305                 310                 315                 320

Pro Thr Gln Asn Asp Glu Pro Ile Lys Ile His Ser
                325                 330

<210> SEQ ID NO 37
<211> LENGTH: 332
<212> TYPE: PRT
<213> ORGANISM: Solanum tuberosum

<400> SEQUENCE: 37

Met Pro Ser Glu Ser Gly Lys Val Val Cys Val Thr Gly Ala Gly Gly
1               5                   10                  15

Phe Ile Ala Ser Trp Leu Val Lys Leu Leu Glu Lys Gly Tyr Thr
                20                  25                  30

Val Arg Gly Thr Val Arg Asn Pro Asp Asp Pro Lys Asn Gly His Leu
            35                  40                  45

Lys Glu Leu Glu Gly Ala Lys Glu Arg Leu Ile Leu Leu Arg Ala Asp
        50                  55                  60

Leu Leu Asp Tyr Gln Ser Leu Arg Glu Ala Ile Tyr Gly Cys Asp Gly
65                  70                  75                  80

Val Phe His Thr Ala Ser Pro Val Thr Asp Asp Pro Glu Gln Met Val
                85                  90                  95

Glu Pro Ala Val Ile Gly Thr Lys Asn Val Ile Thr Ala Ala Ala Glu
            100                 105                 110

Ala Lys Val Gly Arg Val Val Phe Thr Ser Ser Ile Gly Thr Val Tyr
        115                 120                 125

Met Asp Pro Asn Arg Ala Pro Asp Lys Val Val Asp Glu Thr Cys Trp
130                 135                 140

Ser Asp Leu Gly Phe Cys Lys Asn Thr Lys Asn Trp Tyr Cys Tyr Gly
145                 150                 155                 160

Lys Thr Val Ala Glu Lys Thr Ala Trp Asp Glu Ala Arg Glu Lys Gly
                165                 170                 175

Val Asp Leu Val Val Ile Asn Pro Val Leu Val Leu Gly Pro Leu Leu
            180                 185                 190

Gln Pro Thr Val Asn Ala Ser Val Leu His Ile Leu Lys Tyr Leu Thr
        195                 200                 205

Gly Ser Ala Lys Thr Tyr Ala Asn Ser Ile Gln Ala Tyr Val His Val
210                 215                 220

Lys Asp Val Ala Leu Ala His Ile Leu Leu Tyr Glu Ala Pro Ser Ala
225                 230                 235                 240

Ser Gly Arg Tyr Ile Cys Ala Glu Ser Val Leu His Arg Gly Asp Val
                245                 250                 255

Val Glu Ile Leu Ala Lys Phe Phe Pro Glu Tyr Pro Ile Pro Thr Lys
            260                 265                 270

Cys Ser Asp Glu Thr Arg Pro Arg Ala Lys Pro Tyr Lys Phe Thr Asn
        275                 280                 285

Gln Lys Leu Lys Asp Leu Gly Leu Gly Phe Thr Pro Val Lys Gln Cys
    290                 295                 300

Leu Tyr Glu Thr Val Lys Ser Leu Gln Glu Lys Gly His Leu Pro Ile
305                 310                 315                 320

Pro Thr Gln Asn Asp Glu Pro Ile Lys Ile His Ser
                325                 330

<210> SEQ ID NO 38
<211> LENGTH: 327
<212> TYPE: PRT
```

<213> ORGANISM: Eucalyptus gunnii

<400> SEQUENCE: 38

Met Ser Ala Ala Gly Ala Gly Lys Val Cys Val Thr Gly Ala
1               5                   10                  15

Ser Arg Tyr Ile Ala Ser Trp Leu Val Lys Leu Leu Gln Arg Gly
            20                  25                  30

Tyr Thr Val Lys Ala Ser Val Arg Asp Pro Asn Asp Pro Lys Lys Thr
                35                  40                  45

Glu His Leu Leu Gly Leu Asp Gly Ala Lys Asp Arg Leu Gln Leu Phe
    50                  55                  60

Lys Ala Asn Leu Leu Glu Glu Gly Ser Phe Asp Pro Ile Val Glu Gly
65                  70                  75                  80

Cys Ala Gly Val Phe His Thr Ala Ser Pro Phe Tyr His Asp Val Lys
                85                  90                  95

Asp Pro Gln Ala Glu Leu Leu Asp Pro Ala Val Lys Gly Thr Leu Asn
            100                 105                 110

Val Leu Lys Ser Cys Ser Lys Ala Pro Ser Leu Gln Arg Val Val Leu
        115                 120                 125

Thr Ser Ser Met Ala Ala Val Ala Tyr Asn Arg Gln Pro Arg Thr Pro
130                 135                 140

Glu Val Val Asp Glu Ser Trp Phe Ser Asp Pro Asp Leu Cys Arg
145                 150                 155                 160

Gln Thr Asn Ala Trp Tyr Val Leu Ser Lys Thr Leu Ala Glu Asp Ala
                165                 170                 175

Ala Trp Lys Phe Val Lys Glu Lys Gly Ile Asp Met Val Thr Ile Asn
            180                 185                 190

Pro Ala Met Val Ile Gly Pro Leu Leu Gln Pro Thr Leu Asn Thr Ser
        195                 200                 205

Ala Ala Ala Ile Gly Asn Leu Ile Asn Gly Ala Pro Thr Phe Pro Asn
210                 215                 220

Ala Ser Phe Gly Trp Val Asn Val Lys Asp Val Ala Asn Ala His Ile
225                 230                 235                 240

Leu Ala Phe Glu Val Pro Ser Ala Ser Gly Arg Tyr Cys Leu Val Glu
                245                 250                 255

Arg Ile Ala His Tyr Ser Glu Ile Val Arg Ile Leu Arg Glu Leu Tyr
            260                 265                 270

Pro Ser Ala Gln Leu Pro Glu Lys Ser Ala Asp Asp Lys Pro Phe Val
        275                 280                 285

Pro Ile Tyr Gln Val Ser Lys Glu Lys Val Lys Ser Leu Gly Ile Asn
        290                 295                 300

Tyr Ile Pro Leu Glu Gln Asn Leu Lys Glu Thr Val Glu Ser Leu Lys
305                 310                 315                 320

Glu Lys Gly Phe Val Lys Phe
                325

<210> SEQ ID NO 39
<211> LENGTH: 327
<212> TYPE: PRT
<213> ORGANISM: Nicotiana tabacum

<400> SEQUENCE: 39

Met Ser Leu Ala Ala Lys Thr Val Cys Val Thr Gly Ala Ser Gly Tyr
1               5                   10                  15

Ile Ala Ser Trp Leu Val Lys Phe Leu Leu Gln Arg Gly Tyr Thr Val
            20                  25                  30

```
Lys Ala Ser Val Arg Asp Pro Asn Asp Pro Lys Lys Thr Gln His Leu
             35                  40                  45

Leu Ser Leu Gly Gly Gly Ala Glu Arg Leu His Leu Phe Lys Ala Asn
 50                  55                  60

Leu Leu Glu Glu Gly Ser Phe Asp Ala Val Val Asp Gly Tyr Glu Gly
 65                  70                  75                  80

Val Phe His Thr Ala Ser Pro Phe Pro Tyr Ser Val Thr Asp Pro Gln
                 85                  90                  95

Ala Glu Leu Leu Ala Pro Ala Val Lys Gly Thr Leu Asn Leu Leu Gly
                100                 105                 110

Ser Cys Ala Lys Ala Pro Ser Val Lys Arg Val Val Leu Thr Ser Ser
                115                 120                 125

Ile Ala Val Ala Tyr Ser Gly Gln Pro Arg Thr Pro Glu Val Val Val
            130                 135                 140

Asp Glu Ser Trp Trp Thr Ser Pro Asp Tyr Cys Arg Glu Lys Gln Leu
145                 150                 155                 160

Trp Tyr Val Leu Ser Lys Thr Leu Ala Glu Asp Ala Ala Trp Lys Phe
                165                 170                 175

Val Lys Glu Lys Gly Ile Asp Met Val Ala Ile Asn Pro Ala Met Val
                180                 185                 190

Ile Gly Pro Leu Leu Gln Pro Thr Leu Asn Thr Ser Ser Gly Ala Val
            195                 200                 205

Leu Asn Leu Val Asn Gly Ala Glu Thr Tyr Pro Asn Ser Thr Phe Gly
            210                 215                 220

Trp Val Asn Val Lys Asp Val Ala Asn Ala His Ile Leu Ala Phe Glu
225                 230                 235                 240

Asn Pro Ser Ala Asn Gly Arg Tyr Leu Met Val Glu Arg Val Ala His
                245                 250                 255

Tyr Ser Asp Ile Leu Lys Ile Leu Arg Asp Leu Tyr Pro Thr Met Arg
                260                 265                 270

Leu Pro Glu Lys Cys Ala Asp Asp Asn Pro Leu Met Gln Asn Tyr Gln
            275                 280                 285

Val Ser Lys Glu Arg Ala Lys Ser Leu Gly Val Glu Phe Thr Pro Leu
            290                 295                 300

Glu Glu Ser Ile Lys Glu Thr Val Glu Ser Leu Lys Gly Lys Arg Phe
305                 310                 315                 320

Phe Gly Gly Ser Ser Ala Met
                325

<210> SEQ ID NO 40
<211> LENGTH: 323
<212> TYPE: PRT
<213> ORGANISM: Nicotiana tabacum

<400> SEQUENCE: 40

Met Ala Thr Lys Thr Val Cys Val Thr Gly Ser Ser Gly Tyr Ile Ala
1               5                  10                  15

Ser Trp Leu Val Lys Phe Leu Leu Gln Arg Gly Tyr Thr Val Lys Ala
            20                  25                  30

Thr Val Arg Asp Pro Ser Asp Pro Lys Lys Thr Asp His Leu His Ser
             35                  40                  45

Leu Ser Gly Ala Lys Glu Arg Leu His Leu Phe Lys Ala Asn Leu Leu
 50                  55                  60

Glu Glu Gly Ala Phe Asp Ala Val Val Asp Gly Cys Glu Gly Val Phe
 65                  70                  75                  80
```

```
His Thr Ala Ser Pro Phe Tyr His Gly Val Lys Asp Pro Gln Ala Glu
                85                  90                  95

Leu Ile Asp Pro Ala Leu Lys Gly Thr Leu Asn Val Leu Gly Ser Val
            100                 105                 110

Ala Lys Thr Pro Ser Ile Arg Arg Val Leu Thr Ser Ser Val Ala
        115                 120                 125

Ala Val Ala Phe Asn Gly Lys Pro Arg Thr Pro Glu Val Val Val Asp
        130                 135                 140

Glu Thr Trp Gly Ser Asp Pro Asp Phe Cys Arg Glu Ser Gln Leu Trp
145                 150                 155                 160

Tyr Val Leu Ser Lys Thr Leu Ala Glu Asp Ala Ala Trp Lys Phe Val
                165                 170                 175

Lys Glu Lys Ala Ile Asp Met Val Thr Ile Asn Pro Ala Met Val Ile
                180                 185                 190

Gly Gly Leu Leu Gln Pro Ile Leu Asn Thr Ser Cys Ala Ala Val Leu
                195                 200                 205

Gln Leu Ile Asn Gly Ala Glu Thr Tyr Pro Asn Ala Thr Leu Gly Trp
            210                 215                 220

Val Asn Val Lys Asp Val Ala Leu Ala His Ile Leu Ala Phe Glu Asn
225                 230                 235                 240

Pro Ser Ala Asn Gly Arg Tyr Leu Met Val Glu Ala Val Ala His Tyr
                245                 250                 255

Ser Glu Leu Val Lys Ile Leu Arg Glu His Tyr Pro Thr Met Lys Leu
                260                 265                 270

Pro Glu Lys Cys Val Asp Asp Lys Pro Phe Pro Pro Lys Tyr Gln Val
            275                 280                 285

Asn Ile Glu Arg Ala Lys Gln Leu Gly Val Glu Phe Thr Pro Leu Ala
        290                 295                 300

Glu Ser Ile Lys Glu Thr Val Glu Ser Leu Lys Glu Lys Lys Phe Tyr
305                 310                 315                 320

Ser Asp Ala

<210> SEQ ID NO 41
<211> LENGTH: 520
<212> TYPE: PRT
<213> ORGANISM: Arabidopsis thaliana

<400> SEQUENCE: 41

Met Glu Ser Ser Ile Ser Gln Thr Leu Ser Lys Leu Ser Asp Pro Thr
1               5                   10                  15

Thr Ser Leu Val Ile Val Val Ser Leu Phe Ile Phe Ile Ser Phe Ile
            20                  25                  30

Thr Arg Arg Arg Arg Pro Pro Tyr Pro Pro Gly Pro Arg Gly Trp Pro
        35                  40                  45

Ile Ile Gly Asn Met Leu Met Met Asp Gln Leu Thr His Arg Gly Leu
        50                  55                  60

Ala Asn Leu Ala Lys Lys Tyr Gly Gly Leu Cys His Leu Arg Met Gly
65                  70                  75                  80

Phe Leu His Met Tyr Ala Val Ser Ser Pro Glu Val Ala Arg Gln Val
                85                  90                  95

Leu Gln Val Gln Asp Ser Val Phe Ser Asn Arg Pro Ala Thr Ile Ala
            100                 105                 110

Ile Ser Tyr Leu Thr Tyr Asp Arg Ala Asp Met Ala Phe Ala His Tyr
        115                 120                 125
```

```
Gly Pro Phe Trp Arg Gln Met Arg Lys Val Cys Val Met Lys Val Phe
            130                 135                 140

Ser Arg Lys Arg Ala Glu Ser Trp Ala Ser Val Arg Asp Glu Val Asp
145                 150                 155                 160

Lys Met Val Arg Ser Val Ser Cys Asn Val Gly Lys Pro Ile Asn Val
                165                 170                 175

Gly Glu Gln Ile Phe Ala Leu Thr Arg Asn Ile Thr Tyr Arg Ala Ala
            180                 185                 190

Phe Gly Ser Ala Cys Glu Lys Gly Gln Asp Glu Phe Ile Arg Ile Leu
        195                 200                 205

Gln Glu Phe Ser Lys Leu Phe Gly Ala Phe Asn Val Ala Asp Phe Ile
210                 215                 220

Pro Tyr Phe Gly Trp Ile Asp Pro Gln Gly Ile Asn Lys Arg Leu Val
225                 230                 235                 240

Lys Ala Arg Asn Asp Leu Asp Gly Phe Ile Asp Ile Ile Asp Glu
                245                 250                 255

His Met Lys Lys Lys Glu Asn Gln Asn Ala Val Asp Gly Asp Val
        260                 265                 270

Val Asp Thr Asp Met Val Asp Asp Leu Leu Ala Phe Tyr Ser Glu Glu
        275                 280                 285

Ala Lys Leu Val Ser Glu Thr Ala Asp Leu Gln Asn Ser Ile Lys Leu
290                 295                 300

Thr Arg Asp Asn Ile Lys Ala Ile Ile Met Asp Val Met Phe Gly Gly
305                 310                 315                 320

Thr Glu Thr Val Ala Ser Ala Ile Glu Trp Ala Leu Thr Glu Leu Leu
                325                 330                 335

Arg Ser Pro Glu Asp Leu Lys Arg Val Gln Gln Glu Leu Ala Glu Val
            340                 345                 350

Val Gly Leu Asp Arg Arg Val Glu Glu Ser Asp Ile Glu Lys Leu Thr
        355                 360                 365

Tyr Leu Lys Cys Thr Leu Lys Glu Thr Leu Arg Met His Pro Pro Ile
370                 375                 380

Pro Leu Leu Leu His Glu Thr Ala Glu Asp Thr Ser Ile Asp Gly Phe
385                 390                 395                 400

Phe Ile Pro Lys Lys Ser Arg Val Met Ile Asn Ala Phe Ala Ile Gly
                405                 410                 415

Arg Asp Pro Thr Ser Trp Thr Asp Pro Asp Thr Phe Arg Pro Ser Arg
            420                 425                 430

Phe Leu Glu Pro Gly Val Pro Asp Phe Lys Gly Ser Asn Phe Glu Phe
        435                 440                 445

Ile Pro Phe Gly Ser Gly Arg Arg Ser Cys Pro Gly Met Gln Leu Gly
450                 455                 460

Leu Tyr Ala Leu Asp Leu Ala Val Ala His Ile Leu His Cys Phe Thr
465                 470                 475                 480

Trp Lys Leu Pro Asp Gly Met Lys Pro Ser Glu Leu Asp Met Asn Asp
                485                 490                 495

Val Phe Gly Leu Thr Ala Pro Lys Ala Thr Arg Leu Phe Ala Val Pro
            500                 505                 510

Thr Thr Arg Leu Ile Cys Ala Leu
            515                 520

<210> SEQ ID NO 42
<211> LENGTH: 521
<212> TYPE: PRT
<213> ORGANISM: Lycopersicon esculentum
```

```
<400> SEQUENCE: 42

Met Val Leu Asn Asn Ile Asn Ser Ile Leu Glu Ala Leu Gln Ala Asn
1               5                   10                  15

Pro Ile Leu Ile Phe Phe Phe Ile Ile Pro Leu Phe Phe Leu Tyr Leu
            20                  25                  30

Phe Ser Thr Ser Arg Arg Lys Arg Tyr Pro Pro Gly Pro Leu Gly Trp
        35                  40                  45

Pro Leu Ile Gly Asn Met Met Ile Met Asp Gln Leu Thr His Arg Gly
    50                  55                  60

Leu Ala Lys Leu Ala Gln Lys Tyr Gly Val Phe His Leu Lys Met
65                  70                  75                  80

Gly Tyr Val His Lys Ile Val Ile Ser Gly Pro Glu Glu Ala Arg Gln
                85                  90                  95

Val Leu Gln Val Gln Asp Asn Ile Tyr Ser Asn Arg Pro Lys Thr Val
            100                 105                 110

Ala Ile Ser Tyr Leu Thr Tyr Asp Arg Ala Asp Met Ala Phe Ala Asp
        115                 120                 125

Tyr Gly Pro Phe Trp Arg Gln Met Arg Lys Leu Cys Val Met Lys Leu
    130                 135                 140

Phe Ser Arg Lys Arg Ala Glu Ser Trp Asp Ser Val Arg Asp Glu Val
145                 150                 155                 160

Asp Ser Met Val Lys Ile Val Thr Thr Asn Ala Gly Thr Ser Ile Asn
                165                 170                 175

Leu Gly Glu Leu Val Phe Cys Leu Thr Arg Asn Ile Ile Tyr Arg Ala
            180                 185                 190

Ala Phe Gly Thr Ser Ser Asp Glu Gly Gln Asp Asp Phe Ile Lys Ile
        195                 200                 205

Leu Gln Glu Phe Ser Lys Leu Phe Gly Ala Phe Asn Met Ala Asp Phe
    210                 215                 220

Ile Pro Trp Leu Gly Trp Ile Gly Lys Gln Gly Leu Asn Val Arg Leu
225                 230                 235                 240

Ala Lys Ala Arg Ala Ser Leu Asp Gly Phe Ile Asp Thr Ile Ile Asp
                245                 250                 255

Asp His Ile Glu Arg Lys Lys Ala Ile His Val Ile Asn Asp Asp Gly
            260                 265                 270

Tyr Arg Glu Ser Asp Met Val Asp Glu Leu Leu Ala Phe Tyr Ser Glu
        275                 280                 285

Glu Thr Lys Val Asn Glu Ser Glu Asp Leu Gln Asn Ala Ile Arg Leu
    290                 295                 300

Thr Arg Asp Asn Ile Lys Ala Ile Ile Met Asp Val Met Phe Gly Gly
305                 310                 315                 320

Thr Glu Thr Val Ala Ser Ala Ile Glu Trp Ala Met Ala Glu Leu Met
                325                 330                 335

Lys Ser Pro Glu Asp Leu Lys Lys Val Gln Gln Glu Leu Ala Asn Val
            340                 345                 350

Val Gly Leu Asn Arg Lys Val Asp Glu Ser Asp Phe Glu Asn Leu Thr
        355                 360                 365

Tyr Leu Lys Cys Cys Leu Lys Glu Thr Leu Arg Leu His Pro Pro Ile
    370                 375                 380

Pro Leu Leu Leu His Glu Thr Ala Glu Ser Thr Val Ser Gly Tyr
385                 390                 395                 400

Tyr Ile Pro Ala Asn Ser His Val Ile Ile Asn Ser Phe Ala Ile Gly
                405                 410                 415
```

-continued

```
Arg Asp Lys Asn Ser Trp Glu Asp Pro Asp Ser Phe Lys Pro Ser Arg
            420                 425                 430

Phe Leu Lys Glu Gly Val Ala Asp Phe Lys Gly Gly Asn Phe Glu Phe
            435                 440                 445

Leu Pro Phe Gly Ser Gly Arg Arg Ser Cys Pro Gly Met Gln Leu Gly
        450                 455                 460

Leu Tyr Ala Leu Glu Met Ala Val Ala His Leu Leu His Cys Phe Thr
465                 470                 475                 480

Trp Glu Leu Pro Asp Gly Met Lys Pro Ser Glu Leu Asn Met Asp Asp
                485                 490                 495

Met Phe Gly Leu Thr Ala Pro Leu Ala Asn Arg Leu Val Ala Val Pro
            500                 505                 510

Thr Pro Arg Leu Leu Cys Glu Ile Tyr
            515                 520
```

POLYNUCLEOTIDES ENCODING LIGNIN BIOSYNTHETIC PATHWAY ENZYMES IN COFFEE

This is a U.S. National Application of International Application No. PCT/US06/040223, filed Oct. 16, 2006, which claims benefit of U.S. Provisional Application No. 60/726,812, filed Oct. 14, 2005, the entire contents of each of which are incorporated by reference herein.

FIELD OF THE INVENTION

The present invention relates to the field of agricultural biotechnology. In particular, the invention features polynucleotides from coffee plants that encode enzymes responsible for lignin synthesis, as well as methods for using these polynucleotides and polypeptides for gene regulation and manipulation of flavor, aroma and other features of coffee beans.

BACKGROUND OF THE INVENTION

Various publications, including patents, published applications and scholarly articles, are cited throughout the specification. Each of these publications is incorporated by reference herein, in its entirety. Citations not fully set forth within the specification may be found at the end of the specification.

Coffee aroma and flavor are key components in consumer preference for coffee varieties and brands. The characteristic aroma and flavor of coffee stems from a complex series of chemical reactions involving flavor precursors (Maillard reactions) that occur during the roasting of the bean. Flavor precursors include chemical compounds and biomolecules present in the green coffee bean. To date, over 800 chemicals and biomolecules have been identified as contributing to coffee flavor and aroma. (Flament, I., 2002 "Coffee Flavor Chemistry" J. Wiley U.K.). Because coffee consumers are becoming increasingly sophisticated, it is desirable to produce coffee with improved aroma and flavor in order to meet consumer preferences. Both aroma and flavor may be artificially imparted into coffee products through chemical means. See, for example, U.S. Pat. No. 4,072,761 (aroma) and U.S. Pat. No. 3,962,321 (flavor). However, to date, there is little information concerning the influence of natural coffee grain components such as polysaccharides, proteins, pigments, and lipids, on coffee aroma and flavor. One approach is to select varieties from the existing germplasm that have superior flavor characteristics. A disadvantage to this approach is that, frequently, the highest quality varieties also possess significant negative agronomics traits, such as poor yield and low resistance to diseases and environmental stresses. It is also possible to select new varieties from breeding trials in which varieties with different industrial and agronomic traits are crossed and their progeny are screened for both high quality and good agronomic performance. However, this latter approach is very time consuming, with one crossing experiment and selection over three growing seasons talking a minimum of 7-8 years. Thus, an alternative approach to enhancing coffee quality would be to use techniques of molecular biology to enhance those elements responsible for the flavor and aroma that are naturally found in the coffee bean, or to add aroma and flavor-enhancing elements that do not naturally occur in coffee beans. Genetic engineering is particularly suited to achieve these ends. For example, coffee proteins from different coffee species may be swapped. In the alternative, the expression of genes encoding naturally occurring coffee proteins that positively contribute to coffee flavor may be enhanced. Conversely, the expression of genes encoding naturally occurring coffee proteins that negatively contribute to coffee flavor may be suppressed.

Coffees from different varieties and origins exhibit significant flavor and aroma quality variations when the green grain samples are roasted and processed in the same manner. The quality differences are a manifestation of chemical and physical variations within the grain samples that result mainly from differences in growing and processing conditions, and also from differences in the genetic background of both the maternal plant and the grain. At the level of chemical composition, at least part of the flavor quality can be associated with variations in the levels of small metabolites, such as sugars, acids, phenolics, and caffeine found associated with grain from different varieties. It is accepted that there are other less well characterized flavor and flavor-precursor molecules. In addition, it is likely that structural variations within the grain also contribute to differences in coffee quality. One approach to finding new components in the coffee grain linked to coffee quality is to study the genes and proteins differentially expressed during the maturation of grain samples in different varieties that possess different quality characteristics. Similarly, genes and proteins that participate in the biosynthesis of flavor and flavor-precursor molecules may be studied.

Lignin is a phenolic polymeric material, which in angiosperms is primarily composed of three phenylpropanoid pathway-derived compounds: p-coumaroyl alcohol, coniferyl alcohol and sinapyl alcohol, i.e., the major monolignols found in plant (Hatfield R et al. 2001). These monolignols produce respectively p-hydroxyphenyl H, guaiacyl G, and syringyl S units when incorporated into the lignin polymer. Although exceptions exist, in a dicotyledonous angiosperm such as coffee, lignins consist principally of G and S units with traces of H units (Boerjan W et al. 2003). These complex polymers contribute compressive strength and increased water impermeability of the extracellular cell wall polysaccharide-protein matrix (Whetten R W et al. 1998). One response to pathogen ingression in plants is to increase the production of lignins in the cell wall, thereby reinforcing the cells surrounding the infection site and restricting further pathogen growth. (Vance C et al. 1980). Furthermore, other types of stresses, such as elevated levels of $H_2O_2$ and reduced cellulose synthesis, also result in an increased production of lignin, indicating that elevation of lignin synthesis is part of the more general stress response system in plants. (Wu G et al. 1997; and Logemann E et al. 1997).

The biosynthetic pathway for the monolignols has been controversial, with the model for the pathway changing several times in recent years (Dixon R A et al. 2001; and, Humphreys J M et al. 2002). The synthesis of lignin monomers, which is part of phenylpropanoid metabolism, begins with the deamination of phenylalanine, continues with successive hydroxylation and methylation reactions on the aromatic ring, and ends with the conversion of the side-chain carboxyl to an alcohol group (Boerjan et al. 2003). As shown in FIG. 1, the enzyme 4-hydroxycinnamoyl-CoA ligase (4CL) catalyzes an early reaction in the pathway to monolignol synthesis, the formation of the CoA esters caffeoyl-CoA, feruloyl CoA, and 5-hydroxy-feruloyl CoA (Lee et al. 1997). cDNA encoding this protein have recently been obtained and characterized from coffee, see WO 2007/044992, claiming priority to U.S. Provisional Application No. 60/726,298.

In angiosperms species, the first lignol specific enzyme identified was caffeic acid O-methyltransferase (COMT). COMT is capable of converting caffeic acid to ferulic acid, as well as converting 5-hydroxyferulic acid to sinapic acid.

(Dixon et al. 2001). Down regulation of the COMT gene in maize (*Zea mays*) has been shown to cause a significant reduction of COMT activity (a fall of 70 to 85%), resulting in modification of lignin content and composition, and indicates that this enzyme is a key enzyme for lignin synthesis. (Piquemal J et al. 2002). Recently, the 2.2-Å crystal structure of an alfalfa COMT protein complexed with the cofactor SAH (S-adenosyl-L-homocysteine) and the substrate ferulic acid has been accomplished by Zubieta et al. (2002). This has allowed for the development of a model to explain the catalytic mechanism of COMT. This model indicates that the 3- or 5-hydroxyl group can be deprotonated by His269, facilitating the transfer of the reactive methyl group of SAM. The crystal structure of the alfalfa COMT also indicated specific residues that, a) interact in SAM recognition, b) are involved in substrate recognition, and c) are involved in various aspects of the catalytic reaction (Zubieta et al. 2002).

Ferulic acid generated by COMT can be hydroxylated by ferulate 5 hydroxylase (F5H), which is a cytochrome P450-dependent monooxygenase, to form 5-hydroxy-ferulic acid. F5H is also capable of hydroxylating coniferaldehyde and coniferyl alcohol forming 5-hydroxy-coniferaldehyde and 5-hydroxy-coniferyl alcohol respectively (Meyer K et al. 1996). F5H is believed to be potentially a rate limiting step in syringyl lignin biosynthesis, a proposal supported by the observation that an *Arabidopsis* mutant deficient in F5H expression is also affected at the level of sinapate esters accumulation in siliques and seeds (Ruegger M et al. 1999). All the products of F5H are also substrates for a second O-methylation catalyzed by COMT1 (FIG. 1).

CCoAOMT is a bifunctional enzyme which converts caffeoyl CoA to feruloyl CoA and 5-hydroxy-feruloyl CoA to sinapyl CoA (Inoue et al. 1998), and a CcOAOMT has been directly shown to be involved in lignin biosynthesis in the differential tracheary elements of *Zinnia elegans* (Ye et al. 1995). cDNA encoding CCoAOMT proteins have also been isolated and characterized from coffee, see WO 2007/044992, claiming priority to U.S. Provisional Application No. 60/726,298.

Another enzyme specifically involved in lignol biosynthesis is cinnamoyl-CoA reductase (CCR), and this enzyme catalyzes the conversion of feruloyl CoA and 5-hydroxy-feruloyl CoA into coniferaldehyde and 5-hydroxy-coniferaldehyde respectively, leading directly into the biosynthesis of G (coniferaldehyde) and S (5-hydroxy-coniferaldehyde) lignin units (Ma et al. 2005). In tobacco, down regulation of the CCR gene using an antisense construct generated plants with abnormal development and reduced growth, as well as abnormal leaf morphology and collapsed vessels. There was also an associated reduction in the level of G lignin compounds (Ralph J et al. 1998). One of the last enzymes involved in the monolignol pathway is cinnamyl alcohol dehydrogenase (CAD), which catalyzes the NADPH dependent conversion of coniferaldehyde, 5-hydroxy-coniferaldehyde and sinapaldehyde to the corresponding alcohols (Kim S J et al. 2004). In *Arabidopsis*, single mutants of the CAD genes AtCAD-C and AtCAD-D were found to have lower CAD activities, while a the double mutant obtained by crossing the two mutants had a 40% decrease in stem lignin content, demonstrating that these are the main CAD genes involved in stem lignin synthesis (Sibout R et al. 2005). This latter data indicates that altering a late step in lignol synthesis (i.e., altered CAD expression/activity), can be useful to influence the types of lignin generated, as well as the quantity of lignin formed.

There is little information in the literature concerning the levels of lignin in mature green coffee grain. Previously, it has been suggested that coffee grain had a lignin content of approximately 5% (Dart, S. and Nursten, H. 1985 Volatile components. In Coffee, Volumne 1; Chemistry, ed Clarke, R. and Macrae, R. Elsevier Applied Science, London, p 223-265). More recently, a compositional analysis of green grain has indicated that the carbohydrates, fat and protein made up 72% of the grain, leaving 28% of the grain corresponding to chlorogenic acids, minerals, lignin, amino acids, trigonelline, caffeine, and other compounds (Oosterveld, A., Harmsen, J., Voragen, A. and Schols, H. 2003 Extraction and characterization of polysaccharides from green and roasted *C. arabica* beans. Carbohydrate Polymers, 52, 285-296). From this latter data, it can be estimated that approximately 5-8% of the green grain is lignin. Other evidence for presence of significant amounts of lignin in the secondary cell walls of coffee grain cells was obtained by several different staining techniques and the use of light and transmission electron microscopy (Dentan, E. 1985. The microscopic structure of the coffee bean. In Coffee botany, biochemistry, and production of beans and beverage. Eds Clifford, M. and Willson, K. Croom Helm, London).

The lignin of the coffee grain is presumably involved in the maintenance of cellular structure, especially in the secondary cell walls of the grain, and likely also contributes to stress and insect resistance. In addition to being important for the overall health and structure of the coffee grain, it is likely that coffee grain quality can be influenced by the quantity, type, and structure of the lignin present. Lignin monomers and polymers may be directly involved in some of the chemical reactions that form coffee aromas/flavors and those that cause protein and polysaccharide degradation in the green coffee grain during coffee roasting. For example, lignin is believed to be a participant in the Maillard reaction, and potentially contributes to the generation of phenylpropanoid-derived aroma molecules such as guaiacol and 4-vinyl guaiacol. (Yeretzian C et al. 2002; and Logmann; Sagehashi, M. Miyasaka, N. Shishido, H., and Sakoda, A. 2005, Bioresource Technol. in press).

Lignins are also likely to be involved in melanoidin formation in coffee, and hence contribute to the overall antioxidant capability of this fraction. (Delgado-Andrade C et al. 2005). Lignin structure and/or quantity could also affect coffee quality indirectly by its influence on grain properties like water permeability and cell wall structure, thereby influencing, for example, the rate of water loss and the grain heating profile during coffee roasting, as well as the capability of the grain to trap volatile gases formed within the coffee endosperm during roasting (Yeretzian C et al. 2002).

Interestingly, it is believed that one or more coffee genes involved in lignin synthesis described herein is involved in the synthesis of coffee flavor molecules, or currently unknown flavor precursor molecules, in a similar fashion to that demonstrated recently in strawberry. Strawberries contain an unusual group of aroma compounds related to 2,5-dimethyl-3(2H)-furanone (DMMF). This particular compound is generated from 2,5-dimethyl-4-hydroxy-3(2H)-furanone (DMHF) via an S-adenosyl-L-methionine dependent O-methyltransferase FaOMT with very high homology to the lignin synthesis enzyme COMT. The expression pattern of the FaOMT, and the enzymatic activity in the different stages of fruit ripening, suggests that FaOMT is also involved in lignin formation within the achenes and the vascular bundles of the expanding fruit, in addition to playing an important role in the biosynthesis of strawberry volatiles such as vanillin and DMMF (Weim et al. 2002).

Variety differences in lignin structure and/or quantity can also alter the extractability properties of the respective roasted grain. In maize, four brown mdrib (bm) mutants are known: bm1, which affects in CAD activity, bm2, which is associated with an over-expression of COMT, bin3a and 3b, which represent an insertion and a deletion in a COMT gene, respectively, and the bm4 mutant, which is affected in cell wall composition. Marita et al. (2003), showed that the double mutant bm1-bm2 had lower lignin content relative to the wild type. In addition, parallel reduction of esterified p-coumaroyl CoA was observed in all mutants. All observation were associated with alteration of cell wall degradability in the maize mutant (Marita J M et al. 2003).

Despite of the importance of lignin synthesis to the overall welfare of the coffee plant, as well as its probable impact on several aspects of coffee quality, at present there is no available information detailing lignin biosynthesis in coffee.

From the foregoing discussion, it will be appreciated that modulating lignin content in coffee grain by genetically modulating the production of the proteins responsible for lignin biosynthesis would be of great utility to enhance the aroma and flavor of coffee beverages and coffee products produced from such genetically engineered coffee beans. Modulating lignin content in the coffee plant also has implications for protecting the coffee plant and its fruit from pathogens, herbivores, and insects. Accordingly, a need exists to identify, isolate and utilize genes and enzymes from coffee that are involved in the biosynthesis of lignins. The present invention addresses this need.

SUMMARY OF THE INVENTION

The invention described herein features genes encoding enzymes in the lignin biosynthetic pathway in coffee plants, their encoded polypeptides, and methods for using these polynucleotides and polypeptides for gene regulation and manipulation of flavor, aroma and other features of coffee beans.

One aspect of the invention features a nucleic acid molecule isolated from coffee (*Coffea* spp.), having a coding sequence that encodes a lignin biosynthetic pathway enzyme. In one embodiment, the enzyme is a caffeic acid O-methyltransferase that is at least 75.4% identical to SEQ ID NO:15. In another embodiment, the enzyme is a caffeic acid O-methyltransferase that is at least 42% identical to SEQ ID NO:16. In another embodiment, the enzyme is a caffeic acid O-methyltransferase that is at least 48.1% identical to SEQ ID NO:17. In another embodiment, the enzyme is a caffeic acid O-methyltransferase that is at least 47.4% identical to SEQ ID NO:18. In another embodiment, the enzyme is a cinnamoyl CoA reductase that is at least 48.7% identical to SEQ ID NO:19. In another embodiment, the enzyme is a cinnamoyl CoA reductase that is at least 88.6% identical to SEQ ID NO:20. In another embodiment, the enzyme is a cinnamyl alcohol dehydrogenase that is at least 42.3% identical to SEQ ID NO:21. In another embodiment, the enzyme is a cinnamyl alcohol dehydrogenase that is at least 78.2% identical to SEQ ID NO:22. In another embodiment, the enzyme is a cinnamyl alcohol dehydrogenase that is at least 61.3% identical to SEQ ID NO:23. In another embodiment, the enzyme is a cinnamyl alcohol dehydrogenase that is at least 62.8% identical to SEQ ID NO:24. In another embodiment, the enzyme is a cinnamyl alcohol dehydrogenase that is at least 31.6% identical to SEQ ID NO:25. In another embodiment, the enzyme is a cinnamyl alcohol dehydrogenase that is at least 79.8% identical to SEQ ID NO:26. In another embodiment, the enzyme is a cinnamyl alcohol dehydrogenase that is at least 68% identical to SEQ ID NO:27. In another embodiment, the enzyme is a ferulate 5-hydroxylase that is at least 53% identical to SEQ ID NO:28.

In certain embodiments, the nucleic acid molecule is a gene having an open reading frame that comprises the coding sequence. Alternatively, it may comprise an mRNA molecule produced by transcription of that gene, or a cDNA molecule produced by reverse transcription of the mRNA molecule. The invention also features an oligonucleotide between 8 and 100 bases in length, which is complementary to a segment of the aforementioned nucleic acid molecule.

Another aspect of the invention features a vector comprising the above-described lignin biosynthetic pathway enzyme-encoding nucleic acid molecules. In certain embodiments, the vector is an expression vector selected from the group of vectors consisting of plasmid, phagemid, cosmid, baculovirus, bacmid, bacterial, yeast and viral vectors. In certain embodiments, the vector contains the coding sequence of the nucleic acid molecule operably linked to a constitutive promoter. In other embodiments, the coding sequence is operably linked to an inducible promoter. In other embodiments, the coding sequence of the nucleic acid molecule is operably linked to a tissue specific promoter, such as a seed specific promoter, preferably a coffee seed specific promoter.

According to another aspect of the invention, a host cell transformed with the aforementioned vector is provided. The host cell may be a plant, bacterial, fungal, insect or mammalian cell. In certain embodiments, the host cell is a plant cell selected from any one of coffee, tobacco, *Arabidopsis*, maize, wheat, rice, soybean barley, rye, oats, sorghum, alfalfa, clover, canola, safflower, sunflower, peanut, cacao, tomato tomatillo, potato, pepper, eggplant, sugar beet, carrot, cucumber, lettuce, pea, aster, begonia, chrysanthemum, delphinium, zinnia, and turfgrasses. The invention also features a fertile transgenic plant produced by regenerating the transformed plant cell. In a specific embodiment, the fertile transgenic plant is a *Coffea* species.

Another aspect of the invention features a method to modulate flavor or aroma of coffee beans. The method comprises modulating production of one or more lignin biosynthetic pathway enzymes within coffee seeds. In some embodiments, the method comprises increasing production of the one or more lignin biosynthetic pathway enzymes, e.g., by increasing expression of one or more endogenous lignin biosynthetic pathway enzyme-encoding genes within the coffee seeds, or by introducing a lignin biosynthetic pathway enzyme-encoding transgene into the plant. In other embodiments, the method comprises decreasing production of the one or more lignin biosynthetic pathway enzymes, e.g., by introducing a nucleic acid molecule into the coffee that inhibits the expression of one or more of the lignin biosynthetic pathway enzyme-encoding genes.

BRIEF DESCRIPTION OF THE DRAWINGS

FIG. 2. Protein sequence alignment of CcCOMT1, CcCOMT2p, CcCOMT3p and CcCOMT4p with plant COMT protein sequences. Alignment of putative proteins encoded by the CcCOMT genes with other COMT proteins available in the NCBI database was done using the CLUSTAL W program in the MegAlign software (Lasergene package, DNASTAR). Amino acids marked in grey match the amino acids most frequently found in this position. GenBank Accession Numbers are given in parentheses: CcCOMT IRD fruit (*Coffea canephora*, AAN03727) (SEQ ID NO: 29); CcCOMT IRD leaf (*Coffea canephora*, AAN03726) (SEQ ID NO: 30); MsCOMT (*Medicago sativa*, AAB46623) (SEQ ID NO: 31); NtCOMT (*Nicotiana tabacum*, AAL91506) (SEQ ID NO: 32); and ZeCOMT (*Zinnia elegans*, Q43239) (SEQ ID NO: 33). Green boxes indicate active site dimer; yellow boxes indicate catalytic residues; pink boxes show conserved residues and motifs for SAM binding; and blue boxes show active site substrate binding/positioning residues. All interactions and sites were characterized in crystal structure of alfalfa (*Medicago sativa*) COMT in complex with the reaction products (Zubieta et al. 2002).

FIG. 3. Protein sequence alignment of CcCCR1, and CcCCR2 with plant CCR protein sequences. Alignment of putative proteins encoded by the CcCCR genes with other CCR proteins available in the NCBI database was done using the CLUSTAL W program in the MegAlign software. Amino acids marked in grey match the amino acids most frequently found in this position. GenBank Accession Numbers are given in parentheses: EgCCR (*Eucalyptus gunnii*, T10735) (SEQ ID NO: 34); TaCCR (*Triticum aestivumna*, AAX08107) (SEQ ID NO: 35); LeCCR (*Lycopersicon esculentum*, AAY41880) (SEQ ID NO: 36); and StCCR1 (*Solanum tuberosum*, AAN71761) (SEQ ID NO: 37).

FIG. 4. Protein sequence alignment of CcCAD1ap, CcCAD1b, CcCAD2, CcCAD3, CcCAD4p, CcCAD5p, and CcCAD6p with plant CAD protein sequences. Alignment of putative proteins encoded by the CcCAD gene with other CAD proteins available in the NCBI database was done using the CLUSTAL W program in the MegAlign software. Amino acids marked in grey match the amino acids most frequently found in this position. GenBank Accession Numbers are given in parentheses: EgCAD (*Eucalyptus gunnii*, CAA61275) (SEQ ID NO: 38); NtCAD1 (*Nicotiana tabacum*, AAX15956) (SEQ ID NO: 39); and NtCAD1-1 (*Nicotiana tabacum*, AAX15955) (SEQ ID NO: 40).

FIG. 5. Protein sequence alignment of CcF5Hp with plant F5H protein sequences. Alignment of putative protein encoded by the CcF5Hp gene with other F5H proteins available in the NCBI database was done using the CLUSTAL W program in the MegAlign software. Amino Acids marked in grey match the amino acids most frequently found in this position. GenBank Accession Numbers are given in parentheses: AtF5H (*Arabidopsis thaliana*, AAD11580) (SEQ ID NO: 42); and LeF5H (*Lycopersicon esculentum*, AAD37433) (SEQ ID NO: 42).

DETAILED DESCRIPTION OF ILLUSTRATIVE EMBODIMENTS

Definitions

Figure 1:
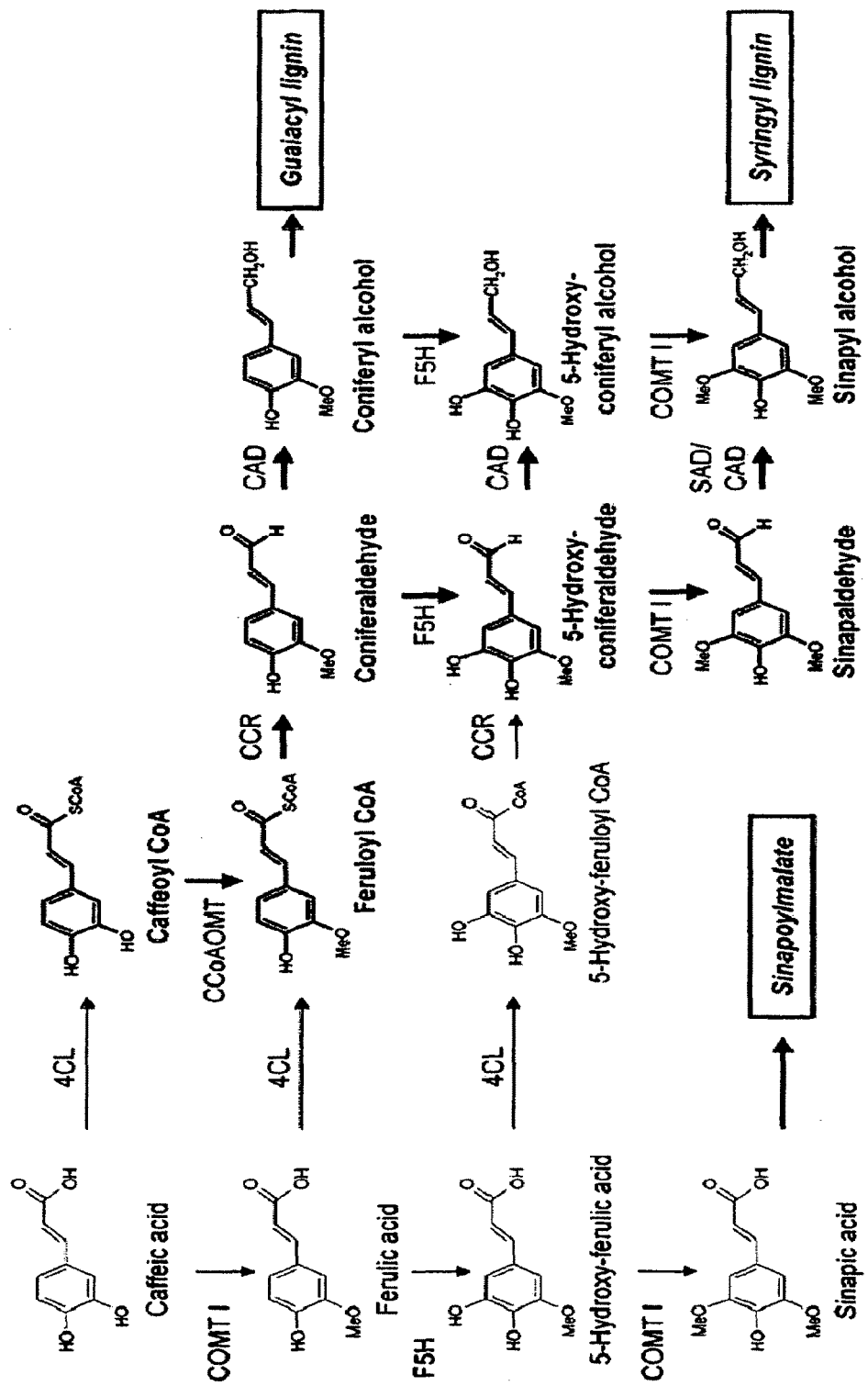
FIG. 1: Monolignols biosynthetic pathway. This representation of the plant lignins pathway is according from Hoffman et al., 2004. 4CL, 4-hydroxycinnamoyl-CoA ligase; CAD; cinnamyl-alcohol dehydrogenase; CCR, cinnamoyl-CoA reductase; COMT I, caffeic/5-hydroxyferulic acid O-methyltransferase; F5H, ferulate 5-hydroxylase; SAD, sinapyl-alcohol dehydrogenase.

Various terms relating to the biological molecules and other aspects of the present invention are used throughout the specification and claims.

The term "lignin biosynthetic pathways" refers to polypeptides that participate in lignin biosynthesis in plants, and more specifically, in coffee plants. This term encompasses the specific mechanism of action of each respective protein in the pathway. The polypeptides include without limitation, caffeic acid O-methyltransferase ("COMT"), cinnamoyl CoA reductase ("CCR"), cinnamyl alcohol dehydrogenase ("CAD"), and ferulate 5-hydroxylase (F5H), as exemplified herein.

"Isolated" means altered "by the hand of man" from the natural state. If a composition or substance occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated", as the term is employed herein.

"Polynucleotide," also referred to as "nucleic acid molecule", generally refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., Analysis for Protein Modifications and Nonprotein Cofactors, Meth Enzymol (1990) 182:626-646 and Rattan et al., Protein Synthesis: Posttranslational Modifications and Aging, Ann NY Acad Sci (1992) 663:48-62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions or deletions in any combination. A substituted or inserted amino acid residue may or may not be one encoded by the genetic code. A variant of a polynucleotide or polypeptide may be naturally occurring, such as an allelic variant, or it may be a variant that is not known to occur naturally. Non-naturally occurring variants of polynucleotides and polypeptides may be made by mutagenesis techniques or by direct synthesis.

In reference to mutant plants, the terms "null mutant" or "loss-of-function mutant" are used to designate an organism or genomic DNA sequence with a mutation that causes a gene product to be non-functional or largely absent. Such mutations may occur in the coding and/or regulatory regions of the gene, and may be changes of individual residues, or insertions or deletions of regions of nucleic acids. These mutations may also occur in the coding and/or regulatory regions of other genes which may regulate or control a gene and/or encoded protein, so as to cause the protein to be non-functional or largely absent.

The term "substantially the same" refers to nucleic acid or amino acid sequences having sequence variations that do not materially affect the nature of the protein (i.e., the structure, stability characteristics, substrate specificity and/or biological activity of the protein). With particular reference to nucleic acid sequences, the term "substantially the same" is intended to refer to the coding region and to conserved sequences governing expression, and refers primarily to degenerate codons encoding the same amino acid, or alternate codons encoding conservative substitute amino acids in the encoded polypeptide. With reference to amino acid sequences, the term "substantially the same" refers generally to conservative substitutions and/or variations in regions of the polypeptide not involved in determination of structure or function.

The terms "percent identical" and "percent similar" are also used herein in comparisons among amino acid and nucleic acid sequences. When referring to amino acid sequences, "identity" or "percent identical" refers to the percent of the amino acids of the subject amino acid sequence that have been matched to identical amino acids in the compared amino acid sequence by a sequence analysis program. "Percent similar" refers to the percent of the amino acids of the subject amino acid sequence that have been matched to identical or conserved amino acids. Conserved amino acids are those which differ in structure but are similar in physical properties such that the exchange of one for another would not appreciably change the tertiary structure of the resulting protein. Conservative substitutions are defined in Taylor (1986, *J. Theor. Biol.* 119:205). When referring to nucleic acid molecules, "percent identical" refers to the percent of the nucleotides of the subject nucleic acid sequence that have been matched to identical nucleotides by a sequence analysis program. The terms "identity" or "identical" are used interchangeably herein with the terms "homology" or "homologous."

"Identity" and "similarity" can be readily calculated by known methods. Nucleic acid sequences and amino acid sequences can be compared using computer programs that align the similar sequences of the nucleic or amino acids and thus define the differences. In preferred methodologies, the BLAST programs (NCBI) and parameters used therein are employed, and the DNAstar system (Madison, Wis.) is used to align sequence fragments of genomic DNA sequences. However, equivalent alignments and similarity/identity assessments can be obtained through the use of any standard alignment software. For instance, the GCG Wisconsin Package version 9.1, available from the Genetics Computer Group in Madison, Wis., and the default parameters used (gap creation penalty=12, gap extension penalty=4) by that program may also be used to compare sequence identity and similarity.

"Antibodies" as used herein includes polyclonal and monoclonal antibodies, chimeric, single chain, and humanized antibodies, as well as antibody fragments (e.g., Fab, Fab', $F(ab')_2$ and $F_v$), including the products of a Fab or other immunoglobulin expression library. With respect to antibodies, the term, "immunologically specific" or "specific" refers to antibodies that bind to one or more epitopes of a protein of interest, but which do not substantially recognize and bind other molecules in a sample containing a mixed population of antigenic biological molecules. Screening assays to determine binding specificity of an antibody are well known and routinely practiced in the art. For a comprehensive discussion of such assays, see Harlow et al. (Eds.), ANTIBODIES A LABORATORY MANUAL; Cold Spring Harbor Laboratory; Cold Spring Harbor, N.Y. (1988), Chapter 6.

The term "substantially pure" refers to a preparation comprising at least 50-60% by weight the compound of interest (e.g., nucleic acid, oligonucleotide, protein, etc.). More preferably, the preparation comprises at least 75% by weight, and most preferably 90-99% by weight, the compound of interest. Purity is measured by methods appropriate for the compound of interest (e.g., chromatographic methods, agarose or polyacrylamide gel electrophoresis, HPLC analysis, and the like).

With respect to single-stranded nucleic acid molecules, the term "specifically hybridizing" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule, to the substantial exclusion of hybridization of the oligonucleotide with single-stranded nucleic acids of non-complementary sequence.

A "coding sequence" or "coding region" refers to a nucleic acid molecule having sequence information necessary to produce a gene product, such as an amino acid or polypeptide, when the sequence is expressed. The coding sequence may comprise untranslated sequences (e.g., introns or 5' or 3' untranslated regions) within translated regions, or may lack such intervening untranslated sequences (e.g., as in cDNA).

"Intron" refers to polynucleotide sequences in a nucleic acid that do not code information related to protein synthesis. Such sequences are transcribed into mRNA, but are removed before translation of the mRNA into a protein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

Transcriptional and translational control sequences are DNA regulatory sequences, such as promoters, enhancers, polyadenylation signals, terminators, and the like, that provide for the expression of a coding sequence in a host cell.

The terms "promoter," "promoter region," or "promoter sequence" refer generally to transcriptional regulatory regions of a gene, which may be found at the 5' or 3' side of the coding region, or within the coding region, or within introns. Typically, a promoter is a DNA regulatory region capable of binding RNA polymerase in a cell and initiating transcription of a downstream (3' direction) coding sequence. The typical 5' promoter sequence is bounded at its 3' terminus by the transcription initiation site and extends upstream (5' direction) to include the minimum number of bases or elements necessary to initiate transcription at levels detectable above background. Within the promoter sequence is a transcription initiation site (conveniently defined by mapping with nuclease S1), as well as protein binding domains (consensus sequences) responsible for the binding of RNA polymerase.

A "vector" is a replicon, such as plasmid, phage, cosmid, or virus to which another nucleic acid segment may be operably inserted so as to bring about the replication or expression of the segment.

The term "nucleic acid construct" or "DNA construct" is sometimes used to refer to a coding sequence or sequences operably linked to appropriate regulatory sequences and inserted into a vector for transforming a cell. This term may be used interchangeably with the term "transforming DNA" or "transgene." Such a nucleic acid construct may contain a coding sequence for a gene product of interest, along with a selectable marker gene and/or a reporter gene.

A "marker gene" or "selectable marker gene" is a gene whose encoded gene product confers a feature that enables a cell containing the gene to be selected from among cells not containing the gene. Vectors used for genetic engineering typically contain one or more selectable marker genes. Types of selectable marker genes include (1) antibiotic resistance genes, (2) herbicide tolerance or resistance genes, and (3) metabolic or auxotrophic marker genes that enable transformed cells to synthesize an essential component, usually an amino acid, which the cells cannot otherwise produce.

A "reporter gene" is also a type of marker gene. It typically encodes a gene product that is assayable or detectable by standard laboratory means (e.g., enzymatic activity, fluorescence).

The term "express," "expressed," or "expression" of a gene refers to the biosynthesis of a gene product. The process involves transcription of the gene into mRNA and then translation of the mRNA into one or more polypeptides, and encompasses all naturally occurring post-translational modifications.

"Endogenous" refers to any constituent, for example, a gene or nucleic acid, or polypeptide, that can be found naturally within the specified organism.

A "heterologous" region of a nucleic acid construct is an identifiable segment (or segments) of the nucleic acid molecule within a larger molecule that is not found in association with the larger molecule in nature. Thus, when the heterologous region comprises a gene, the gene will usually be flanked by DNA that does not flank the genomic DNA in the genome of the source organism. In another example, a heterologous region is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein. The term "DNA construct", as defined above, is also used to refer to a heterologous region, particularly one constructed for use in transformation of a cell.

A cell has been "transformed" or "transfected" by exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

"Grain," "seed," or "bean," refers to a flowering plant's unit of reproduction, capable of developing into another such plant. As used herein, especially with respect to coffee plants, the terms are used synonymously and interchangeably.

As used herein, the term "plant" includes reference to whole plants, plant organs (e.g., leaves, stems, shoots, roots), seeds, pollen, plant cells, plant cell organelles, and progeny thereof. Parts of transgenic plants are to be understood within the scope of the invention to comprise, for example, plant cells, protoplasts, tissues, callus, embryos as well as flowers, stems, seeds, pollen, fruits, leaves, or roots originating in transgenic plants or their progeny.

Description

In one of its aspects the present invention features nucleic acid molecules from coffee that encode a variety of proteins involved in the lignin biosynthetic pathways. Representative examples of nucleic acid molecules encoding proteins that comprise the lignin biosynthetic pathways were identified from databases of over 47,000 expressed sequence tags (ESTs) from several *Coffea canephora* (robusta) cDNA libraries made with RNA isolated from young leaves and from the grain and pericarp tissues of cherries harvested at different stages of development. Overlapping ESTs were identified and "clustered" into unigenes (contigs) comprising complete coding sequences. The unigene sequences were annotated by performing a BLAST search of each individual sequence against the NCBI (National Center for Biotechnology Information) non-redundant protein database.

BLAST searches of the coffee EST databases using biochemically characterized protein sequences from public databases revealed gene sequences representing several important enzymes of the lignin biosynthetic pathways in the coffee plant. The fall open reading frame of several of these sequences were obtained, and a partial open reading frame was obtained for several other sequences. These cDNAs and their encoded proteins are referred to herein as follows:

| Enzyme | cDNA (SEQ ID NO:) | | encoded protein (SEQ ID NO:) | |
|---|---|---|---|---|
| Caffeic Acid O-Methyltransferase | CcCOMT1 | 1 | CcCOMT1 | 15 |
| | CcCOMT2p | 2 | CcCOMT2p | 16 |
| | CcCOMT3p | 3 | CcCOMT3p | 17 |
| | CcCOMT4p | 4 | CcCOMT4p | 18 |
| Cinnamoyl CoA Reductase | CcCCR1 | 5 | CcCCR1 | 19 |
| | CcCCR2 | 6 | CcCCR2 | 20 |
| Cinnamyl Alcohol Dehydrogenase | CcCAD1ap | 7 | CcCAD1ap | 21 |
| | CcCAD1b | 8 | CcCAD1b | 22 |
| | CcCAD2 | 9 | CcCAD2 | 23 |
| | CcCAD3 | 10 | CcCAD3 | 24 |
| | CcCAD4p | 11 | CcCAD4p | 25 |
| | CcCAD5p | 12 | CcCAD5p | 26 |
| | CcCAD6p | 13 | CcCAD6p | 27 |
| Ferulate 5-Hydroxylase | CcF5Hp | 14 | CcF5Hp | 28 |

Although polynucleotides encoding proteins that catalyze key steps the lignin biosynthetic pathways from *Coffea canephora* are described and exemplified herein, this invention is intended to encompass nucleic acids and encoded proteins from other *Coffea* species that are sufficiently similar to be used interchangeably with the *C. canephora* polynucleotides and proteins for the purposes described below. Accordingly, when the term polypeptides or proteins that "comprise the lignin biosynthetic pathways" is used herein, it is intended to encompass all *Coffea* proteins that have the general physical, biochemical, and functional features described herein, as well as the polynucleotides that encode them.

Considered in terms of their sequences, the polynucleotides of the invention that encode proteins that comprise the lignin biosynthetic pathways include allelic variants and natural mutants of SEQ ID NOs:1-14, which are likely to be found in different varieties of *C. arabica* and *C. canephora*, and homologs of SEQ ID NOs:1-14 likely to be found in different coffee species. Because such variants and homologs are expected to possess certain differences in nucleotide and amino acid sequence, this invention provides isolated polynucleotides encoding proteins that comprise the lignin biosynthetic pathways that have at least about 30%, preferably at least about 40%, 45%, 50% or 55%, more preferably at least about 60%, 61%, 62%, 63%, 64%, 65%, 66%, 67%, 68%, 69% or 70%, more preferably at least about 71%, 72%, 73%, 74%, 75%, 76%, 77%. 78%, 79%, or 80%, even more preferably 81%, 82%, 83%, 84%, 85%, 86%, 87%, 88%, 89%, and even more preferably 90%, 91%, 92%, 93%, 94%, 95%, and most preferably 96%, 97%, 98% and 99% or more identity with any one of SEQ ID NOs:15-28, and comprise a nucleotide sequence having equivalent ranges of identity to any one of SEQ ID NOs:1-14. Because of the natural sequence variation likely to exist among proteins that comprise the lignin biosynthetic pathways, and the genes encoding them in different coffee varieties and species, one skilled in the art would expect to find this level of variation, while still maintaining the unique properties of the polypeptides and polynucleotides of the present invention. Such an expectation is due in part to the degeneracy of the genetic code, as well as to the known evolutionary success of conservative amino acid sequence variations, which do not appreciably alter the nature of the encoded protein. Accordingly, such variants and homologs are considered substantially the same as one another and are included within the scope of the present invention.

The gene regulatory sequences associated with genes encoding proteins that comprise the lignin biosynthetic pathways are of practical utility and are considered within the scope of the present invention. Promoters and other gene regulatory sequences of genes encoding proteins that comprise the lignin biosynthetic pathways from any coffee species may be obtained by the methods described below, and may be utilized in accordance with the present invention. Promoters and regulatory elements governing tissue specificity and temporal specificity of the expression of genes encoding proteins that comprise the lignin biosynthetic pathways may be used to advantage, alter or modify the expression of proteins that comprise the lignin biosynthetic pathways toward the goal of enhancing the flavor and aroma of coffee products produced from coffee beans comprising such modifications, among other utilities.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Sambrook et al., Molecular Cloning, Cold Spring Harbor Laboratory (1989) or Ausubel et al. (eds), Current Protocols in Molecular Biology, John Wiley & Sons (2005) are used.

Nucleic Acid Molecules, Proteins and Antibodies

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information, such as the cDNA having SEQ ID NOs:1-14, enables preparation of an isolated nucleic acid molecule of the invention by oligonucleotide synthesis. Synthetic oligonucleotides may be prepared by the phosphoramidite method employed in the Applied Biosystems 38A DNA Synthesizer or similar devices. The resultant construct may be purified according to methods known in the art, such as high performance liquid chromatography (HPLC). Long, double-stranded polynucleotides, such as a DNA molecule of the present invention, must be synthesized in stages, due to the size limitations inherent in current oligonucleotide synthetic methods. Thus, for example, a long double-stranded molecule may be synthesized as several smaller segments of appropriate complementarity. Complementary segments thus produced may be annealed such that each segment possesses appropriate cohesive termini for attachment of an adjacent segment. Adjacent segments may be ligated by annealing cohesive termini in the presence of DNA ligase to construct an entire long double-stranded molecule. A synthetic DNA molecule so constructed may then be cloned and amplified in an appropriate vector.

In accordance with the present invention, nucleic acids having the appropriate level sequence homology with part or all of the coding and/or regulatory regions genes encoding proteins that comprise the lignin biosynthetic pathways may be identified by using hybridization and washing conditions of appropriate stringency. It will be appreciated by those skilled in the art that the aforementioned strategy, when applied to genomic sequences, will, in addition to enabling isolation coding sequences for genes encoding proteins that comprise the lignin biosynthetic pathways, also enable isolation of promoters and other gene regulatory sequences associated with genes encoding proteins that comprise the lignin biosynthetic pathways, even though the regulatory sequences themselves may not share sufficient homology to enable suitable hybridization.

As a typical illustration, hybridizations may be performed according to the method of Sambrook et al., using a hybridization solution comprising: 5×SSC, 5×Denhardt's reagent, 1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 2×SSC and 0.1% SDS; (4) 2 hours at 45-55° C. in 2×SSC and 0.1% SDS, changing the solution every 30 minutes.

One common formula for calculating the stringency conditions required to achieve hybridization between nucleic acid molecules of a specified sequence homology (Sambrook et al., 1989):

$$Tm=81.5° C.+16.6 \text{ Log } [Na+]+0.41(\% G+C)-0.63(\% \text{ formamide})-600/\#bp \text{ in duplex}$$

As an illustration of the above formula, using [Na+]= [0.368] and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C. In one embodiment, the hybridization is at 37° C. and the final wash is at 42° C.; in another embodiment the hybridization is at 42° C. and the final wash is at 50° C.; and in yet another embodiment the hybridization is at 42° C. and final wash is at 65° C., with the above hybridization and wash solutions. Conditions of high stringency include hybridization at 42° C. in the above hybridization solution and a final wash at 65° C. in 0.1×SSC and 0.1% SDS for 10 minutes.

Nucleic acids of the present invention may be maintained as DNA in any convenient cloning vector. In a preferred embodiment, clones are maintained in plasmid cloning/expression vector, such as pGEM-T (Promega Biotech, Madison, Wis.), pBluescript (Stratagene, La Jolla, Calif.), pCR4-TOPO (Invitrogen, Carlsbad, Calif.) or pET28a+ (Novagen, Madison, Wis.), all of which can be propagated in a suitable E. coli host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention. Such oligonucleotides are useful as probes for detecting genes encoding proteins that comprise the lignin biosynthetic pathways or mRNA in test samples of plant tissue, e.g., by PCR amplification, or for the positive or negative regulation of expression genes encoding proteins that comprise the lignin biosynthetic pathways at or before translation of the mRNA into proteins. Methods in which oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR, including RT-PCR) and ligase chain reaction (LCR).

Polypeptides encoded by nucleic acids of the invention may be prepared in a variety of ways, according to known methods. If produced in situ the polypeptides may be purified from appropriate sources, e.g., seeds, pericarps, or other plant parts.

Alternatively, the availability of nucleic acid molecules encoding the polypeptides enables production of the proteins using in vitro expression methods known in the art. For example, a cDNA or gene may be cloned into an appropriate in vitro transcription vector, such a pSP64 or pSP65 for in vitro transcription, followed by cell-free translation in a suitable cell-free translation system, such as wheat germ or rabbit reticulocytes. In vitro transcription and translation systems are commercially available, e.g., from Promega Biotech, Madison, Wis., BRL, Rockville, Md. or Invitrogen, Carlsbad, Calif.

According to a preferred embodiment, larger quantities of polypeptides that are active in the lignin biosynthetic pathways may be produced by expression in a suitable prokaryotic or eukaryotic system. For example, part or all of a DNA molecule, such as the cDNAs having SEQ ID NOs: 1-14, may be inserted into a plasmid vector adapted for expression in a bacterial cell (such as E. coli) or a yeast cell (such as Saccharomyces cerevisiae), or into a baculovirus vector for expression in an insect cell. Such vectors comprise the regulatory elements necessary for expression of the DNA in the host cell, positioned in such a manner as to permit expression of the DNA in the host cell. Such regulatory elements required for expression include promoter sequences, transcription initiation sequences and, optionally, enhancer sequences.

The polypeptides that comprise the lignin biosynthetic pathways produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein. Such methods are commonly used by skilled practitioners.

The polypeptides that comprise the lignin biosynthetic pathways of the invention, prepared by the aforementioned methods, may be analyzed according to standard procedures.

Polypeptides that comprise the lignin biosynthetic pathways purified from coffee, or produced recombinantly, may be used to generate polyclonal or monoclonal antibodies, antibody fragments or derivatives as defined herein, according to known methods. Antibodies that recognize and bind fragments of the polypeptides that comprise the lignin biosynthetic pathways of the invention are also contemplated, provided that the antibodies are specific for polypeptides that comprise the lignin biosynthetic pathways. For example, if analyses of the proteins or Southern and cloning analyses (see below) indicate that the cloned genes belongs to a multigene family, then member-specific antibodies made to synthetic peptides corresponding to nonconserved regions of the protein can be generated.

Kits comprising an antibody of the invention for any of the purposes described herein are also included within the scope of the invention. In general, such a kit includes a control antigen for which the antibody is immunospecific.

Vectors, Cells, Tissues and Plants

Also featured in accordance with the present invention are vectors and kits for producing transgenic host cells that contain a polynucleotide encoding polypeptides that comprise the lignin biosynthetic pathways, or an oligonucleotide, or homolog, analog or variant thereof in a sense or antisense orientation, or a reporter gene and other constructs under control of cell or tissue-specific promoters and other regulatory sequences. Suitable host cells include, but are not limited to, plant cells, bacterial cells, yeast and other fungal cells, insect cells and mammalian cells. Vectors for transforming a wide variety of these host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression, to name a few.

The present invention includes transgenic plants comprising one or more copies of a gene encoding a polypeptide that comprises the lignin biosynthetic pathways, or nucleic acid sequences that inhibit the production or function of a plant's endogenous polypeptides that comprise the lignin biosynthetic pathways. This is accomplished by transforming plant cells with a transgene that comprises part of all of a coding sequence for a polypeptide that comprises the lignin biosynthetic pathways, or mutant, antisense or variant thereof, including RNA, controlled by either native or recombinant regulatory sequences, as described below. For transgenic plants, coffee species are preferred, including, without limitation, C. abeokutae, C. arabica, C. arnoldiana, C. aruwemiensis, C. bengalensis, C. canephora, C. congensis C. dewevrei, C. excelsa, C. eugenioides, and C. heterocalyx, C. kapakata, C. khasiana, C. liberica, C. moloundou, C. rasemosa, C. salvatrix, C. sessiflora, C. stenophylla, C. travencorensis, C. wightiana and C. zanguebariae. Plants of any species are also included in the invention; these include, but are not limited to, tobacco, Arabidopsis and other "laboratory-friendly" species, cereal crops such as maize, wheat, rice, soybean barley, rye, oats, sorghum, alfalfa, clover and the like, oil-producing plants such as canola, safflower, sunflower, peanut, cacao and the like, vegetable crops such as tomato tomatillo, potato, pepper, eggplant, sugar beet, carrot, cucumber, lettuce, pea and the like, horticultural plants such as aster, begonia, chrysanthemum, delphinium, petunia, zinnia, lawn and turfgrasses and the like.

Transgenic plants can be generated using standard plant transformation methods known to those skilled in the art. These include, but are not limited to, Agrobacterium vectors, polyethylene glycol treatment of protoplasts, biolistic DNA delivery, UV laser microbeam, gemini virus vectors or other plant viral vectors, calcium phosphate treatment of protoplasts, electroporation of isolated protoplasts, agitation of cell suspensions in solution with microbeads coated with the transforming DNA, agitation of cell suspension in solution with silicon fibers coated with transforming DNA, direct DNA uptake, liposome-mediated DNA uptake, and the like. Such methods have been published in the art. See, e.g., Methods for Plant Molecular Biology (Weissbach & Weissbach, eds., 1988); Methods in Plant Molecular Biology (Schuler & Zielinski, eds., 1989); Plant Molecular Biology Manual (Gelvin, Schilperoort, Verma, eds., 1993); and Methods in Plant Molecular Biology—A Laboratory Manual (Maliga, Klessig, Cashmore, Gruissem & Varner, eds., 1994).

The method of transformation depends upon the plant to be transformed. Agrobacterium vectors are often used to transform dicot species. Agrobacterium binary vectors include, but are not limited to, BIN19 and derivatives thereof, the pBI vector series, and binary vectors pGA482, pGA492, pLH7000 (GenBank Accession AY234330) and any suitable one of the pCAMBIA vectors (derived from the pPZP vectors constructed by Hajdukiewicz, Svab & Maliga, (1994) Plant Mol Biol 25: 989-994, available from CAMBIA, GPO Box 3200, Canberra ACT 2601, Australia or via the worldwide web at CAMBIA.org). For transformation of monocot species, biolistic bombardment with particles coated with transforming DNA and silicon fibers coated with transforming DNA are often useful for nuclear transformation. Alternatively, Agrobacterium "superbinary" vectors have been used successfully for the transformation of rice, maize and various other monocot species.

DNA constructs for transforming a selected plant comprise a coding sequence of interest operably linked to appropriate 5' regulatory sequences (e.g., promoters and translational regulatory sequences) and 3' regulatory sequences (e.g., terminators). In a preferred embodiment, a coding sequence encoding a polypeptide that comprises the lignin biosynthetic pathways under control of its natural 5' and 3' regulatory elements is utilized. In other embodiments, coding and regulatory sequences are swapped to alter the protein content of the seed of the transformed plant for a phenotypic improvement, e.g., in flavor, aroma or other feature.

In an alternative embodiment, the coding region of the gene is placed under a powerful constitutive promoter, such as the Cauliflower Mosaic Virus (CaMV) 35S promoter or the figwort mosaic virus 35S promoter. Other constitutive promoters contemplated for use in the present invention include, but are not limited to: T-DNA mannopine synthetase, nopaline synthase and octopine synthase promoters. In other embodiments, a strong monocot promoter is used, for example, the maize ubiquitin promoter, the rice actin promoter or the rice tubulin promoter (Jeon et al., Plant Physiology. 123: 1005-14, 2000).

Transgenic plants with coding sequences to express polypeptides that comprise the lignin biosynthetic pathways under an inducible promoter are also contemplated to be within the scope of the present invention. Inducible plant promoters include the tetracycline repressor/operator controlled promoter, the heat shock gene promoters, stress (e.g., wounding)-induced promoters, defense responsive gene promoters (e.g. phenylalanine ammonia lyase genes), wound induced gene promoters (e.g., hydroxyproline rich cell wall protein genes), chemically-inducible gene promoters (e.g., nitrate reductase genes, glucanase genes, chitinase genes, etc.) and dark-inducible gene promoters (e.g., asparagine synthetase gene) to name only a few.

Tissue specific and development-specific promoters are also contemplated for use in the present invention. Non-limiting examples of seed-specific promoters include Cim1 (cytokinin-induced message), cZ19B1 (maize 19 kDa zein), milps (myo-inositol-1-phosphate synthase), and celA (cellulose synthase) (U.S. application Ser. No. 09/377,648), bean beta.-phaseolin, napin, beta.-conglycinin, soybean lectin, cruciferin, maize 15 kDa zein, 22 kDa zein, 27 kDa zein, g-zein, waxy, shrunken 1, shrunken 2, and globulin 1, soybean 11S legumin (Bäumlein et al., 1992), and C. canephora 11S seed storage protein (Marraccini et al., 1999, Plant Physiol. Biochem. 37: 273-282). See also WO 00/12733, where seed-preferred promoters from end1 and end2 genes are disclosed. Other *Coffea* seed specific promoters may also be utilized, including but not limited to the oleosin gene promoter described in commonly-owned, co-pending PCT Application No. US2006/026121, the dehydrin gene promoter described in commonly-owned, co-pending PCT Application No. US2006/026234, and the 9-cis-epoxycarotenoid dioxygenase gene promoter described in commonly-owned, co-pending PCT Application No. US2006/034402. Examples of other tissue-specific promoters include, but are not limited to: the ribulose bisphosphate carboxylase (RuBisCo) small subunit gene promoters (e.g., the coffee small subunit promoter as described by Marracini et al., 2003) or chlorophyll a/b binding protein (CAB) gene promoters for expression in photosynthetic tissue; and the root-specific glutamine synthetase gene promoters where expression in roots is desired.

The coding region is also operably linked to an appropriate 3' regulatory sequence. In embodiments where the native 3' regulatory sequence is not use, the nopaline synthetase polyadenylation region may be used. Other useful 3' regulatory regions include, but are not limited to the octopine synthase polyadenylation region.

The selected coding region, under control of appropriate regulatory elements, is operably linked to a nuclear drug resistance marker, such as kanamycin resistance. Other useful selectable marker systems include genes that confer antibiotic or herbicide resistances (e.g., resistance to hygromycin, sulfonylurea, phosphinothricin, or glyphosate) or genes conferring selective growth (e.g., phosphomannose isomerase, enabling growth of plant cells on mannose). Selectable marker genes include, without limitation, genes encoding antibiotic resistance, such as those encoding neomycin phosphotransferase II (NEO), dihydrofolate reductase (DHFR) and hygromycin phosphotransferase (HPT), as well as genes that confer resistance to herbicidal compounds, such as glyphosate-resistant EPSPS and/or glyphosate oxidoreducatase (GOX), *Bromoxynil nitrilase* (BXN) for resistance to bromoxynil, AHAS genes for resistance to imidazolinones, sulfonylurea resistance genes, and 2,4-dichlorophenoxyacetate (2,4-D) resistance genes.

In certain embodiments, promoters and other expression regulatory sequences encompassed by the present invention are operably linked to reporter genes. Reporter genes contemplated for use in the invention include, but are not limited to, genes encoding green fluorescent protein (GFP), red fluorescent protein (DsRed), Cyan Fluorescent Protein (CFP), Yellow Fluorescent Protein (YFP), Cerianthus Orange Fluorescent Protein (cOFP), alkaline phosphatase (AP), β-lactamase, chloramphenicol acetyltransferase (CAT), adenosine deaminase (ADA), aminoglycoside phosphotransferase (neo$^r$, G418$^r$) dihydrofolate reductase (DHFR), hygromycin-B-phosphotransferase (HPH), thymidine kinase (TK), lacZ (encoding α-galactosidase), and xanthine guanine phosphoribosyltransferase (XGPRT), Beta-Glucuronidase (gus), Placental Alkaline Phosphatase (PLAP), Secreted Embryonic Alkaline Phosphatase (SEAP), or Firefly or Bacterial Luciferase (LUC). As with many of the standard procedures associated with the practice of the invention, skilled artisans will be aware of additional sequences that can serve the function of a marker or reporter.

Additional sequence modifications are known in the art to enhance gene expression in a cellular host. These modifications include elimination of sequences encoding superfluous polyadenylation signals, exon-intron splice site signals, transposon-like repeats, and other such well-characterized sequences that may be deleterious to gene expression. Alternatively, if necessary, the G/C content of the coding sequence may be adjusted to levels average for a given coffee plant cell host, as calculated by reference to known genes expressed in a coffee plant cell. Also, when possible, the coding sequence is modified to avoid predicted hairpin secondary mRNA structures. Another alternative to enhance gene expression is to use 5' leader sequences. Translation leader sequences are well known in the art, and include the cis-acting derivative (omega') of the 5' leader sequence (omega) of the tobacco mosaic virus, the 5' leader sequences from brome mosaic virus, alfalfa mosaic virus, and turnip yellow mosaic virus.

Plants are transformed and thereafter screened for one or more properties, including the presence of the transgene product, the transgene-encoding mRNA, or an altered phenotype associated with expression of the transgene. It should be recognized that the amount of expression, as well as the tissue- and temporal-specific pattern of expression of the transgenes in transformed plants can vary depending on the position of their insertion into the nuclear genome. Such positional effects are well known in the art. For this reason, several nuclear transformants should be regenerated and tested for expression of the transgene.

Methods

The nucleic acids and polypeptides of the present invention can be used in any one of a number of methods whereby the protein products can be expressed in coffee plants in order that the proteins may play a role in protecting the coffee plant from pathogens, and from herbivore, insect, or pathogen attack, and in the enhancement of flavor and/or aroma of the coffee beverage or coffee products ultimately produced from the bean of the coffee plant expressing the protein. Similarly, the polypeptides of the invention can be used in any one of a number of methods whereby the lignins and other such phytochemical products synthesized from the polypeptides may play a role in protecting the plant from pathogens, and from herbivore or insect attack, and in the enhancement of flavor and/or aroma of the coffee beverage or coffee products ultimately produced from the bean of the coffee plant containing the lignins.

With respect to protection of the plant from attack by pathogens, herbivores, and insects, lignins strengthen the plant cell wall and impede the degradation, especially digestion, of cell wall polysaccharides, and thus act as a major line of defense for the plant. (Hatfield et al. 2001). Accordingly, the ability to manipulate production of polypeptides that comprise the biosynthetic pathway for lignins in a plant, or even to use the polynucleotides and proteins of the invention to monitor such gene expression, will enable study and manipulation of the response of the coffee plant to pathogen, herbivore, or insect attack. This knowledge will enable the generation of modified coffee plants that are better equipped against disease or devastation by pathogens, herbivores or insects.

With respect to flavor and aroma of roasted coffee grain, it is expected that the polypeptides that comprise the lignin biosynthetic pathways exert some influence on the generation of coffee flavors via the Maillard reaction that occurs during roasting, by means of the content of the proteins themselves, or the products such as lignins they produce. Proteins, and particularly protein degradation products (peptides and amino acids), represent an important group of flavor precursors (Spanier et al., 2004). Therefore, relatively abundant proteins such as those that comprise the lignin biosynthetic pathways can be expected to make some contribution to the flavor generating reactions that occur during coffee roasting.

Such a contribution may stem from the concentration of the proteins themselves in the coffee bean, or the concentration of the lignins ultimately produced from the proteins. The ability to monitor (e.g., through marker-assisted breeding) or manipulate protein expression profiles for polypeptides that comprise the lignin biosynthetic pathway is provided by the polynucleotides of the present invention, in accordance with the methods described herein.

Thus, one aspect of the present invention features methods to alter the profile of polypeptides that comprise the lignin biosynthetic pathway in a plant, preferably coffee, comprising increasing or decreasing an amount or activity of one or more polypeptides that comprise the lignin biosynthetic pathway in the plant. For instance, in one embodiment of the invention, a gene encoding a polypeptide that comprises the lignin biosynthetic pathway under control of its own expression-controlling sequences is used to transform a plant for the purpose of increasing production of that polypeptide in the plant. Alternatively, a coding region for a polypeptide that comprises the lignin biosynthetic pathway is operably linked to heterologous expression controlling regions, such as constitutive or inducible promoters.

Loss-of-function (null) mutant plants may be created or selected from populations of plant mutants currently available. It will also be appreciated by those of skill in the art that mutant plant populations may also be screened for mutants that over-express a particular polypeptide that comprises the lignin biosynthetic pathway, utilizing one or more of the methods described herein. Mutant populations can be made by chemical mutagenesis, radiation mutagenesis, and transposon or T-DNA insertions, or targeting induced local lesions in genomes (TILLING, see, e.g., Henikoff et al., 2004, *Plant Physiol.* 135(2): 630-636; Gilchrist & Haughn, 2005, *Curr. Opin. Plant Biol.* 8(2): 211-215). The methods to make mutant populations are well known in the art.

The nucleic acids of the invention can be used to identify mutant polypeptides that comprise the lignin biosynthetic pathways in various plant species. In species such as maize or *Arabidopsis*, where transposon insertion lines are available, oligonucleotide primers can be designed to screen lines for insertions in the genes encoding polypeptides that comprise the lignin biosynthetic pathways. Through breeding, a plant line may then be developed that is heterozygous or homozygous for the interrupted gene.

A plant also may be engineered to display a phenotype similar to that seen in null mutants created by mutagenic techniques. A transgenic null mutant can be created by a expressing a mutant form of a selected polypeptide that comprises the lignin biosynthetic pathways to create a "dominant negative effect." While not limiting the invention to any one mechanism, this mutant protein will compete with wild-type protein for interacting proteins or other cellular factors. Examples of this type of "dominant negative" effect are well known for both insect and vertebrate systems (Radke et al., 1997, *Genetics* 145: 163-171; Kolch et al., 1991, *Nature* 349: 426-428).

Another kind of transgenic null mutant can be created by inhibiting the translation of mRNA encoding the polypeptides that comprise the lignin biosynthetic pathways by "post-transcriptional gene silencing." The gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art.

Antisense molecules may be provided in situ by transforming plant cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al, 1998, *PNAS* 95: 13959-13964). In this regard, dsRNA containing sequences that correspond to part or all of at least one intron have been found particularly effective. In one embodiment, part or all of the coding sequence antisense strand is expressed by a transgene. In another embodiment, hybridizing sense and antisense strands of part or all of the coding sequence for polypeptides that comprise the lignin biosynthetic pathways are transgenically expressed.

In another embodiment, lignin genes may be silenced through the use of a variety of other post-transcriptional gene silencing (RNA silencing) techniques that are currently available for plant systems. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner (for reviews of RNA silencing in plants, see Horiguchi, 2004, *Differentiation* 72: 65-73; Baulcombe, 2004, *Nature* 431: 356-363; Herr, 2004, *Biochem. Soc. Trans.* 32: 946-951).

Small interfering RNAs may be chemically synthesized or transcribed and amplified is vitro, and then delivered to the cells. Delivery may be through microinjection (Tuschl T et al, 2002), chemical transfection (Agrawal N et al., 2003), electroporation or cationic liposome-mediated transfection (Brummelkamp T R et al., 2002; Elbashir S M et al., 2002), or any other means available in the art, which will be appreciated by the skilled artisan. Alternatively, the siRNA may be expressed intracellularly by inserting DNA templates for siRNA into the cells of interest, for example, by means of a plasmid, (Tuschl T et al., 2002), and may be specifically targeted to select cells. Small interfering RNAs have been successfully introduced into plants. (Klahre U et al., 2002).

A preferred method of RNA silencing in the present invention is the use of short hairpin RNAs (shRNA). A vector containing a DNA sequence encoding for a particular desired siRNA sequence is delivered into a target cell by an common means. Once in the cell, the DNA sequence is continuously transcribed into RNA molecules that loop back on themselves and form hairpin structures through intramolecular base pairing. These hairpin structures, once processed by the cell, are equivalent to siRNA molecules and are used by the cell to mediate RNA silencing of the desired protein. Various constructs of particular utility for RNA silencing in plants are described by Horiguchi, 2004, supra. Typically, such a construct comprises a promoter, a sequence of the target gene to be silenced in the "sense" orientation, a spacer, the antisense of the target gene sequence, and a terminator.

Yet another type of synthetic null mutant can also be created by the technique of "co-suppression" (Vaucheret et al., 1998, *Plant J* 16(6): 651-659). Plant cells are transformed with a copy of the endogenous gene targeted for repression. In many cases, this results in the complete repression of the native gene as well as the transgene. In one embodiment, a gene encoding a polypeptide that comprises the lignin biosynthetic pathways from the plant species of interest is isolated and used to transform cells of that same species.

Mutant or transgenic plants produced by any of the foregoing methods are also featured in accordance with the present invention. Preferably, the plants are fertile, thereby being useful for breeding purposes. Thus, mutant or plants that exhibit one or more of the aforementioned desirable phenotypes can be used for plant breeding, or directly in agricultural or horticultural applications. They will also be of utility as research tools for the further elucidation of the participation of polypeptides that comprise the lignin biosynthetic pathways in flavor, aroma and other features of coffee seeds associated with pigments and photosynthesis. Plants containing one transgene or a specified mutation may also be crossed with plants containing a complementary transgene or genotype in order to produce plants with enhanced or combined phenotypes.

The present invention also features compositions and methods for producing, in a seed-preferred or seed-specific manner, any selected heterologous gene product in a plant. A coding sequence of interest is placed under control of a seed-specific coffee promoter and other appropriate regulatory sequences, to produce a seed-specific chimeric gene. The chimeric gene is introduced into a plant cell by any of the transformation methods described herein or known in the art. These chimeric genes and methods may be used to produce a variety of gene products of interest in the plant, including but not limited to: (1) detectable gene products such as GFP or GUS, as enumerated above; (2) gene products conferring an agronomic or horticultural benefit, such as those whose enzyme activities result in production of micronutrients (e.g., pro-vitamin A, also known as beta-carotene) or antioxidants (e.g., ascorbic acid, omega fatty acids, lycopene, isoprenes, terpenes); or (3) gene products for controlling pathogens or pests, such as described by Mourgues et al., (1998), TibTech 16: 203-210 or others known to be protective to plant seeds or detrimental to pathogens.

The following examples are provided to describe the invention in greater detail. The examples are intended illustrate, not to limit, the invention.

Example 1

Materials and Methods for Subsequent Examples

A genomic strategy was chosen as a first approach towards understanding lignin synthesis in coffee. This strategy was based on the recently completed Nestlé/Cornell EST (Expressed Sequence Tags) library which contains 46,914 high quality EST sequences. These sequences have been assembled in-silico into 13,175 unique DNA sequences (unigenes) representing *C. canephora* genes being expressed in young leaves, in developing pericarp tissues (all stages mixed), and in developing grain at several distinct stages.

The unigene set of the Nestlé/Cornell database was searched using the tblastn algorithm (Altschul et al. 1990) for coffee sequences encoding full or partial ORF's (open reading frame) for polypeptides that code for caffeic acid O-methyltransferases, cinnamoyl CoA reductases, cinnamyl alcohol dehydrogenases, and ferulate-5-hydroxylases exhibiting high similarity to biochemically characterized plant proteins present in the NCBI GenBank public databases. The longest cDNA of the unigene with the best hit for each protein sequence search was then isolated and sequenced. The in silico gene expression profile observed for each coffee gene using the complete EST database (i.e., number of ESTs found for each unigene in the different tissue libraries) is presented to give an indication about the tissues expressing each gene. It is noted, however, that when the number of ESTs found in a tissue is low (as is the case for most of the lignin genes presented), this type of expression data gives only a rough estimate of the relative expression levels in each tissue. The absence of an EST does not mean that there is no expression of this gene in that particular tissue.

DNA Sequencing. Plasmid DNA was purified using Qiagen kits according to the instructions given by the manufacturer. Plasmid DNA and PCR products were sequenced by GATC Biotech AG (Konstanz, Germany) using the dideoxy termination method (S anger et al., 1977). In some cases, the unique PCR fragments produced from the 5' RACE and genome walking experiments were directly sequenced, without purification or cloning, using the same primers as in the PCR amplification reactions. Computer analysis was performed using Laser Gene software package (DNASTAR). Homologies with sequences in the public GenBank database were identified using BLAST programs (Altschul et al. 1990) located on a Nestlé server.

Example 2

Isolation and Characterization of *Coffea* cDNA Clones Encoding Caffeic Acid O-Methyltransferase (COMT)

To find cDNA encoding coffee caffeic acid O-methyltransferase, the protein sequences of biochemically-characterized COMT proteins from *Medicago sativa* COMT (GenBank Accession Number AAB46623 (SEQ ID NO: 31), Gowri et al. 1991) and of *Zinnia elegans* COMT (GenBank Accession Number Q43239 (SEQ ID NO: 33), Ye et al. 1995) were used as the query sequences for a BLAST search against the Nestlé/Cornell "unigene" set 5 using the tblastn algorithm. The first search with the *M. sativa* COMT protein sequence uncovered 8 unigenes: #123802 (e value=e-165), #131937 (e value=1e-72), #120178 (e value=2e-63), #128376 (e value=1e-55), #120387 (e value=1e-35), #128163 (e value=2e-28), #127201 (e value=5e-24), and #120390 (e value=1e-23). These unigenes exhibited relatively high levels of homology. The second search with COMT from *Zinnia elegans* (SEQ ID NO: 33) uncovered the same 8 unigenes: #123802 (e value=e-159), #131937 (e value=7e-67), #120178 (e value=2e-60), #128376 (e value=2e-54), #120387 (e value=1e-32), #128163 (e value=1e-27), #120390 (e value=2e-23) and #127201 (e value=6e-22).

*Coffea canephora* CcCOMT1 (full ORF). A cDNA representing the 5' end of the unigene #123802 (pcccs46w17j22) potentially encoding a complete ORF for COMT was isolated from the 46 weeks grain library (46 weeks after flowering), and fully sequenced. The insert of pcccs46w17j22 (SEQ ID NO: 1) was found to be 1314 bp long and to encode a complete ORF sequence of 1053 bp, which was called CcCOMT1 (SEQ ID NO: 1). The deduced protein sequence (SEQ ID NO: 15) has 350 amino acids, and a predicted molecular weight of 38.26 kDa. A manually optimized alignment of the deduced protein sequence (SEQ ID NO: 15) encoded by peccs46w17j22 (SEQ ID NO: 1) was performed with the COMT protein sequences CcCOMTfruit from *Coffea canephora* (GenBank Accession Number AAN03727) (SEQ ID NO: 29), CcCOMTleaf from *Coffea canephora* (GenBank Accession Number AAN03726) (SEQ ID NO: 30), MsCOMT from *Medicago sativa* (GenBank Accession Number AAB46623 (SEQ ID NO: 31), biochemical and crystallographic information available (Zubieta et al., 2002)), NtCOMT form *Nicotiana tabacum* (GenBank Accession Number AAL91506) (SEQ ID NO: 32), and ZeCOMT from *Zinnia elegans* (GenBank Accession Number Q43239) (SEQ ID NO: 33).

The alignment demonstrates that CcCOMT1 protein (SEQ ID NO: 15) shares 100% and 99.5% and 75.8% and 57.4% and 75.3% identity with the protein sequences CcCOMTfruit, CcCOMTleaf, MsCOMT, NtCOMT, and ZeCOMT (SEQ ID NOs: 29, 30, 31, 32, and 33) noted above, respectively (FIG. 2), and supports the initial annotation of pcccs46w17j22 (SEQ ID NO: 1) as a *C. canephora* caffeic acid O-methyltransferase. Moreover, this alignment and the identity between peccs46w17j22 (SEQ ID NO: 1) and the two coffee COMT sequences: CcCOMTfruit and CcCOMTleaf suggest that those are allelic sequence.

The alignment also demonstrates that the CcCOMT1 protein (SEQ ID NO: 15) contains almost all (except one) of the amino acid residues which have been identified by Zubieta, (Zubieta et al. 2002) who determined the structure of the alfalfa caffeic acid O-methyltransferase by x-ray crystallography to a) interact in SAM recognition, b) be involved in substrate recognition, and c) be involved in catalytic reaction. This alignment data also indicates that pcccs46w17j22 (SEQ ID NO: 1) encodes a full length cDNA for a *C. canephora* Caffeoyl CoA O-methyltransferase.

*Coffea canephora* CcCOMT2p (partial ORF). A cDNA representing the 5' end of the unigene #131937 (pcccl21n18) potentially encoding a partial ORF for COMT was isolated from the leaf library and fully sequenced. The partial sequence obtained for pcccl21n18 is 893 bp long and encodes a partial ORF sequence. The first 96 bp of this cDNA (5' end) appears to contain an intron sequence because this sequence does not match the homologous proteins, and has no homologs in the GenBank database. The partial ORF of pcccl21n18 is 672 bp long and was called CcCOMT2p (SEQ ID NO: 2). The deduced partial protein sequence (SEQ ID NO: 16) is a polypeptide of 223 amino acids, having a predicted molecular weight of 24.66 kDa.

Based on a sequence alignment with the complete ORF of CcCOMT1 (350 aa) (SEQ ID NO: 15), it was assumed that the CcCOMT2p protein (SEQ ID NO: 16) was missing over 127 amino acids at the N-terminal end. A manually optimized alignment of the deduced protein sequence encoded by pcccl21n18 was performed with the COMT protein sequences CcCOMTfruit from *Coffea canephora* (GenBank Accession Number AAN03727), CcCOMTleaf from *Coffea canephora* (GenBank Accession Number AAN03726), MsCOMT from *Medicago sativa* (GenBank Accession Number AAB46623), NtCOMT form *Nicotiana tabacum* (GenBank Accession Number AAL91506), and ZeCOMT from *Zinnia elegans* (GenBank Accession Number Q43239) (SEQ ID NOs: 29, 30, 31, 32, and 33).

Figure 2:
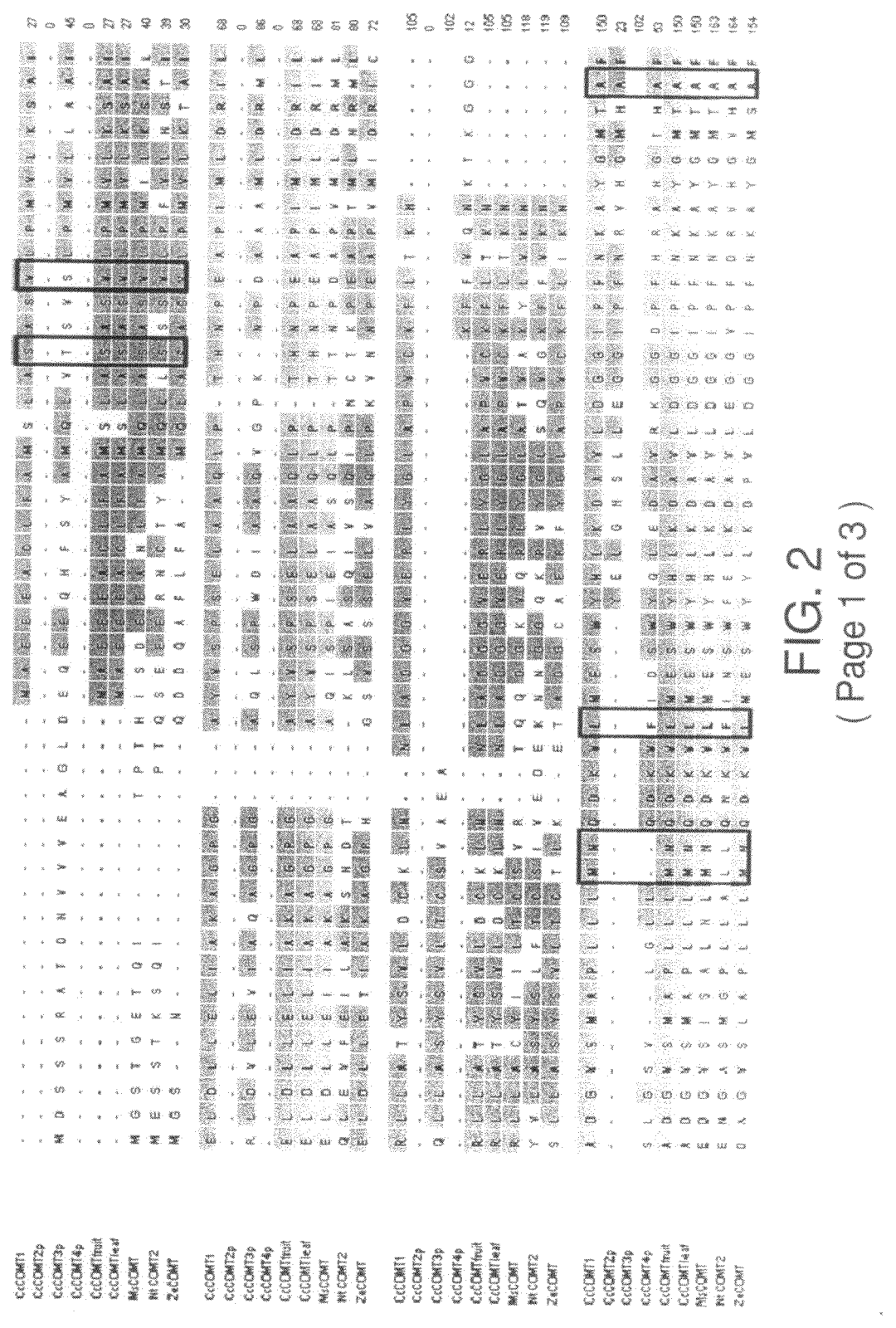
Figure 2:
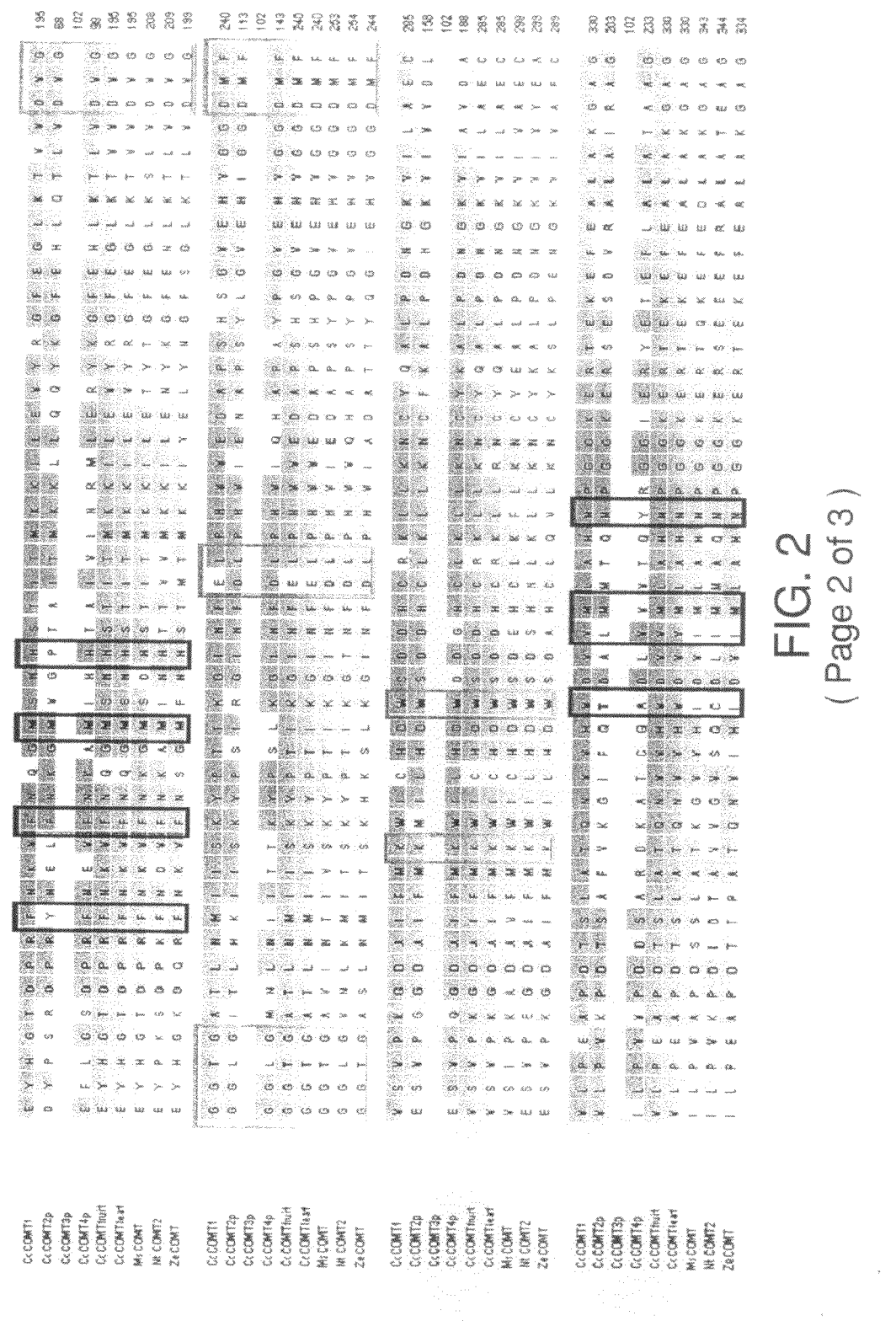
Figure 2:
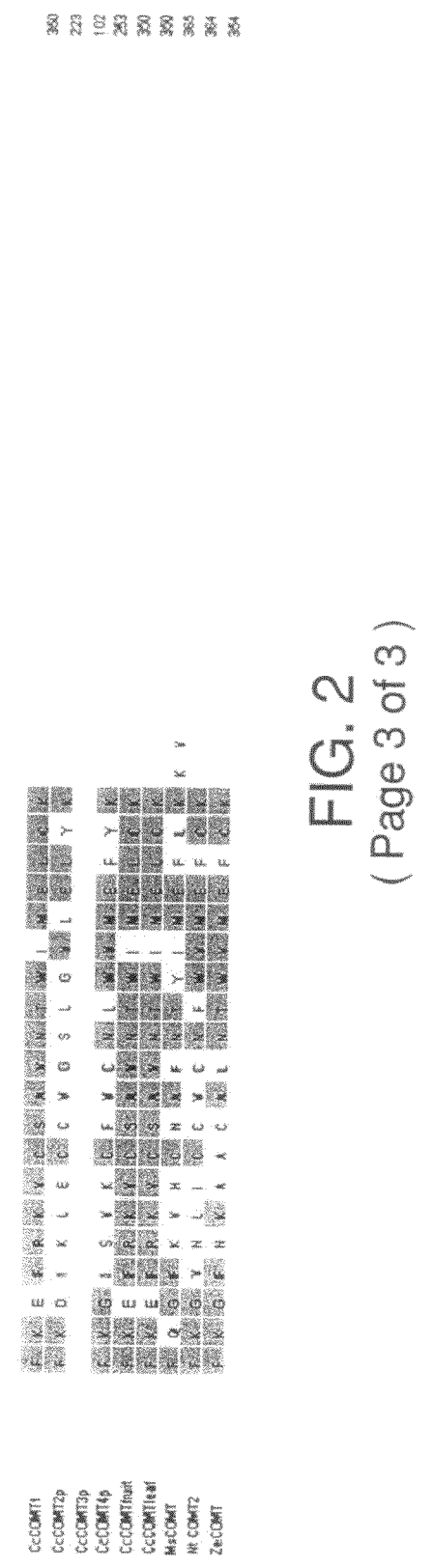

This alignment demonstrates that CcCOMT2p protein (SEQ ID NO: 16) shares 41.7%, 42.6%, 38.2%, 42.9%, and 38.9% identity with the protein sequences CcCOMTfruit, CcCOMTleaf, MsCOMT, NtCOMT, and ZeCOMT (SEQ ID NOs: 29, 30, 31, 32, and 33) noted above, respectively (FIG. 2), and supports the initial annotation of pcccl21n18 (SEQ ID NO: 2) as a *C. canephora* caffeic acid O-methyltransferase. As shown in FIG. 2, six of the characterized sites described in the crystal structure of the alfalfa COMT are different in the *coffea* protein sequence COMT2p. The differences are as follows: a) Four of twelve conserved amino acids that have been determined to be involved in substrate binding (Zubieta et al. 2002), Phe172, His183, Ile316 and Ile319 of MsCOMT (SEQ ID NO: 31) are replaced, respectively, by a Tyr, a Pro, a Thr and a Leu residues in CcCOMT2p (SEQ ID NO: 15), b) one of three catalytic residues (Zubieta et al. 2002), Glu297 is replaced in CcCOMT2p protein (SEQ ID NO: 2) by an Asp residue, and c) two of 14 residues involved in cofactor SAM recognition (Zubieta et al. 2002), Thr211, and Asp231 are replaced in CcCOMT2 protein (SEQ ID NO: 2), respectively, by a Leu and a Glu residue.

*Coffea canephora* CcCOMT3p (partial ORF). A cDNA representing the 5' end of the unigene #120178 (pcccl28d5) potentially encoding a partial ORF for COMT was isolated from the leaf library and partially sequenced at the 5' terminal. The partial sequence obtained for pcccl28d5 is 475 bp long and encodes a partial ORF sequence. The partial ORF of pcccl28d5 (SEQ ID NO: 3) is 309 bp long and was called CcCOMT3p (SEQ ID NO: 3). The deduced partial protein sequence (SEQ ID NO: 17) is a polypeptide of 103 amino acids, having a predicted molecular weight of 10.9 kDa.

Based on an alignment with the complete ORF of CcCOMT1 (350 aa) (SEQ ID NO: 15), it was assumed that the CcCOMT3p protein (SEQ ID NO: 17) was missing over 248 amino acids at the C-terminal end. A manually optimized alignment of the deduced protein sequence (SEQ ID NO: 17) encoded by pcccl28d5 (SEQ ID NO: 3) was performed with the COMT protein sequences CcCOMTfruit from *Coffea canephora* (GenBank Accession Number AAN03727), CcCOMTleaf from *Coffea canephora* (GenBank Accession Number AAN03726), MsCOMT from *Medicago sativa* (GenBank Accession Number AAB46623), NtCOMT form *Nicotiana tabacum* (GenBank Accession Number AAL91506), and ZeCOMT from *Zinnia elegans* (GenBank Accession Number Q43239) (SEQ ID NOs: 29, 30, 31, 32, and 33).

The alignment demonstrates that CcCOMT3p protein (SEQ ID NO: 17) shares 44.3%, 44.3%, 48.1%, 40.6%, and 41.5% identity with the protein sequences CcCOMTfruit, CcCOMTleaf, MsCOMT, NtCOMT, and ZeCOMT (SEQ ID NOs: 29, 30, 31, 32, and 33) noted above, respectively (FIG. 2), and supports the initial annotation of pcccl28d5 (SEQ ID NO: 3) as a *C. canephora* caffeic acid O-methyltransferase.

*Coffea canephora* CcCOMT4p (partial ORF). A cDNA representing the 5' end of the unigene #128376 (pcccp20122) potentially encoding a partial ORF for COMT was isolated from the pericarp library and fully sequenced. The partial sequence obtained for pcccp20122 is 983 bp long and encodes a partial ORF sequence. The partial ORF of pcccp20122 is 762 bp long and was called CcCOMT4p (SEQ ID NO: 4). The deduced partial protein sequence is a polypeptide of 253 amino acids (SEQ ID NO: 18), having a predicted molecular weight of 28.20 kDa.

Based on an alignment with the complete ORF of CcCOMT1 (350 aa) (SEQ ID NO: 14), it was assumed that the CcCOMT4p protein (SEQ ID NO: 18) was missing over 97 amino acids at the N-terminal end. A manually optimized alignment of the deduced protein sequence (SEQ ID NO: 18) encoded by pcccp20122 (SEQ ID NO: 4) was performed with the COMT protein sequences CcCOMTfruit from *Coffea canephora* (GenBank Accession Number AAN03727), CcCOMTleaf from *Coffea canephora* (GenBank Accession Number AAN03726), MsCOMT from *Medicago sativa* (GenBank Accession Number AAB46623), NtCOMT form *Nicotiana tabacum* (GenBank Accession Number AAL91506), and ZeCOMT from *Zinnia elegans* (GenBank Accession Number Q43239) (SEQ ID NOs: 29, 30, 31, 32, and 33).

The alignment demonstrates that CcCOMT4p protein (SEQ ID NO: 18) shares 43.7%, 43.7%, 40.5%, 47.4%, and 42.4% identity with the protein sequences CcCOMTfruit, CcCOMTleaf, MsCOMT, NtCOMT, and ZeCOMT (SEQ ID NOs: 29, 30, 31, 32, and 33) noted above, respectively (FIG.

2), and supports the initial annotation of poccp20122 (SEQ ID NO: 4) as a *C. canephora* caffeic acid O-methyltransferase. As shown in FIG. 2, seven of the characterized sites described in the crystal structure of the alfalfa COMT are different in the *Coffea* protein sequence COMT4p (SEQ ID NO: 18). The differences are as follows: a) Five of twelve conserved amino acids that have been determined to be involved in the substrate binding (Zubieta et al., 2002), Leu136, Ile316, Ile319, Met320 and Asn324 of MsCOMT (SEQ ID NO: 31), are replaced respectively by a Phe, a Ala, a Val, a Val and a Tyr residues in CcCOMT4p (SEQ ID NO: 18); b) one of three catalytic residues (Zubieta et al., 2002), Glu297 is replaced in CcCOMT2p protein (SEQ ID NO: 15) by a Asp residue; and c) two of 14 residues involved in cofactor SAM recognition (Zubieta et al. 2002), Thr211, and Asp231, are replaced in CcCOMT4p protein (SEQ ID NO: 18), respectively, by a Leu and a Glu residue.

Example 3

Isolation and Characterization of a *Coffea canephora* cDNA Clone Encoding Cinnamoyl CoA Reductase (CCR)

To find cDNA encoding coffee Cinnamoyl CoA Reductase, the protein sequences of biochemically-characterized CCR proteins *Eucalyptus gunnii* CCR (GenBank Accession Number T10735 (SEQ ID NO: 34), Lacombe et al. 1997) and of *Triticum aestivum* CCR (GenBank Accession Number AAX08107 (SEQ ID NO: 35), Ma et al. 2005) were used as the query sequences for a BLAST search against the Nestlé/Cornell "unigene" set 5 using the tblastn algorithm. The first search with the *E. gunnii* CCR protein sequence uncovered 1 unigenes #129581 (e value=e-121) exhibiting relatively high levels of homology. The second search with COMT from *Zinnia elegans* uncovered the same unigene #129581 (e value=9e-83).

*Coffea canephora* CeCCR1 (full ORF). The clone A5-1232, which is highly related to Cinnamoyl CoA Reductase from *E. gunnii* and *T. aestivum* (GenBank Accession Number respectively T10735 and AAX08107) (SEQ ID NOs: 34 and 35), was found in the Tours coffee cDNA collection. The insert of pA5-1232 (SEQ ID NO: 5) was found to be 1265 bp long and to encode a complete ORF sequence of 981 bp, which was called CcCCR1 (SEQ ID NO: 5). The deduced protein sequence (SEQ ID NO: 19) is a protein of 326 amino acids, having a predicted molecular weight of 36.31 kDa.

Figure 3:
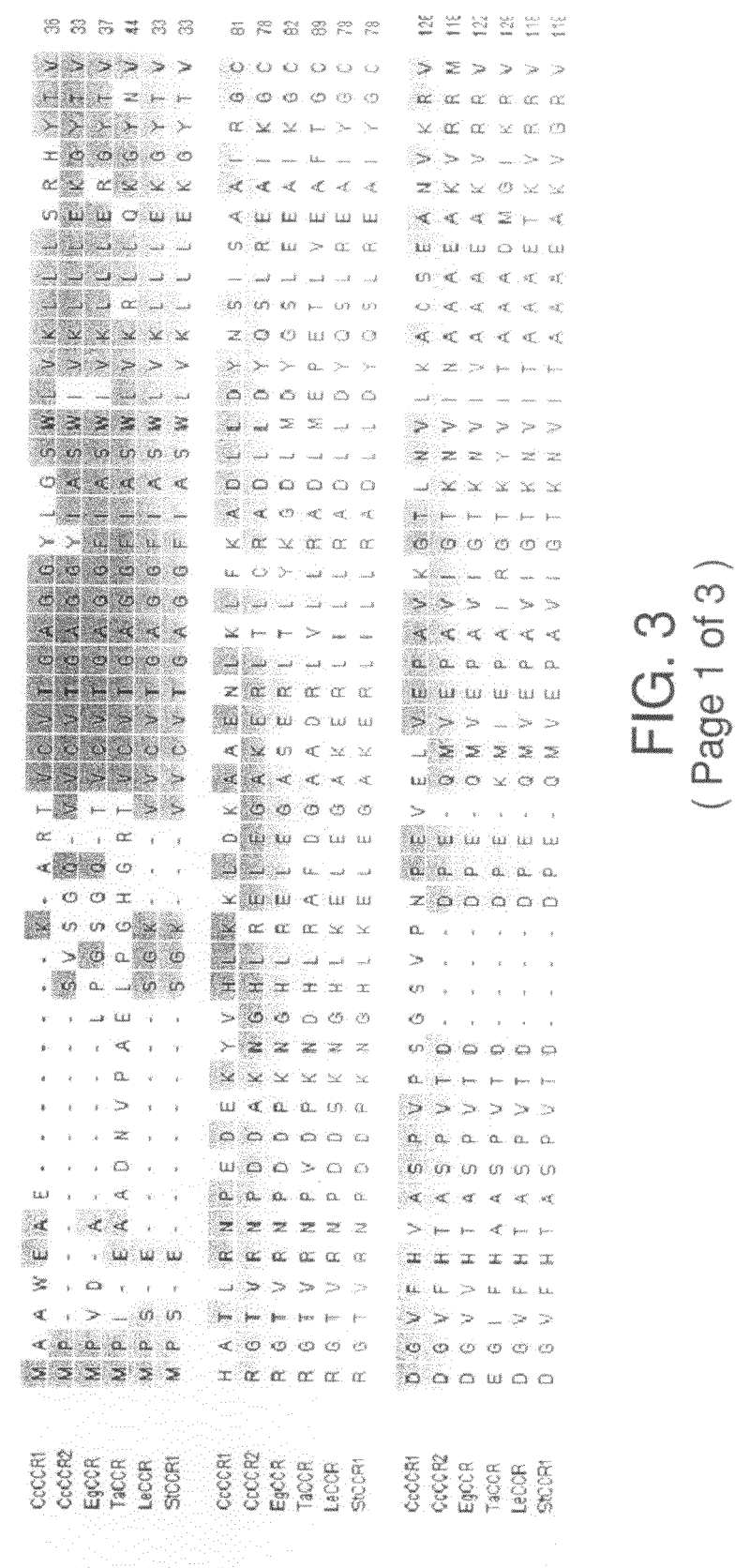
Figure 3:
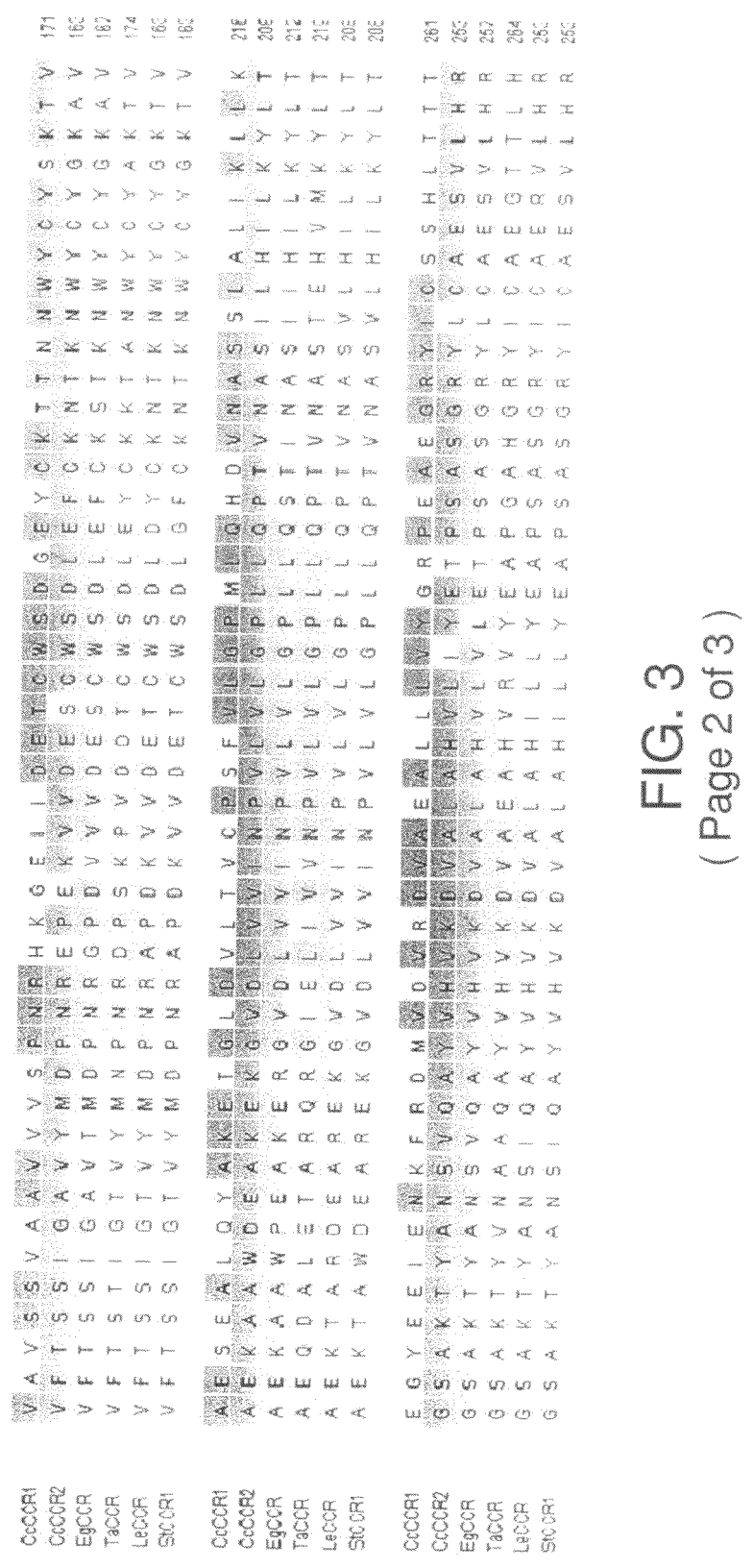
Figure 3:
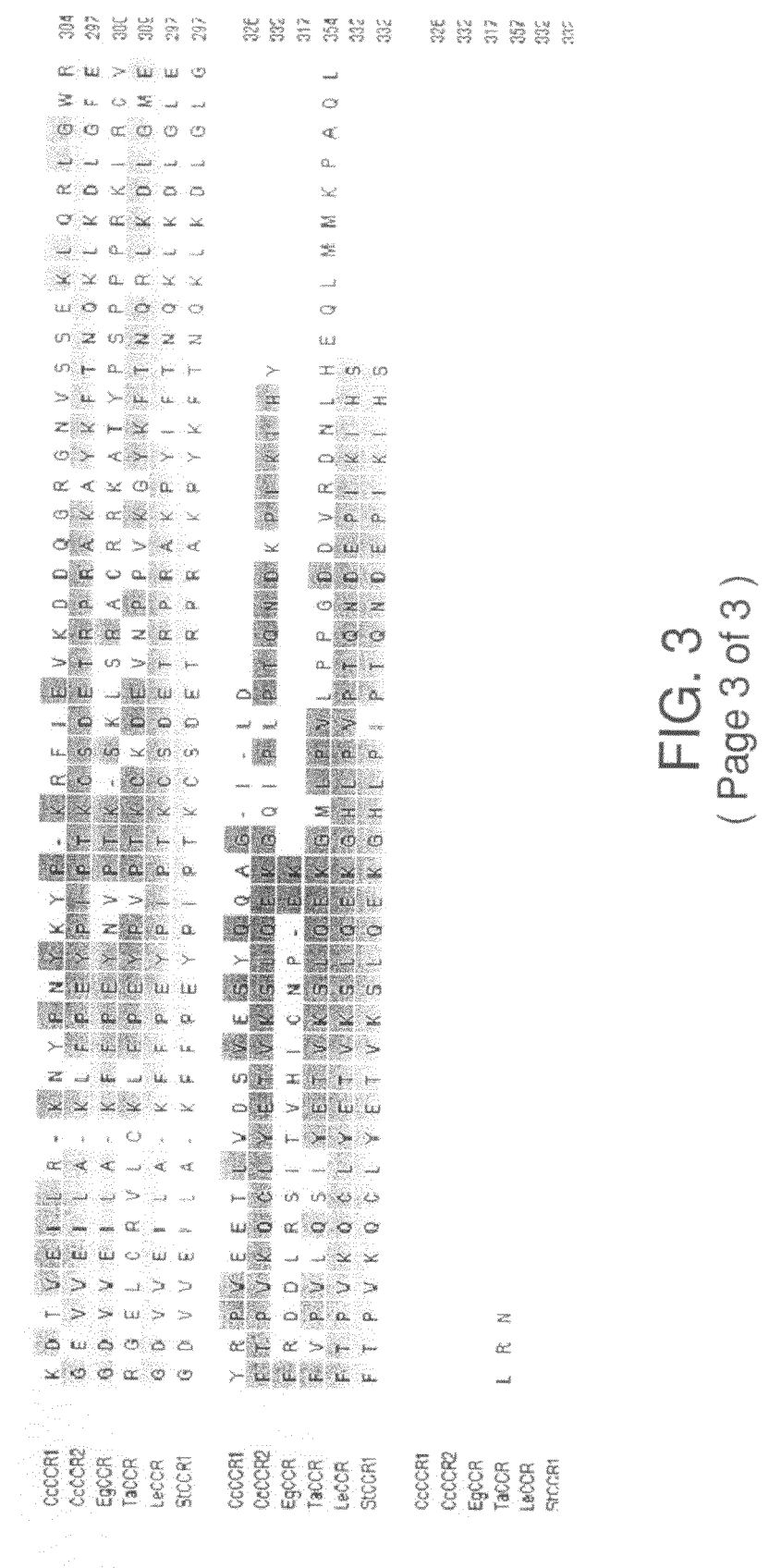

A manually optimized alignment of the deduced protein sequence (SEQ ID NO: 19) encoded by pA5-1232 was performed with the CCR protein sequences EgCCR from *E. gunnii* (GenBank Accession Number T10735), TaCCR from *T. aestivum* (GenBank Accession Number AAX08107), LeCCR from *Lycopersicon esculentum* (GenBank Accession Number AAY41880), and StCCR1 from *Solanum tuberosum* (GenBank Accession Number AAN71761) (SEQ ID NOs: 34, 35, 36, and 37). This alignment shows that CcCCR1 protein (SEQ ID NO: 19) shares 44.4%, 41%, 48.7%, and 48.7% identity with the protein sequences EgCCR, TaCCR, LeCCR, and StCCR1 (SEQ ID NOs: 34, 35, 36, and 37) noted above, respectively (FIG. 3), and supports the initial annotation of pA5-1232 as a *C. canephora* Cinnamoyl CoA Reductase.

*Coffea canephora* CcCCR2 (full ORF). A cDNA representing the 5' end of the unigene #129581 (pcccs46w27k2) potentially encoding a complete ORF for CCR was isolated from the 46 weeks grain library (46 weeks after flowering) and fully sequenced. The insert of pcccs46w27k2 (SEQ ID NO: 6) was found to be 1354 bp long and to encode a complete ORF sequence of 999 bp, which was called CcCCR2 (SEQ ID NO: 6). The deduced protein sequence (SEQ ID NO: 20) is a protein of 332 amino acids, having a predicted molecular weight of 36.77 kDa.

A manually optimized alignment of the deduced protein sequence (SEQ ID NO: 20) encoded by pcccs46w27k2 (SEQ ID NO: 6) was performed with the CCR protein sequences EgCCR from *E. gunnii* (GenBank Accession Number T10735), TaCCR from *T. aestivum* (GenBank Accession Number AAX08107), LeCCR from *Lycopersicon esculentum* (GenBank Accession Number AAY41880), and StCCR1 from *Solanum tuberosum* (GenBank Accession Number AAN71761) (SEQ ID NOs: 34, 35, 36, and 37). This alignment shows that CcCCR2 protein (SEQ ID NO: 6) shares 77.8%, 61.4%, 87.7%, 88.6% identity with the protein sequences EgCCR, TaCCR, LeCCR, and StCCR1 (SEQ ID NOs: 34, 35, 36, and 37) noted above, respectively (FIG. 3), and supports the initial annotation of pcccs46w27k2 as a *C. canephora* Cinnamoyl CoA Reductase.

Example 4

Isolation and Characterization of *Coffea* cDNA Clones Encoding Cinnamyl Alcohol Dehydrogenase (CAD)

To find cDNA encoding coffee cinnamyl alcohol dehydrogenase, the protein sequences of biochemically characterized CAD protein *Eucalyptus gunnii* CAD (GenBank Accession Number CAA61275 (SEQ ID NO: 38), Goffner et al. 1998) was used as the query sequences for a BLAST search against the Nestlé/Cornell "unigene" set 5 using the tblastn algorithm. The first search with the *E. gunnii* CAD protein sequence uncovered 12 unigenes: #119696 (e value=5e-74), #125019 (e value=2e-71), #119457 (e value=3e-69), #124026 (e value=6e-53), #122110 (e value=1e-47), #129581 (e value=5e-42), #122897 (e value=2e-36), #132206 (e value=3e-32), #129285 (e value=2e-28), #122851 (e value=3e-27), #121958 (e value=2e-23), and #126600 (e value=8e-20). The unigenes exhibit relatively high levels of homology.

A blast (NestleBLAST) search of these 12 DNA sequences against the NCBI Non_Redundant_Protein Bank eliminated 5 unigenes not coding for CAD proteins. The search with the unigenes #124026, #129581 and #121958 indicated that they potentially code for Cinnamoyl CoA Reductase. The search with the Unigene #122897 indicated that it potentially encodes a dihydroflavonol 4 reductase. The search with the Unigene #122851 indicated that it potentially encodes an anthocyanin reductase.

*Coffea canephora* CcCAD1ap (partial ORF). A cDNA representing the 5' end of the unigene #119696 (pcccs18w7121) potentially encoding a partial ORF for CAD was isolated from the 18 weeks grain library (18 weeks after flowering) and fully sequenced. The partial sequence obtained for pcccs18w7121 is 843 bp long and encodes a partial ORF sequence. The nucleotides C at position 237 and A at position 238 appear to be an insertion sequence because this sequence does not match the sequence from homologous proteins, and they generate a shift of the ORF that generates a chimeric protein sequence with no homologous sequence in the GenBank database.

The partial ORF of pcccs18w7121 (CA insertion sequence removed) is 516 bp long and was called CcCAD1ap (SEQ ID NO: 7). The deduced partial protein sequence (SEQ ID NO:

21) reveals a polypeptide of 171 amino acids, having a predicted molecular weight of 18.94 kDa.

Figure 4:
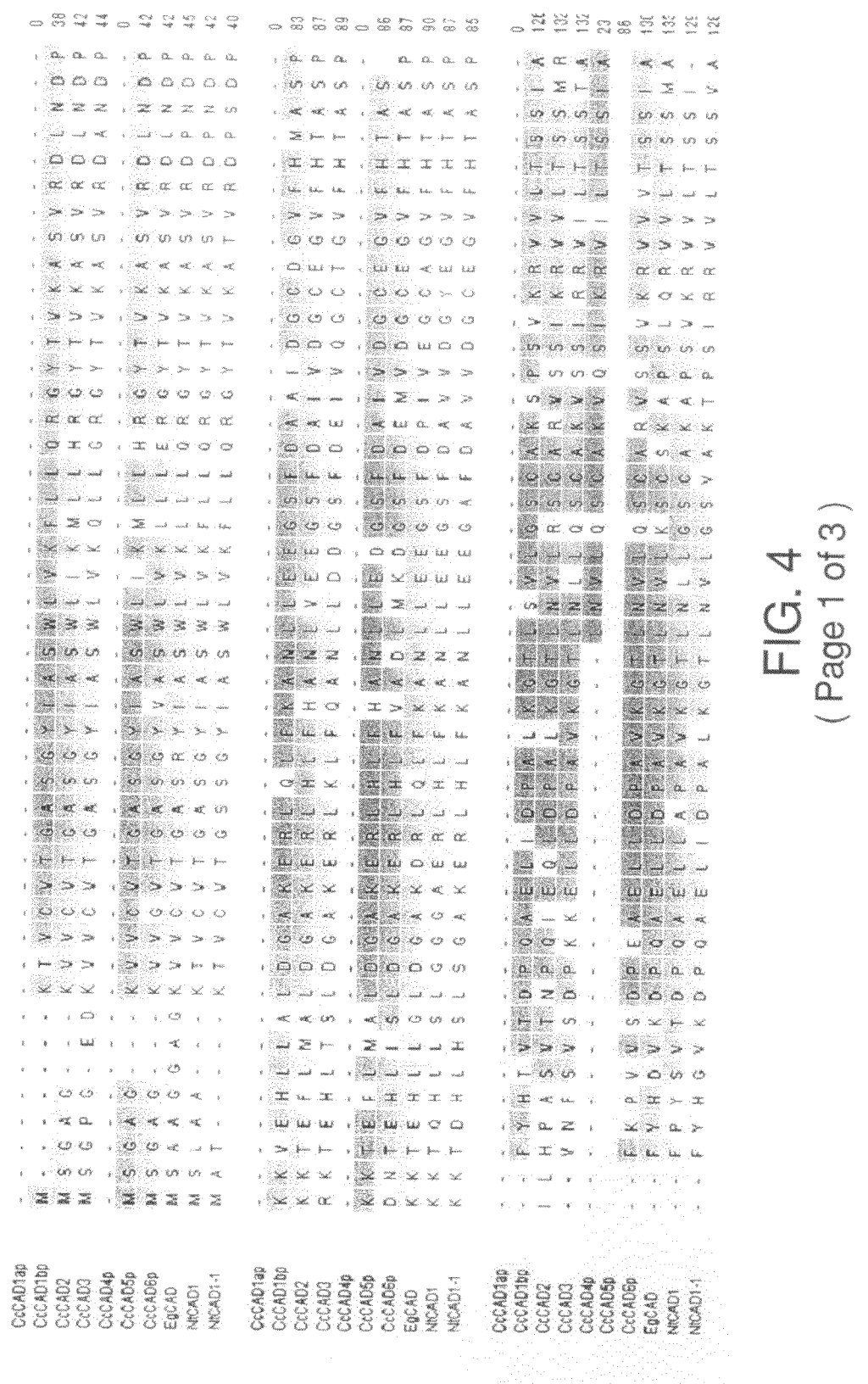
Figure 4:
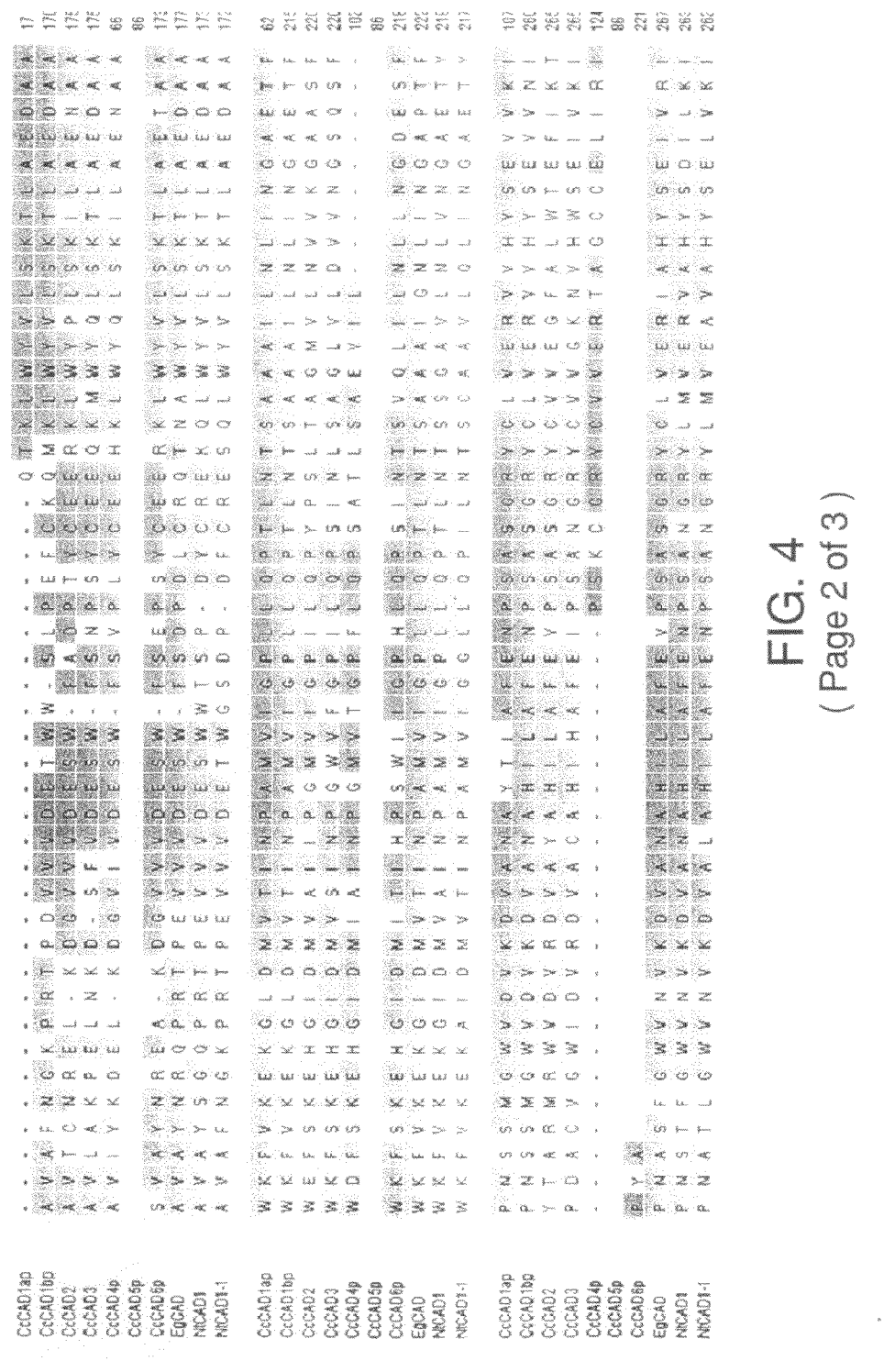
Figure 4:
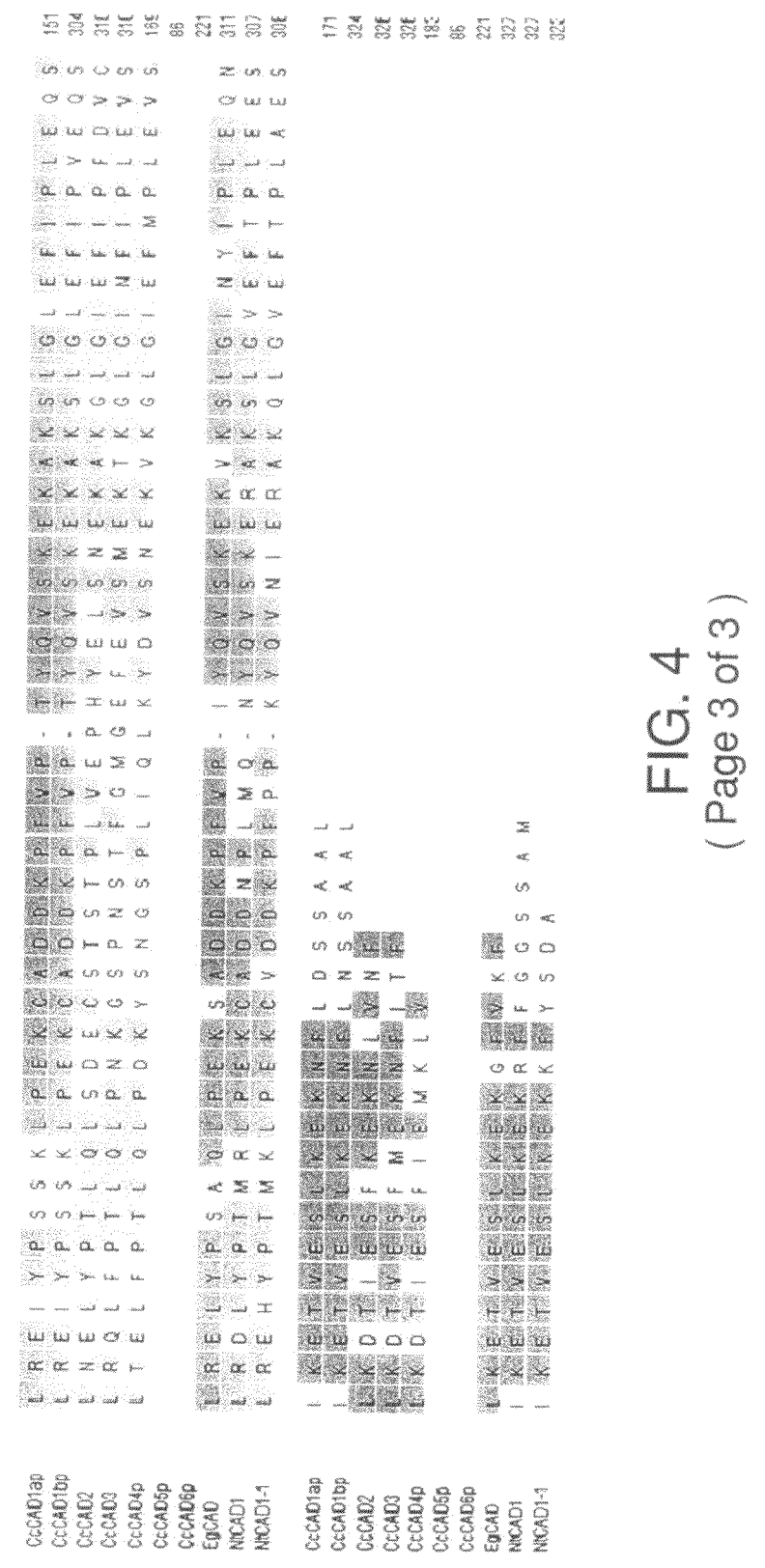

Based on an alignment with the complete protein sequence of EgCAD (327 aa) (SEQ ID NO: 38), it was assumed that the CcCAD1ap protein (SEQ ID NO: 21) was missing over 156 amino acids at the N-terminal end. A manually optimized alignment of the deduced protein sequence (SEQ ID NO: 21) encoded by pcccs18w7121 (SEQ ID NO: 7) was preformed with the CAD protein sequences EgCAD from *Eucalyptus gunnii* (GenBank Accession Number CAA61275), NtCAD1 from *Nicotiana tabacum* (GenBank Accession Number AAX15956), and NtCAD1-1 from *Nicotiana tabacum* (GenBank Accession Number AAX15955) (SEQ ID NOs: 38, 39, and 40). This alignment demonstrates that CcCAD1ap protein (SEQ ID NO: 7) shares 42.3% and 40.6% and 40.1% identity with the protein sequences EgCAD, NtCAD1, and NtCAD1-1 (SEQ ID NOs: 38, 39, and 40) noted above, respectively (FIG. 4), and supports the initial annotation of pcccs18w7121 as a *C. canephora* cinnamyl alcohol dehydrogenase.

*Coffea canephora* CcCAD1b (full ORF). A cDNA representing the 5' end of the unigene #129285 (pcccl29e10) potentially encoding a complete ORF for CAD was isolated from the leaf library and fully sequenced. The sequence obtained for pcccl29e10 is 1457 bp long and encodes a complete ORF sequence. A nucleic alignment between pcccl29e10 and pcccs18w7121 demonstrated that the two have 98.4% identity (95.9% at protein level) in their overlapping regions, and indicates that the two clones are alleles. The complete ORF of pcccl29e10 is 975 bp long and was called CcCAD1b (SEQ ID NO: 8). The deduced protein sequence (SEQ ID NO: 22) is a protein of 324 amino acids, having a predicted molecular weight of 35.53 kDa.

A manually optimized alignment of the deduced protein sequence encoded by pcccl29e10 was performed with the CAD protein sequences EgCAD from *Eucalyptus gunnii* (GenBank Accession Number CAA61275), NtCAD1 from *Nicotiana tabacum* (GenBank Accession Number AAX15956), and NtCAD1-1 from *Nicotiana tabacum* (GenBank Accession Number AAX15955) (SEQ ID NOs: 38, 39, and 40). This alignment demonstrates that CcCAD1b protein (SEQ ID NO: 22) shares 78.2%, 76.1%, and 77.1% identity with the protein sequences EgCAD, NtCAD1, and NtCAD1-1 (SEQ ID NOs: 38, 39, and 40) noted above, respectively (FIG. 4), and supports the initial annotation of pcccl29e10 as a *C. canephora* cinnamyl alcohol dehydrogenase.

*Coffea canephora* CcCAD2 (full ORF). A cDNA representing the 5' end of the unigene #125019 (pcccs46w12g16) potentially encoding a complete ORF for CAD was isolated from the 46 weeks grain library (46 weeks after flowering) and fully sequenced. The sequence obtained for pcccs46w12g16 (SEQ ID NO: 9) is 1521 bp long and encodes a complete ORF sequence. The complete ORF of pcccs46w12g16 is 981 bp long, and was called CcCAD2 (SEQ ID NO: 9). The deduced protein sequence (SEQ ID NO: 23) reveals a protein of 326 amino acids, having a predicted molecular weight of 36.08 kDa.

A manually optimized alignment of the deduced protein sequence (SEQ ID NO: 9) encoded by pcccs46w12g16 (SEQ ID NO: 9) was performed with the CAD protein sequences EgCAD from *Eucalyptus gunnii* (GenBank Accession Number CAA61275), NtCAD1 from *Nicotiana tabacum* (GenBank Accession Number AAX15956), and NtCAD1-1 from *Nicotiana tabacum* (GenBank Accession Number AAX15955) (SEQ ID NOs: 38, 39, and 40). The alignment demonstrates that CcCAD2 protein (SEQ ID NO: 23) shares 61.3%, 60.1%, and 56.5% identity with the protein sequences EgCAD, NtCAD1, and NtCAD1-1 (SEQ ID NOs: 38, 39, and 40) noted above, respectively (FIG. 4), and supports the initial annotation of pcccs46w12g16 as a *C. canephora* cinnamyl alcohol dehydrogenase.

*Coffea canephora* CcCAD3 (full ORF). A cDNA representing the 5' end of the unigene #119457 (pcccp12i20) potentially encoding a complete ORF for CAD was isolated from the pericarp library and partially sequenced. A second search performed in EST Tours databank allowed revealed the same clone A5-602 in the Tours bank, which had already been fully sequenced. The sequence obtained for pA5-602 is 1309 bp long and encodes a complete ORF sequence. The complete ORF of pA5-602 is 981 bp long, and was called CcCAD3 (SEQ ID NO: 10). The deduced protein sequence (SEQ ID NO: 24) is a protein of 326 amino acids, having a predicted molecular weight of 35.74 kDa.

A manually optimized alignment of the deduced protein sequence encoded by pA5-602 was performed with the CAD protein (SEQ ID NO: 24) sequences EgCAD from *Eucalyptus gunnii* (GenBank Accession Number CAA61275) (SEQ ID NO: 38), NtCAD1 from *Nicotiana tabacum* (GenBank Accession Number AAX15956) (SEQ ID NO: 39), and NtCAD1-1 from *Nicotiana tabacum* (GenBank Accession Number AAX15955) (SEQ ID NO: 40). This alignment demonstrates that CcCAD3 protein (SEQ ID NO: 24) shares 62.8%, 60.1%, and 57.1% identity with the protein sequences EgCAD, NtCAD1, and NtCAD1-1 (SEQ ID NOs: 38, 39, and 40) noted above, respectively (FIG. 4), and supports the initial annotation of pA5-602 as a *C. canephora* cinnamyl alcohol dehydrogenase.

*Coffea canephora* CcCAD4p (partial ORF). A cDNA representing the 5' end of the unigene #122110 (pcccs30w33j23) potentially encoding a partial ORF for CAD was isolated from 30 weeks grain library (30 weeks after flowering) and fully sequenced. The sequence obtained to date for pcccs30w33j23 is 716 bp long and encodes a partial ORF sequence. A blast against the NCBI_Non_Redundant_Protein Bank revealed a deletion of 120 bp in the sequence at the position 309. The deletion results in a shift of the ORF and results in a chimeric protein sequence having no homologs in the GenBank database.

The partial ORF of pcccs30w33j23 (a N have been inserted at position 309) is 554 bp long and was called CcCAD4p (SEQ ID NO: 11). The deduced partial protein sequence (SEQ ID NO: 25) is a polypeptide of 183 amino acids, having a predicted molecular weight of 20.46 kDa. Based on an alignment with the complete protein sequence of EgCAD (327 aa) (SEQ ID NO: 38), it was assumed that the CcCAD4p protein (SEQ ID NO: 25) was missing over 108 amino acids at the N-terminal end. A manually-optimized alignment of the deduced protein sequence (SEQ ID NO: 25) encoded by pcccs30w33j23 (SEQ ID NO: 11) was performed with the CAD protein sequences EgCAD from *Eucalyptus gunnii* (GenBank Accession Number CAA61275) (SEQ ID NO: 38), NtCAD1 from *Nicotiana tabacum* (GenBank Accession Number AAX15956) (SEQ ID NO: 39), and NtCAD1-1 from *Nicotiana tabacum* (GenBank Accession Number AAX15955) (SEQ ID NO: 40). This alignment demonstrates that CcCAD4p protein (SEQ ID NO: 25) shares 31.6%, 31.6%, and 29.8% identity with the protein sequences EgCAD, NtCAD1, and NtCAD1-1 (SEQ ID NOs: 38, 39, and 40) noted above, respectively (FIG. 4), and supports the initial annotation of pcccs30w33j23 as a *C. canephora* cinnamyl alcohol dehydrogenase.

*Coffea canephora* CcCAD5p (partial ORF). A cDNA representing the 5' end of the unigene #132206

(pcccwc22w11c3) potentially encoding a partial ORF for CAD was isolated from the 22 weeks wholes cherries library (22 weeks after flowering) and partially sequenced in 5' terminal. The sequence obtained for pcccwc22w11c3 sequence is 744 bp long and encodes a partial ORF sequence. A blast against the NCBI_Non_Redundant_Protein Bank revealed an intron at position 539 through the end of the partial sequence. The presence of the intron in the ORF generates a chimeric protein sequence having no homologs in the GenBank database.

The partial ORF of pcccwc22w11c3 (intron removed) is 258 bp long and was called CcCAD5p (SEQ ID NO: 12). The deduced partial protein sequence (SEQ ID NO: 26) is 86 amino acids, and has a predicted molecular weight of 9.28 kDa. Based on an alignment with the complete protein sequence of EgCAD (327 aa) (SEQ ID NO: 38), it was assumed that the CcCAD5p protein (SEQ ID NO: 26) was missing over 241 amino acids at the C terminal-end. A manually optimized alignment of the deduced protein sequence (SEQ ID NO: 26) encoded by pcccwc22w11c3 was performed with the CAD protein sequences EgCAD from *Eucalyptus gunnii* (GenBank Accession Number CAA61275) (SEQ ID NO: 38), NtCAD1 from *Nicotiana tabacum* (GenBank Accession Number AAX15956) (SEQ ID NO: 39), and NtCAD1-1 from *Nicotiana tabacum* (GenBank Accession Number AAX15955) (SEQ ID NO: 40). This alignment demonstrates that CcCAD5p protein (SEQ ID NO: 26) shares 78.7%, 79.8%, and 76.4% identity with the protein sequences EgCAD, NtCAD1, and NtCAD1-1 (SEQ ID NOs: 38, 38, and 40) noted above, respectively (FIG. 4), and supports the initial annotation of pcccwc22w11c3 as a *C. canephora* cinnamyl alcohol dehydrogenase.

*Coffea canephora* CcCAD6p (partial ORF). A cDNA representing the 5' end of the unigene #126600 (pcccp6j18) potentially encoding a partial ORF for CAD was isolated from pericarp library and partially sequenced at the 5' terminus. The sequence obtained for pcccp6j18 sequence is 697 bp long and encodes a partial ORF sequence. The partial ORF of pcccp6j18 is 664 bp long and was called CcCAD6p (SEQ ID NO: 13). The deduced partial protein sequence (SEQ ID NO: 27) is a polypeptide of 221 amino acids, having a predicted molecular weight of 24.14 kDa.

Based on an alignment with the complete protein sequence of EgCAD (327 aa) (SEQ ID NO: 38), it was assumed that the CcCAD6p protein (SEQ ID NO: 13) was missing over 106 amino acids at the C-terminal end. A manually optimized alignment of the deduced protein sequence (SEQ ID NO: 27) encoded by pcccp6j18 (SEQ ID NO: 13) was performed with the CAD protein sequences EgCAD from *Eucalyptus gunnii* (GenBank Accession Number CAA61275) (SEQ ID NO: 38), NtCAD1 from *Nicotiana tabacum* (GenBank Accession Number AAX15956) (SEQ ID NO: 39), and NtCAD1-1 from *Nicotiana tabacum* (GenBank Accession Number AAX15955) (SEQ ID NO: 40). This alignment demonstrates that CcCAD6p protein (SEQ ID NO: 27) shares 68.0%, 67.1%, and 62.7% identity with the protein sequences EgCAD, NtCAD1, and NtCAD1-1 (SEQ ID NOs: 38, 39, and 40) noted above, respectively (FIG. 4), and supports the initial annotation of pcccp6j18 as a *C. canephora* cinnamyl alcohol dehydrogenase.

Example 5

Isolation and Characterization of a *Coffea canephora* cDNA Clone Encoding Ferulate 5-Hydroxylase (F5H)

To find cDNA encoding coffee ferulate-5-hydroxylase, the protein sequences of biochemically-characterized F5H proteins *Arabidopsis thaliana* F5H (GenBank Accession Number AAD11580 (SEQ ID NO: 41), Ruegger et al. 1999) was used as the query sequences for a BLAST search against the Nestlé/Cornell unigene set 5 using the tblastn algorithm. The first search with the *A. thaliana* sequence uncovered 4 unigenes, #120597 (e value=2e-91), #125120 (e value=1e-90), #124806 (e value=2e-68), and #128806 (e value=7 e-65), exhibiting relatively high levels of homology.

A blast (NestleBLAST) of these 4 DNA sequences against the NCBI Non_Redundant Protein Bank eliminated 3 unigenes that do not encode a F5H protein. The search with the unigenes #120597 and #125120 indicated that they potentially encode Cinnamoyl CoA Reductase. The search with unigene #122897 indicated that it potentially encodes cytochrome P450 type protein. The search with unigene #124806 indicated that it potentially encodes hydroxylase like cytochrome P450 type protein and thus was investigated further.

*Coffea canephora* CcF5Hp (partial ORF). A cDNA representing the 5' end of the unigene #128806 (pcccl18j3) that potentially encoded a partial ORF for F5H was isolated from the leaf library and fully sequenced. The insert of pcccl18j3 was found to be 934 bp long and to encode a partial ORF sequence of 654 bp, which was called CcF5Hp (SEQ ID NO: 14). The deduced protein sequence (SEQ ID NO: 28) shows a protein of 217 amino acids, having a predicted molecular weight of 24.83 kDa.

Figure 5:
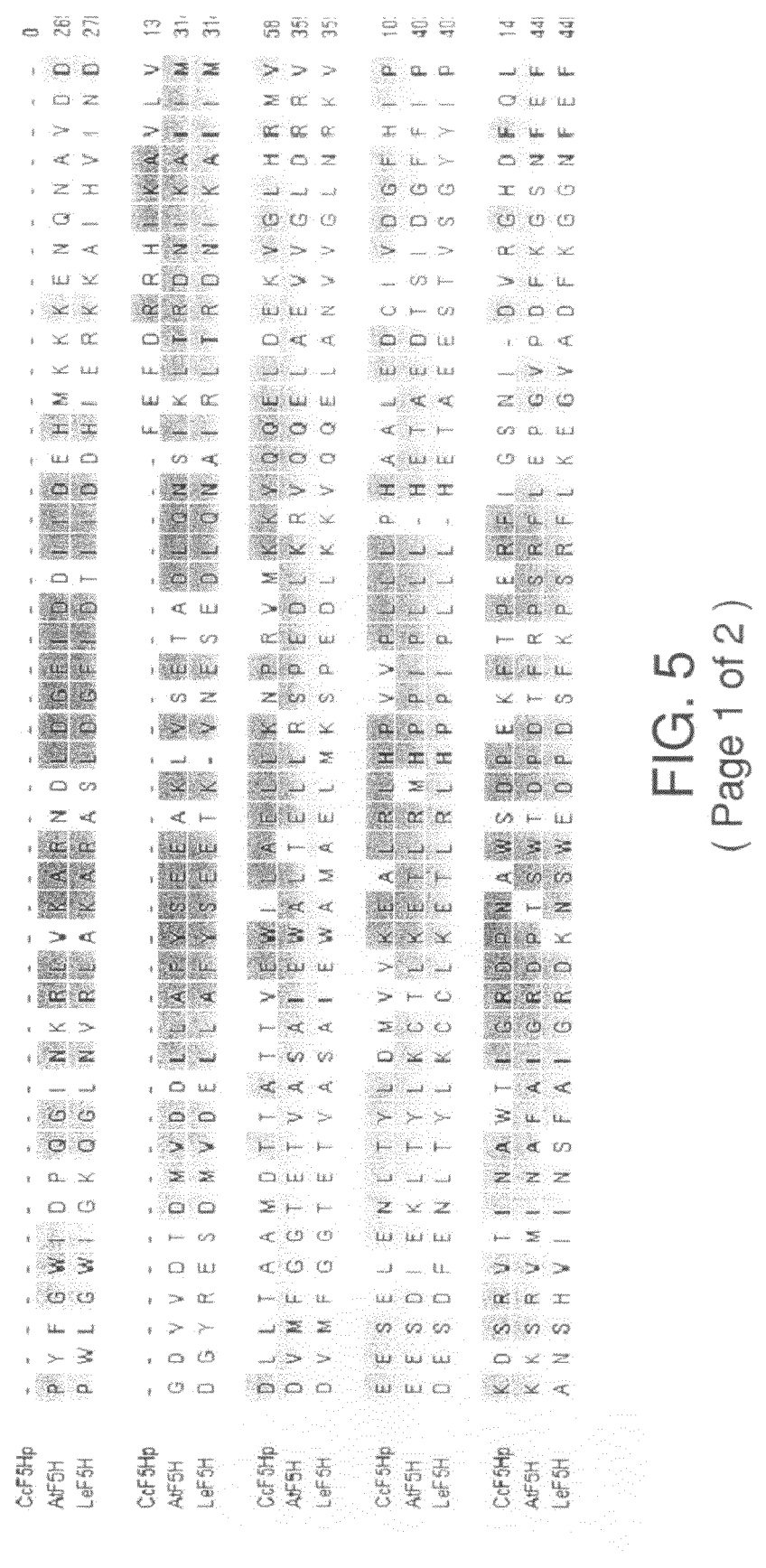
Figure 5:
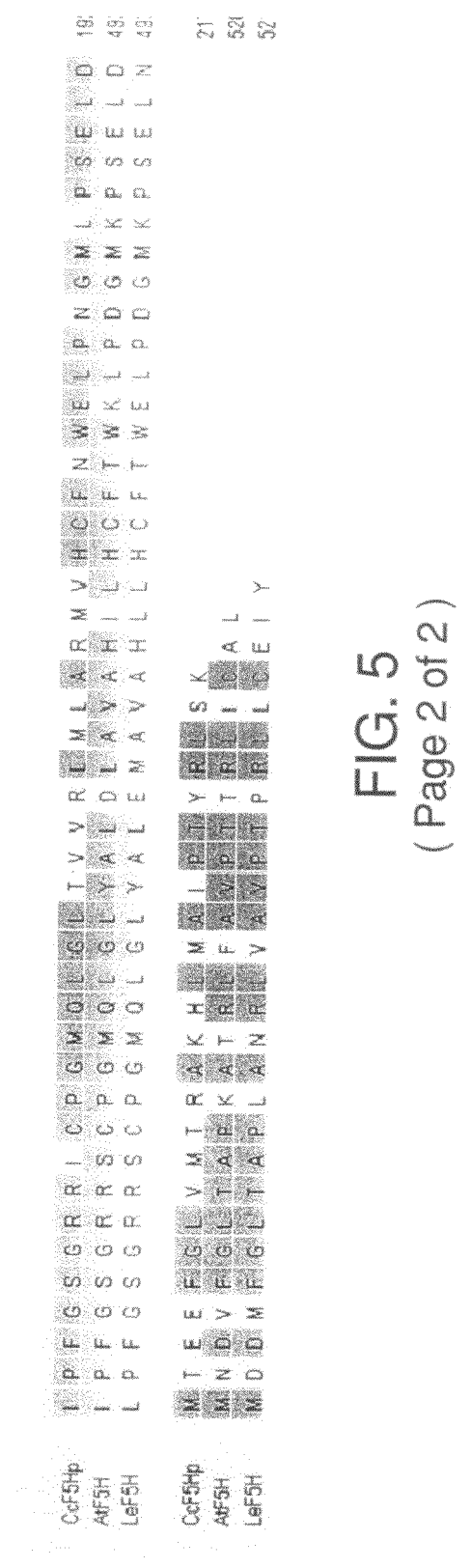

A manually optimized alignment of the deduced protein sequence (SEQ ID NO: 28) encoded by pcccl18j3 (SEQ ID NO: 14) was performed with the F5H protein sequences AtF5H from *Arabidopsis thaliana* (GenBank Accession Number AAD11580) (SEQ ID NO: 41), and LeF5H from *Lycopersicon esculentum* (GenBank Accession Number AAD37433) (SEQ ID NO: 42). This alignment demonstrates that CcF5Hp protein (SEQ ID NO: 28) shares 53% and 50% identity with the overlapping region of protein sequences AtF5H, and LeF5H (SEQ ID NOs: 41 and 42) noted above, respectively (FIG. 5), and supports the initial annotation of pcccl18j3 as a *C. canephora* ferulate-5-hydroxylase.

Example 6

Expression of Lignin Genes

The number of ESTs associated with a particular unigene gives an estimation of the expression level of the associated gene in each library (in each tissue). Therefore, an examination of the number of ESTs within the different unigenes of the lignin genes discussed above can give a broad overview of the expression of these genes. All the unigenes discussed herein, and the number of ESTs in each library for these unigenes, are provided in Table 1.

TABLE 1

In silico distribution of ESTs in the unigenes.

| Gene | Cornell Bank in silico expression | | | | | | |
|---|---|---|---|---|---|---|---|
| | cccl | cccp | ccc22wc | cccs18w | cccs30w | cccs42w | cccs46w |
| CcCOMT1 | | | | | | | 3 |
| CcCOMT2p | 1 | | | | | | |
| CcCOMT3p | 1 | | 1 | | | | |
| CcCOMT4p | 1 | | | | | | |
| CcCCR1 | | | 1 | | | | |
| CcCCR2 | | | | | | | 1 |
| CcCAD1ap | | | | 1 | 2 | | 1 |
| CcCAD1b | 1 | | | | | | |
| CcCAD2 | | | | | 2 | | 2 |
| CcCAD3 | | | 1 | | | | |
| CcCAD4p | | | | | 2 | | |
| CcCAD5p | | | 1 | | | | |
| CcCAD6p | | 1 | | | | | |
| F5H | 1 | | | | | | |

Table 1. The number of ESTs found for each gene are presented in relation to the libraries in which these ESTs were found.

REFERENCES

Agrawal N, Dasaradhi P V, Mohmmed A, Malhotra P, Bhatnagar R K, and Mukherjee S K. (2003) RNA interference: biology, mechanism, and applications. *Microbiol. Mol. Biol. Rev.* 67:657-85.

Boerjan W, Ralph J, and Baucher M. (2003) Lignin biosynthesis. *Annu. Rev. Plant Biol.* 54:519-46.

Brummelkamp T R, Bernards R, and Agami R. (2002) A system for stable expression of short interfering RNAs in mammalian cells. *Science* 296:550-3.

Daglia M, Racchi M, Papetti A, Lanni C, Govoni S, and Gazzani G (2004) In vitro and ex vivo antihydroxyl radical activity of green and roasted coffee, *J. of Agric. Food Chem.* 52: 1700-04.

Delgado-Andrade C, Rufian-Henares J, and Morales F. (2005) Assessing the antioxidant activity of malanoidins from coffee brews by different antioxidant methods. *J. Agric. Food Chem.* 53:7832-6.

Dixon R A, Chen F, Guo D, and Parvathi K. (2001) The biosynthesis of monolignols: a "metabolic grid", or independent pathways to guaiacyl and syringyl units? *Phytochemistry.* 57:1069-84.

Elbashir S M, Harborth J, Weber K, and Tuschl T. (2002) Analysis of gene function in somatic mammalian cells using small interfering RNAs. *Methods* 26:199-213.

Gowri G, Bugos R C, Campbell W H, Maxwell C A and Dixon R A (1991) Molecular cloning and expression of alfalfa S-adenosyl-L-methionine: caffeic acid 3-0-methyltransferase, a key enzyme of lignin biosynthesis *Plant Physiol.* 97:7-14.

Hatfield R, and Vermerris W (2001) Lignin formation in plants. The dilemma of linkage specificity. *Plant Physiol.* 126:1351-57.

Humphreys J M, and Chapple C. (2002) Rewriting the lignin roadmap. *Curr. Opin. Plant Biol.* 5:224-9.

Kim S J, Kim M R, Bedgar D L, Moinuddin S G, Cardenas C L, Davin L B, Kang C, and Lewis N G. (2004) Functional reclassification of the putative cinnamyl alcohol dehydrogenase multigene family in *Arabidopsis. Proc. Natl. Acad. Sci. USA.* 101:1455-60.

Klahre U, Crete P, Leuenberger S A, Iglesias V A, and Meins F (2002) High molecular weight RNAs and small interfering RNAs induce systemic posttranscriptional gene silencing in plants. *Proc. Natl. Acad. Sci. USA.* 99:11981-6.

Logemann E, Reinold S, Somssich I, and Hahlbrock K. (1997) A novel type of pathogen defense-related cinnamyl alcohol dehydrogenase. *Biol. Chem.* 378:909-913.

Marita J M, Vermerris W, Ralph J, and Hatfield R D. (2003) Variations in the cell wall composition of maize brown midrib mutants. *Agric. Food Chem.* 51:1313-21.

Marraccini P, Deshayes A, Pétiard V, and Rogers W J. (1999) Molecular cloning of the complete 11S seed storage protein gene of *Coffea arabica* and promoter analysis in the transgenic tobacco plants. *Plant Physiol. Biochem.* 37:273-282.

Marraccini P, Courjault C, Caillet V, Lausanne F, LePage B, Rogers W, Tessereau S, and Deshayes A. (2003) Rubisco small subunit of *Coffea arabica*: cDNA sequence, gene cloning and promoter analysis in transgenic tobacco plants. *Plant Physiol. Biochem.* 41:17-25.

Meyer K, Cusumano J C, Somerville C, and Chapple C C. (1996) Ferulate-5-hydroxylase from *Arabidopsis thaliana* defines a new family of cytochrome P450-dependent monooxygenases. *Proc. Natl. Acad. Sci. USA.* 93:6869-74.

Piquemal J, Chamayou S, Nadaud I, Beckert M, Barriere Y, Mila I, Lapierre C, Rigau J. Puigdomenech P, Jauneau A, Digonnet C, Boudet A M, Goffner D, and Pichon M. (2002) Down-regulation of caffeic acid o-methyltransferase in maize revisited using a transgenic approach. *Plant Physiol.* 130:1675-85.

Ralph J, Hatfield R D, Piquemal J, Yahiaoui N, Pean M, Lapierre C, and Boudet A M. (1998) NMR characterization of altered lignins extracted from tobacco plants down-regulated for lignification enzymes cinnamylalcohol dehydrogenase and cinnamoyl-CoA reductase. *Proc. Natl. Acad. Sci USA.* 95:12803-8.

Ruegger M, Meyer K, Cusumano J C, and Chapple C. (1999) Regulation of ferulate-5-hydroxylase expression in *Arabidopsis* in the context of sinapate ester biosynthesis. *Plant Physiol.* 119:101-10.

Sibout R, Eudes A, Mouille G, Pollet B, Lapierre C, Jouanin L, and Seguin A. (2005) Cinnamyl Alcohol Dehydrogenase-C and -D are the primary genes involved in lignin biosynthesis in the floral stem of *Arabidopsis. Plant Cell.* 17:2059-76.

Spanier A M, Flores M, Toldra F, Aristoy M C, Bett K L, Bystricky P, and Bland J M (2004) Meat flavor: contribution of proteins and peptides to the flavor of beef. *Adv. Exp. Med. Biol.* 542:33-49.

Tuschl T, and Borkhardt A. (2002) Small interfering RNAs: a revolutionary tool for the analysis of gene function and gene therapy. *Mol. Interv.* 2:158-67.

Vance C, Kirk T, and Sherwood R. (1980) Lignification as a defense mechanism of disease resistance. *Annu. Rev. Phytopathol.* 18:259-88.

Whetten R W, MacKay J J, and Sederoff R R. (1998) Recent advances in understanding lignin biosynthesis. *Annu. Rev. Plant Physiol. Plant Mol. Biol.* 49:585-609.

Wu G, Shortt B, Lawerence E, Leon J, Fitzsimmons K, Levine E, Raskin I, and Shah D. (1997) Activation of Host Defense Mechanisms by Elevated Production of H2O2 in Transgenic Plants *Plant Physiol.* 115:427-35.

Ye Z H and Varner J E (1995) Differential expression of two O-methyltransferases in lignin biosynthesis in *Zinnia elegans Plant Physiol.* 108:459-467.

Yeretzian C, Jordan A, Badoud R, and Lindinger W. (2002) From the green bean to the cup of coffee: investigating coffee roasting by on-line monitoring of volatiles. *Eur. Food Res. Technol.* 214:92-104.

Zubieta C, Kota P, Ferrer J L, Dixon R A, and Noel J P. (2002) Structural basis for the modulation of lignin monomer methylation by caffeic acid/5-hydroxyferulic acid 3/5-O-methyltransferase. *Plant Cell.* 14:1265-77.

The present invention is not limited to the embodiments described and exemplified above, but is capable of variation and modification within the scope of the appended claims.

```
Sequence Listing:
Sequence (SEQ ID NO: 1)
<213> OrganismName: Coffea canephora
<400> PreSequenceString:
accttttcct tcgtcccgga agctttccc ttcaccttg attcctctcc agccaaacaa      60 acctacccc caggacattt ctgatttctg aagctgaagt tggagtaaaa agaaaaagaa     120
atcaaataat ggcagaggag gaagcttgct tattcgccat gagcctggct agtgcatccg    180
tccttcctat ggtactcaaa tcagccatcg aacttgacct cctggagctt atagccaagg    240
ctggtcctgg cgcctacgtc tccccatcgg aactcgccgc acagctcccc acccacaacc    300
cggaagctcc tatcatgctt gatcgcatcc tccgactcct ggccacctac tctgtcctcg    360
attgcaagct caacaatctg gccgatggtg gcgtcgagag gctttacggt ctggcccctg    420
tttgcaaatt cttgaccaag aacgctgatg gtgtgtccat ggcccctctt ttgctcatga    480
atcaagataa ggtcctcatg gaaagctggt atcacttaaa ggatgcggtt cttgatggag    540
gaatcccttt caacaaggcc tacggaatga ctgcattcga atatcacgga accgatccca    600
gattcaacaa ggtgtttaac cagggaatgt ctaatcactc caccattacc atgaagaaga    660
ttttggaagt ttacagaggg tttgagggtc tgaagacggt ggtcgacgtg ggaggtggaa    720
ctggggctac gctcaatatg atcatcagca aatatcccac gatcaagggc atcaactttg    780
agctcccgca cgtcgtagag gacgcccgt ctcattccgg ggtggagcat gtgggtgggg    840
atatgtttgt tagcgtccct aaagggatg ccattttcat gaagtggatt tgccatgatt    900
ggagcgacga ccactgccgg aaactcttga agaactgcta ccaagcactt ccggacaacg    960
ggaaggtgat ccttgccgaa tgtgtccttc cggaagcccc agacacctcg ctcgctactc   1020
agaatgtcgt ccacgttgat gtcgtcatgt tggcccacaa ccctggtggg aagagagga   1080 ctgagaagga attcgaggcc ttggcaaagg gggctggatt caaagaattc cgcaaggttt   1140
gctctgctgt caatacctgg atcatggagc tgtgcaaatg aaggcttact tgcttgaatg   1200 aacccttgt tttgggagac gtcattttt ctcttgcgtg attggattgg tggtttctaa    1260
tcagtatagc cgtctactaa tgaaccttcc ttctgtatta ctattatttc acag         1314
<212> Type: DNA
<211> Length: 1314
SequenceName: CcCOMT1 cDNA Sequence (SEQ ID NO: 2)
<213> OrganismName: Coffea canephora
<400> PreSequenceString:
aaaagatata tcttgcagtt caatgggcta ctacagatca ttggttacag gcatggtgtt      60
tcgatgacaa agactctact tgattttcat ccaatgtatg aacttgggaa ttctttgctt    120
gaaggaggga ttccatttaa tagagttcat ggaatgcacg catttgacta ccctagtaga    180
gatcccaggt ataatgagct tttcaacaag ggaatggttg gtcctacagc cataacaatg    240
aaaaaattgc ttcaacaata taaggatttt gagcaccttc agacattggt tgatgttggt    300
```

-continued

```
ggtggtcttg gaataaccct tcacaagatt atatcaaaat acccttctat aaggggtatc    360
aattttgatc ttccacatgt cattgaaaac gcgccatcct atcttggagt ggaacacatt    420
ggtggagaca tgtttgaaag cgttcctgga ggagatgcta tttttatgaa gatgatactc    480
catgattgga gtgatgatca ctgcttaaag ctgctgaaga actgcttcaa agctctacca    540
gatcatggca aagtcatcgt tgttgatttg gttctacccg taaaacctga tactagtgcc    600
tttgtaaaag gcattttcca gactgatgct ctcatgatga ctcaaaatcc tggagggaaa    660
gagcgatcag aatctgatgt tcgggccttg gctatcagag ctggatttaa agacataaag    720
ttagaatgtt gtgtgggtag tcttggggtc ctggagttgt acaaatagtt atgtctgccc    780
atttggcagg ttttttcattt gaagaaattt cttttgtttg cttgtatttc ttaaataatc    840
tctatttggt ctaatgagcg tagtgttct taaaaaaaaa aaaaaaaaaa aaa             893
<212> Type: DNA
<211> Length: 893
SequenceName: CcCOMT2p partial cDNA Sequence (SEQ ID NO: 3)
<213> OrganismName: Coffea canephora
<400> PreSequenceString:
cttaatcatt tcaaaatttg ccgtcaatga gtggcaatta acacaacccc cacacccaat     60
ccaatatatg ctacagtaca actaatctga atttatatac gtatgaccta gctgggatct    120
atcatcatct acagatttaa gagttaaagg tagtagcagt agtgatatgg attcttcgtc    180
aagagcaacc gacaatgttg ttgttgaagc agggctagat gagcaagaag agcaacactt    240
ctcgtacgcg atgcagctgg tcacctctgt atctttgccc atggtgctgc tggctgccat    300
ccggctcgac gtgttggagg tcattgccca agcgggtcca ggtgcccaat tgtcgccttg    360
ggacattgca gcccaggtag gtcctaaaaa cccagatgcg gctgctatgc tggatagaat    420
gctgcagctc ctggctagct actcggtgct cacctgctct gttgccgagg cggat         475
<212> Type: DNA
<211> Length: 475
SequenceName: CcCOMT3p partial cDNA Sequence (SEQ ID NO: 4)
<213> OrganismName: Coffea canephora
<400> PreSequenceString:
caagttcttt gtacagaaca aaacaaaggg aggaggttca ctaggctccg ttctgggcct     60
gcttcaagat aaggtcttca ttgacagttg gtaccaatta aagatgcag ttcgcaaagg    120 gggagatccg tttcacaggg cgcacggtac acatgcattt gaatttcttg gaagcgaccc    180
cagattcaat gaggtattca acaaggcaat gatccaccac acagctatcg tcataaacag    240
aatgcttgaa cggtacaaag ttttgagca cctcaaaact ttggtagatg ttggtggtgg    300
tcttggaatg aacctcaata taatcacaac taaataccct agtctcaagg gtattaattt    360
tgatttgcca catgttatac aacatgcacc agcctatcct ggtgttgaac atgttggagg    420
agacatgttt gaaagtgttc cacaggggga tgccattttt atgaagtgga tacttcatga    480
ttgggatgat ggtcattgct tgaagctgct gaaaaattgt acaaggctt taccagacaa    540 tggaaaggta atagctgttg acgcaattct tcctgtggtt cctgatgata gtgcacgcga    600
caaagctact tgccaagcag atcttgttgt ggtgactcaa tatagggag gaattgagag    660 atatgaaaca gagtttcttg ccctggctac tgctgctgga tttaaaggca taagtgtgaa    720
atgttttgta tgtaacttgt gggtcatgga gttctataag tagatgactg gttcatgggg    780
cactgtactt taaaacctta aatgttgtat gttgaatgat tgccaatgtc atggtgacta    840
tctgcaatct acaacgagga aaaaaactgc aatattgacc tcgtaagaat aaatttatac    900
attgttttgt ttccgaatat gataattatg atggagttaa ggcaaaaaaa aaaaaaaaaa    960
```

```
aaaaaaaaaa aaaaaaaaaa aaa                                             983
```
<212> Type: DNA
<211> Length: 983
SequenceName: CcCOMT4p partial cDNA Sequence (SEQ ID NO: 5)
<213> OrganismName: *Coffea canephora*
<400> PreSequenceString:

```
aagcagtggt aacaacgcag agtacgcggg gaaccaaaaa agaactaata ctcataataa    60
agaaaagaat aaaactttat ccaccttctt gatcaatcta tagtgaatct ggtactaaaa   120
tactaatccc actactgcta caagtaagca atcagacatg gcagcgtggg aggctgagaa   180
ggccaggaca gtatgtgtta caggagcagg gggatacctg gatcttggt tagtcaagct    240 actcctttcc cgccattata ctgttcatgc caccctcaga aatcccgagg atgagaaata   300
tgttcatctg aagaaacttg acaaagcagc tgagaatttg aaactcttta aggctgattt   360
gctggattac aactccattt ctgcagccat caggggctgt gatggcgtat ttcatgtagc   420
tagtcctgtt ccttcaggct ctgttcccaa tcctgaggtt gaacttgttg agccggctgt   480
aaagggtacc cttaatgtac tgaaggcttg ttctgaagca aatgtcaagc gcgttgtagc   540
tgtttcctct gttgctgctg ttgttgtgag tcctaatcgg cataaaggtg aaattataga   600
tgagacgtgt tggtcagacg gggaatactg caagacaaca aataactggt attgttactc   660
caagacggtt gctgaaagtg aggctttaca atatgcaaaa gaaactggcc ttgatgtttt   720
aactgtatgc ccatcctttg ttctcggccc catgcttcag catgatgtga atgctagcag   780
tctggctctt ataaagctgt tgaagaagg atatgaagaa atagaaaaca aattccggga    840
tatggtagat gtgcgtgatg tggctgaagc actgcttttg gtttacggga gacctgaagc   900
tgaagggcgg tacatatgtt catctcacct cactacgaca aaggatacgg tggaaattct   960
gaggaaaaac tatcccaact ataagtaccc taagagattt atagaggtga aggatgatca  1020
aggccgagga aatgttagct cagaaaaatt gcagaggctg ggctggagat ataggccagt  1080
ggaagaaact cttgttgact ctgtcgaaag ctaccagcag gctgggatct tggattgatc  1140
actttctgcc ttttctgttt ttttgttaat gggacttgtg gattattttg taaaagaatt  1200
tttggatcta ttaaaagtgg aatttgtgct tgtagaaaaa aaaaaaaaaa aaaaaaaaa   1260 aaaaa                                                              1265
```
<212> Type: DNA
<211> Length: 1265
SequenceName: CcCCR1 cDNA Sequence (SEQ ID NO: 6)
<213> OrganismName: *Coffea canephora*
<400> PreSequenceString:

```
cctttgcctt tcattgcaga agaaattttg ttctcgcgcg cagaaatctt ctcattactt    60
accaacctca cgtctcacct aaaccaaaaa gaaagaaaa gaaagaaaaa accaggtcag    120
aagcatgcct tcagtttccg gccaagtcgt ctgtgtcact ggcgccggtg gctacatcgc   180
ttcctggata gttaagctcc tccttgaaaa aggctacact gttagaggaa ctgttagaaa   240
ccctgatgat gcgaagaatg gtcacttgcg ggagctagaa ggagcaaaag agagattgac   300
actatgcaga gctgaccttc ttgattatca gagtttacgt gaagccatca aaggctgtga   360 tggggtttc cacactgctt cccccgttac ggatgatccg gaacaaatgg tggagccagc    420
ggtgattggg accaaaaatg tgatcaacgc agccgccgag gccaaggtcc gcggatggt    480 tttcacctca tcaattggtg cggtttacat ggacccaac agggaacctg aaaaagttgt    540
ggacgagagt tgttggagtg atcttgaatt ctgcaagaat actaagaatt ggtattgcta   600
cgggaaagct gtggcagaaa aagcagcatg ggacgaagcc aaggagaaag gggtggattt   660
```

-continued

```
ggtggtgatc aacccggtgc tggtgttggg accattgttg caaccgaccg tgaatgccag    720
tattcttcat atcctcaaat acttgactgg atctgcaaag acttatgcca actctgtgca    780
ggcctacgtg cacgttaagg atgttgcatt ggcacacgtt cttatctacg agactccctc    840
ggcatctggg agatacctct cgccgagag cgttcttcat cgcggtgaag tggttgaaat    900
cttggccaaa ctctttccgg agtacccaat ccaaccaag tgctccgatg aaacaagacc    960
aagagcaaaa gcttacaagt tcacaaatca gaagctcaag gatttggggt ttgaattcac   1020
accggtgaaa cagtgcctat atgagacggt taaaagtctt caggagaagg ggcagatacc   1080
cctccctact cagaacgata agcccattaa aattcactac tagtctgact ttattctggt   1140
tgctattgat atcaaaatgt tagcttttta tcattgaaga agaagaagta gtagaagtat   1200
aaagaatgtt taaggttgca atccaaatcc gttgcttgtg aaccagaatg tttaaggcag   1260
tagtatttgt gctccagatt tccgtacccg atgtgaagtc tttactacct aaaaaaaaaa   1320
aaaaaaaaaa aaaaaaaaaa aaaaaaaaaa aaaa                               1354
```
<212> Type: DNA
<211> Length: 1354
SequenceName: CcCCR2 cDNA Sequence (SEQ ID NO: 7)
<213> OrganismName: *Coffea canephora*
<400> PreSequenceString:
```
agcaaacgaa gttatggtat gttctctcaa agacattggc tgaggatgct gcctggaagt     60
ttgtaaaaga gaaaggttta gacatggtaa cgataaaccc agctatggtg attgggcctc    120
tgttacagcc aacacttaac accagtgctg ctgcaatttt gaatttaata aacggtgcag    180
aaacatttcc aaattcttct atgggctggg ttgatgtcaa agatgttgct aatgcacata    240
tactatagct tttgaaaatc catctgctag tggaagatac tgcctggtcg aaagagtggt    300
acactactct gaagttgtga agatcttgcg tgaaattat ccttcctcaa aacttccaga    360
aaagtgcgct gatgacaagc catttgtgcc gacgtaccag gtttccaagg agaaggcaaa    420
aagcttaggt cttgaattca ttccccttga gcaaagcatc aaggaaacag ttgaaagctt    480
gaaggagaag aacttttttgg actcttctgc tgcactttga atatcgcccg aaacatgatg    540
aggaacatcg agagttggta gcagtgccta ttgaaaatat gttttccaaa ccctatatg    600 taccaagcct ctctgactga cgttacatgc atccacagag atttagaatc tacatatgaa    660
acaataaagt actcgtcttt tttgctatac tgaaaatttg aacaggaaat atccttttgt    720
gtttcctgct gcaaattcaa ggatatagca atgatgagta gattttagtg cgtaattata    780
tgttggacga gaattataa aatcaaggag cagcattcct tgtaaaaaaa aaaaaaaaaa    840
aaa                                                                   843
```
<212> Type: DNA
<211> Length: 843
SequenceName: CcCAD1ap partial cDNA Sequence (SEQ ID NO: 8)
<213> OrganismName: *Coffea canephora*
<400> PreSequenceString:
```
atcgattacc agaaatgtgt acaaatagac caaaccctta caaaatcttt gtctgttgga     60
acaagatctg tgtttgttgg aacaagaatt cacactctgc actcattttt tcacagaaaa    120
ggcggcaata atgaagacag tgtgtgtaac aggggcttcg ggctacatag catcatggct    180
tgtcaagttc ttgctccagc gtggttacac tgtcaaggca tctgttcgtg acctcaatga    240
tccaaagaaa gtagaacact tgcttgcact tgatggagct aaggagagac ttcagttgtt    300
caaagcaaac ctactggagg aaggttcctt tgatgctgcg attgatggtt gtgatggtgt    360
ttttcatatg gcctctccct tctaccatac agtcactgat cctcaggctg aattgattga    420
```

-continued

```
tcctgctcta aaagggactc ttagtgttct gggatcatgt gcaaaatctc catctgttaa      480
aagagtggtt ttaacatcct ctatagctgc agttgccttc aacggcaagc ctcgtactcc      540
ggacgtggtg gttgatgaga cttggtggtc tcttcctgaa ttttgcaagc aaatgaagtt      600
atggtatgtt ctctcaaaga cattggctga ggatgctgcc tggaagtttg taaaagagaa      660
aggtttagac atggtaacga taaacccagc tatggtgatt gggcctctgt tacagccaac      720
acttaacacc agtgctgctg caattttgaa tttaataaac ggtgcagaaa catttccaaa      780
ttcttctatg ggctgggttg atgtcaaaga tgttgctaat gcacatattc tagcttttga      840
aaatccatct gctagtggaa gatactgcct ggttgaaaga gtggtacact actctgaagt      900
tgtgaacatc ttgcgtgaaa tttatccttc ctcaaaactt ccagaaaagt gcgctgatga      960
caagccattt gtgccgacgt accaggtttc aaggagaag gcaaaaagct taggtcttga     1020
attcattccc gttgagcaaa gcatcaagga aacagttgaa agcttgaagg agaagaactt     1080
tttgaactct tctgctgcac tttgaatatc acccgaaaca tgatgaggaa catcgagagt     1140
tggtagcatt gcctatttaa aatatgttgt ccaaactcct atatgtacca agcccgtctg     1200
actggcgtta catgcatcca cagagattta gaatctacat atgagacaat aaagtactcg     1260
tcttttttgc tatactgaaa atttgaacag gaaatatcct tttgttttc ctgctgcaaa     1320 ttcaaggata tagcaatgat gagtagattt tagtgcgtaa ttatatgttg gacgagaatt     1380
tataaaatca aggagcacgc atttccttgt aatatcaggg taacgacttt ataaattaaa     1440
aaaaaaaaaa aaaaaaa                                                   1457
```

<212> Type: DNA
<211> Length: 1457
SequenceName: CcCAD1b cDNA

Sequence (SEQ ID NO: 9)
<213> OrganismName: Coffea canephora
<400> PreSequenceString:

```
ccaccaaaca ctttcttctc cacctatcat cggcgcctta attctgccaa tacacaaaac       60
tcctccattg ttttcattc catcgacttt tgtcatcatc tacttctctc tcaaccaaga      120
aaatccccaa aaaaatactg caaatgtttt agcaatataa cccagcagga gaaaagtcaa      180
cacttctgag ccctttaaa ggttacagaa acttaggagc agaggaaggg ggggagccat      240
cgcagcttgg cgctgccgtt ttcgccctgc tttcttcagc aaataaccct tgaaaaagag      300
acagaatgag cggagcggga aaggtggtgt gcgtgacagg agcatcagga tacatagctt      360
cttggttgat caagatgttg cttcatcgtg ttataccgt caaagcttca gttcgtgacc      420
tcaatgatcc aaaaaagaca gaattttga tggcactgga tggagccaag gaaagacttc      480 acttgttca tgcaaactta gtggaagagg gatcctttga tgcaatagtt gatggatgtg      540
aaggtgtttt tcatactgca tctccaatcc ttcatccagc gagtgtgacc aatccacaga      600
tagagcaatt ggatcctgca ctaaagggaa cactgaatgt gctgcgatct tgtgctagag      660
tttcatctat caaagagtg gttttaacat cttctatgag agcagtgaca tgtaatcggg      720
aactaaagga tggtgttgta gttgatgaaa gttggttgc agatccaaca tactgtgagg      780
agcgcaagtt gtggtatcca ctatcaaga ttttggcaga gaatgctgct tgggaattct      840
caaaggagca tggtatgat atggttcaa tcataccagg aatggtcatt ggtcccatct      900
tgcagcctta tcccagttta actgcaggaa tggtcctgaa cgtagtaaaa ggagctgcat      960
cgttctatac cgcgcgcatg agatggggttg atgttagaga tgttgcatat gcacatattc     1020
tagcctttga agtcccttct gccagtggaa gatattgtgt agttgaggga tttgcactgt     1080
ggactgagtt tatcaagact ctgaatgaat tgtatcctac tctccaactg tcagatgagt     1140
```

```
gttctactag tactccccta gttgagccac actacgaatt atcaaatgag aaagcaaagg    1200
gtttggggat tgagttcatt cctttcgacg tttgcctcaa ggataccatc gaaagcttca    1260
aagagaagaa cttggttaac ttctgaacaa aattcctaag cagactgaga ttggaaaata    1320
tacagtatcc aactattcat tctcttgtgt gagagtaaac tcttaaaagt atgggactgg    1380
tgaactttta ttgtagttga taattgtctc tggtactttt attgaactga tcgaacttta    1440
attgtagcaa tatgaaacca tgggagggct atgccaagga aggcttaatc caaaaaaaaa    1500
aaaaaaaaaa aaaaaaaaaa a                                              1521
```
<212> Type: DNA
<211> Length: 1521
SequenceName: CcCAD2 cDNA Sequence (SEQ ID NO: 10)
<213> OrganismName: *Coffea canephora*
<400> PreSequenceString:
```
ctttaagcag tggtaacaac gcagagtacg cgggggagtc tgccagatgg atggatactc      60
tcatatccat tctgctacta atggccccgt aaggtgatcc ttggatgcaa ggctgacagg     120
taacaaattc gctcacaaaa agagcttgga gaagaatgag tggaccagga gaggataaag     180
tggtgtgtgt gactggagct tcgggttaca tagcttcatg gctggtcaag cagctacttg     240 gccgggggtta tacagttaaa gcttctgttc gagatgccaa tgatccaaga aagacggaac     300
atttgacgtc acttgatgga gccaaggaga gactgaagtt gtttcaggcg aacttacttg     360
atgatggatc ctttgatgaa atagttcaag gatgtactgg cgttttcat accgcttctc      420 ctgttaattt ttcggttagc gatccgaaga aagaattgct agaccctgca gtaaagggaa     480
cactgaacct gcttcaatca tgtgcaaaag tttcatctat cagaagagta atcctgacat     540
cttctacggc tgcagttctg gcaaaaccag agctaaataa agattcattt gttgacgaaa     600
gttggttttc taacccatca tactgtgagg agcaaaagat gtggtatcaa ctgtcaaaaa     660
ctttagcaga ggatgctgct tggaaattct caaaggagca tggcattgac atggtttcaa     720
tcaatccagg atgggtcttt ggtcccattt tgcagccttc tatcaatcta agtgcaggat     780
tggtcctgga tgtagtaaat gggtctcaat catttcctga tgcatgtgtt ggatggattg     840
atgttagaga tgttgcctgt gcacatattc atgcctttga aatcccttct gctaatggaa     900
gatattgtgt agttgggaaa atgtgcact ggtccgagat cgtcaagatt ctgaggcaac     960 ttttcctac tcttcaactt ccaaataaag gttctcctaa tagcaccttc ggtatgggag    1020
aattcgaagt gtcaatggag aaaacaaaag gtttgggaat caatttcatt ccattggaag    1080
tgagcctgaa ggacactgtt gaaagtttca tggagaagaa ttttattact ttttaaatca    1140
agaacggttt aaatttgtaa gaatttgtgt tcctaaaaca atcataaaga ttatttgtta    1200
tagttcatgg agttgtataa ttaaaaaaat tagtcaatgt tcgtaccatc tgttgtatct    1260
attgtaatta ttgattcttg gaaaaaaaaa aaaaaaaaa aaaaaaaa                   1309
```
<212> Type: DNA
<211> Length: 1309
SequenceName: CcCAD3 cDNA Sequence (SEQ ID NO: 11)
<213> OrganismName: *Coffea canephora*
<400> PreSequenceString:
```
gctgaatgtg ctacagtctt gtgccaaagt tcaatctatc aaaagagtga ttttaacgtc      60
ttctattgca gcagttatat acaaagatga attaaaggac ggtgtcatag ttgacgaaag     120
ttggttttca gttccattat actgtgaaga gcacaagtta tggtatcaac tatcaaaaat     180
tttggcagag aatgctgctt gggatttctc aaaggagcat ggtattgaca tgattgcaat     240
taatccagga atggtcaccg gtcccttctt gcagccttct gccactttga gtgcagaagt     300
```

```
gatcttgagn cctagtaaat gtggaagata ttgcgtagtt gagagaactg caggctgctg    360
tgagcttatc aggattctga ctgaactctt cccaactctc cagttgccag ataaatattc    420
taatggcagt cccctaattc agctgaaata tgatgtatca aatgaaaaag taaaaggttt    480
gggcattgag ttcatgcctt tggaggtgag cctcaaggat actatcgaaa gcttcataga    540
gatgaaatta gttagccttt gaatcatggc attcatgtac tgtcatcaac ttgaaattgt    600
ttatatccaa gtttggaaaa cattcaattt caaacttctc attcttgttt gtacaaggta    660
cgcgattcag attatatata aagtagctaa attgtaaata aaaaaaaaaa aaaaaaa      717
<212> Type: DNA
<211> Length: 717
SequenceName: CcCAD4p partial cDNA Sequence (SEQ ID NO: 12)
<213> OrganismName: Coffea canephora
<400> PreSequenceString:
gccacacaaa aggtcgttat tccctctca attccctctc tcggccctcg tctttcccta     60
aaacaaaaaa aatttccagc acacttccac tacacaaaca cacaccaata agaaactttc    120
cctcaccctc tcggctctat ctctccattt tttcaattca cacaacacac ccacaaacaa    180
ttcaaacaca acatagcaag caacaaagga ttaaagcttg ggagttcctt caaccatttg    240
gccgagaaac tcctacttgg attgaggaaa agagacaga atgagcggag cgggaaaggt     300
ggtgtgcgtg acaggagcat caggatacat agcttcttgg ttgatcaaga tgttgcttca    360
tcgtggttat accgtcaaag cttcagttcg tgacctcaat gatccaaaaa agacagaatt    420
tttgatggca ctggatggag ccaaggaaag acttcacttg tttcatgcaa acttattgga    480
agatggatcc tttgatgcaa tagttgatgg atgtgaaggt gtttttcata ctgcatctaa    540
caatccttca tccagcgagt gtgaccaatc gaaatagagc aattgcatcc tgcccaaaag    600
gaaaaactga atgtccgtt atctagagca agagctaatt caaatcatcg ataggatttt    660
aaaatactac aaagaaaaaa tcgcgcttgt aattcgaaac taaataaagc tgttggaagt    720
gcaccaaaac tccttataaa tcaa                                          744
<212> Type: DNA
<211> Length: 744
SequenceName: CcCAD5p partial cDNA Sequence (SEQ ID NO: 13)
<213> OrganismName: Coffea canephora
<400> PreSequenceString:
aaactcacac atttacaatc aatcacagag agaatgagcg gagcagggaa ggtggttggt     60
gtgacgggag cttcagggta cgtagcttca tggctggtga agctgctgct tgagcggggt    120
tacactgtta aagcttccgt tcgtgacctc aatgatccag acaacacaga acatttgatt    180
tcacttgatg gagccaagga aaggcttcac ttgtttgttg ctgacttgat gaaagatgga    240
tcatttgatg aaatggttga tggatgtgaa ggtgttttc atactgcatc tccattcaaa    300
cctgtagtta gtgatccaga ggcagaattg ttggaccctg cggtgaaggg aactctgaat    360
gtgctacaat catgtgcaag agtttcatct gtcaaaagag tggtagtgac atcttctata    420
gcctcggttg catacaaccg agaagcgaag gatggtgttg tagttgatga agttggtttt    480
tcagagccat catactgtga agaacgcaag ctctggtatg tactttcaaa acgttggca     540 gagactgctg catggaagtt ctcaaaggag catggcattg atatgattac aattcatcca    600
tcatggatca ttggtcctca tttgcagcct tctatcaata caagtgtgca attgatcctg    660
aacctactaa atggggatga atcatttcct tacgcaa                             697
<212> Type: DNA
<211> Length: 697
SequenceName: CcCAD6p partial cDNA
```

```
Sequence (SEQ ID NO: 14)
<213> OrganismName: Coffea canephora
<400> PreSequenceString:
tttgaatttg atcgccgcca catcaaagca gttttggtgg acttgcttac tgcagcaatg    60
gacactacag ctacaactgt tgaatggata ctcgcggagc tcttgaaaaa cccccgagta   120
atgaagaaag tccagcaaga attggacgaa aaagtaggcc tacacaggat ggttgaggaa   180
tcagaattgg aaaacctgac atacttagac atggttgtaa aggaagcatt aaggctccat   240
cctgttgtac cattacttct tcctcatgca gccttggagg attgcatagt tgacggtttc   300
catataccga agattcccg agtgacgatc aatgcttgga cgatcggaag agatccaaat   360
gcatggtctg atcctgagaa gtttacacca gagagattta ttgggagcaa catagatgta   420
agaggacatg atttccagct tattcccttt ggctcaggca aagaatctg ccctggaatg   480 cagttggggc taactgtggt ccgtcttatg ttggcacgaa tggtgcattg tttcaattgg   540
gaacttccaa atgggatgct gccttcagag ctagacatga ccgaggaatt tggccttgtg   600
atgaccaggg ccaagcatct gatggctatt ccaacatatc gattgagcaa atgattaagc   660
aggtcttgag agatgcatgc tatttctata ttgcacctta tatattaagg tctactytgc   720
taagttcttg aaatgataaa tggttgtcaa gaataggtag gtattcatga cagaaccaag   780
tacttttaaa agcttcttct tttgtcactt ataaagtatg aaagatggaa tcttttttcac   840 aaaattctgt acagtttaaa taaggattac tgcatttty ttttatattc tcttataaag   900
tatgcatgtt aatttgaaaa aaaaaaaaaa aaaa                              934
<212> Type: DNA
<211> Length: 934
SequenceName: CcF5Hp partial cDNA Sequence (SEQ ID NO: 15)
<213> OrganismName: Coffea canephora
<400> PreSequenceString:
MAEEEACLFA MSLASASVLP MVLKSAIELD LLELIAKAGP GAYVSPSELA AQLPTHNPEA    60

PIMLDRILRL LATYSVLDCK LNNLADGGVE RLYGLAPVCK FLTKNADGVS MAPLLLMNQD   120

KVLMESWYHL KDAVLDGGIP FNKAYGMTAF EYHGTDPRFN KVFNQGMSNH STITMKKILE   180

VYRGFEGLKT VVDVGGGTGA TLNMIISKYP TIKGINFELP HVVEDAPSHS GVEHVGGDMF   240

VSVPKGDAIF MKWICHDWSD DHCRKLLKNC YQALPDNGKV ILAECVLPEA PDTSLATQNV   300

VHVDVVMLAH NPGGKERTEK EFEALAKGAG FKEFRKVCSA VNTWIMELCK              350
<212> Type: PRT
<211> Length: 350
SequenceName: CcCOMT1 protein Sequence (SEQ ID NO: 16)
<213> OrganismName: Coffea canephora
<400> PreSequenceString:
YELGNSLLEG GIPFNRVHGM HAFDYPSRDP RYNELFNKGM VGPTAITMKK LLQQYKGFEH    60

LQTLVDVGGG LGITLHKIIS KYPSIRGINF DLPHVIENAP SYLGVEHIGG DMFESVPGGD   120

AIFMKMILHD WSDDHCLKLL KNCFKALPDH GKVIVVDLVL FVKPDTSAFV KGIFQTDALM   180

MTQNPGGKER SESDVRALAI RAGFKDIKLE CCVGSLGVLE LYK                     223
<212> Type: PRT
<211> Length: 223
SequenceName: CcCOMT2p partial protein Sequence (SEQ ID NO: 17)
<213> OrganismName: Coffea canephora
<400> PreSequenceString:
MDSSSRATDN VVVEAGLDEQ EEQHFSYAMQ LVTSVSLPMV LLAAIRLDVL EVIAQAGPGA    60

QLSPWDIAAQ VGPKNPDAAA MLDRMLQLLA SYSVLTCSVA EAD                     103
<212> Type: PRT
<211> Length: 103
```

-continued

SequenceName: CcCOMT3p partial protein

Sequence (SEQ ID NO: 18)
<213> OrganismName: *Coffea canephora*
<400> PreSequenceString:

| | | | | | |
|---|---|---|---|---|---|
| KFFVQNKTKG | GGSLGSVLGL | LQDKVFIDSW | YQLEDAVRKG | GDPFHRAHGT | HAFEFLGSDP | 60 |
| RFNEVFNKAM | IHHTAIVINR | MLERYKGFEH | LKTLVDVGGG | LGMNLNIITT | KYPSLKGINF | 120 |
| DLPHVIQHAP | AYPGVEHVGG | DMFESVPQGD | AIFMKWILHD | WDDGHCLKLL | KNCYKALPDN | 180 |
| GKVIAVDAIL | PVVPDDSARD | KATCQADLVV | VTQYRGGIER | YETEFLALAT | AAGFKGISVK | 240 |
| CFVCNLWVME | FYK | | | | | 253 |

<212> Type: PRT
<211> Length: 253
SequenceName: CcCOMT4p partial protein

Sequence (SEQ ID NO: 19)
<213> OrganismName: *Coffea canephora*
<400> PreSequenceString:

| | | | | | |
|---|---|---|---|---|---|
| MAAWEAEKAR | TVCVTGAGGY | LGSWLVKLLL | SRHYTVHATL | RNPEDEKYVH | LKKLDKAAEN | 60 |
| LKLFKADLLD | YNSISAAIRG | CDGVFHVASP | VPSGSVPNPE | VELVEPAVKG | TLNVLKACSE | 120 |
| ANVKRVVAVS | SVAAVVVSPN | RHKGEIIDET | CWSDGEYCKT | TNNWYCYSKT | VAESEALQYA | 180 |
| KETGLDVLTV | CPSFVLGPML | QHDVNASSLA | LIKLLKEGYE | EIENKFRDMV | DVRDVAEALL | 240 |
| LVYGRPEAEG | RYICSSHLTT | TKDTVEILRK | NYPNYKYPKR | FIEVKDDQGR | GNVSSEKLQR | 300 |
| LGWRYRPVEE | TLVDSVESYQ | QAGILD | | | | 326 |

<212> Type: PRT
<211> Length: 326
SequenceName: CcCCR1 protein

Sequence (SEQ ID NO: 20)
<213> OrganismName: *Coffea canephora*
<400> PreSequenceString:

| | | | | | |
|---|---|---|---|---|---|
| MPSVSGQVVC | VTGAGGYIAS | WIVKLLLEKG | YTVRGTVRNP | DDAKNGHLRE | LEGAKERLTL | 60 |
| CRADLLDYQS | LREAIKGCDG | VFHTASPVTD | DPEQMVEPAV | IGTKNVINAA | AEAKVRRMVF | 120 |
| TSSIGAVYMD | PNREPEKVVD | ESCWSDLEFC | KNTKNWYCYG | KAVAEKAAWD | EAKEKGVDLV | 180 |
| VINPVLVLGP | LLQPTVNASI | LKILKYLTGS | AKTYANSVQA | YVHVKDVALA | HVLIYETPSA | 240 |
| SGRYLCAESV | LHRGEVVEIL | AKLFPEYPIP | TKCSDETRPR | AKAYKFTNQK | LKDLGFEFTP | 300 |
| VKQCLYETVK | SLQEKGQIPL | PTQNDKPIKI | HY | | | 332 |

<212> Type: PRT
<211> Length: 332
SequenceName: CcCCR2 protein

Sequence (SEQ ID NO: 21)
<213> OrganismName: *Coffea canephora*
<400> PreSequenceString:

| | | | | | |
|---|---|---|---|---|---|
| QTKLWYVLSK | TLAEDAAWKF | VKEKGLDMVT | INPAMVIGPL | LQPTLNTSAA | AILNLINGAE | 60 |
| TFPNSSMGWV | DVKDVANAYT | IAFENPSASG | RYCLVERVVH | YSEVVKILRE | IYPSSKLPEK | 120 |
| CADDKPFVPT | YQVSKEKAKS | LGLEFIPLEQ | SIKETVESLK | EKNFLDSSAA | L | 171 |

<212> Type: PRT
<211> Length: 171
SequenceName: CcCAD1ap partial protein

Sequence (SEQ ID NO: 22)
<213> OrganismName: *Coffea canephora*
<400> PreSequenceString:

| | | | | | |
|---|---|---|---|---|---|
| MKTVCVTGAS | GYIASWLVKF | LLQRGYTVKA | SVRDLNDPKK | VEHLLALDGA | KERLQLFKAN | 60 |
| LLEEGSFDAA | IDGCDGVFHM | ASPFYHTVTD | PQAELIDPAL | KGTLSVLGSC | AKSPSVKRVV | 120 |
| LTSSIAAVAF | NGKPRTPDVV | VDETWWSLPE | FCKQMKLWYV | LSKTLAEDAA | WKFVKEKGLD | 180 |
| MVTINPAMVI | GPLLQPTLNT | SAAAILNLIN | GAETFPNSSM | GWVDVKDVAN | AHILAFENPS | 240 |
| ASGRYCLVER | VVHYSEVVNI | LREIYPSSKL | PEKCADDKPF | VPTYQVSKEK | AKSLGLEFIP | 300 |

```
VEQSIKETVE SLKEKNFLNS SAAL                                       324
<212> Type: PRT
<211> Length: 324
SequenceName: CcCAD1b protein Sequence (SEQ ID NO: 23)
<213> OrganismName: Coffea canephora
<400> PreSequenceString:
MSGAGKVVCV TGASGYIASW LIKMLLHRGY TVKASVRDLN DPKKTEFLMA LDGAKERLHL  60

FHANLVEEGS FDAIVDGCEG VFHTASPILH PASVTNPQIE QLDPALKGTL NVLRSCARVS 120

SIKRVVLTSS MRAVTCNREL KDGVVVDESW FADPTYCEER KLWYPLSKIL AENAAWEFSK 180

EHGIDMVAII PGMVIGPILQ PYPSLTAGMV LNVVKGAASF YTARMRWVDV RDVAYAHILA 240

FEVPSASGRY CVVEGFALWT EFIKTLNELY PTLQLSDECS TSTPLVEPHY ELSNEKAKGL 300

GIEFIPFDVC LKDTIESFKE KNLVNF                                    326
<212> Type: PRT
<211> Length: 326
SequenceName: CcCAD2 protein Sequence (SEQ ID NO: 24)
<213> OrganismName: Coffea canephora
<400> PreSequenceString:
MSGPGEDKVV CVTGASGYIA SWLVKQLLGR GYTVKASVRD ANDPRKTEHL TSLDGAKERL  60

KLFQANLLDD GSFDEIVQGC TGVFHTASPV NFSVSDPKKE LLDPAVKGTL NLLQSCAKVS 120

SIRRVILTSS TAAVLAKPEL NKDSFVDESW FSNPSYCEEQ KMWYQLSKTL AEDAAWKFSK 180

EHGIDMVSIN PGWVFGPILQ PSINLSAGLV LDVVNGSQSF PDACVGWIDV RDVACAHIHA 240

FEIPSANGRY CVVGKNVHWS EIVKILRQLF PTLQLPNKGS PNSTFGMGEF EVSMEKTKGL 300

GINFIPLEVS LKDTVESFME KNFITF                                    326
<212> Type: PRT
<211> Length: 326
SequenceName: CcCAD3 protein Sequence (SEQ ID NO: 25)
<213> OrganismName: Coffea canephora
<400> PreSequenceString:
LNVLQSCAKV QSIKRVILTS SIAAVIYKDE LKDGVIVDES WFSVPLYCEE HKLWYQLSKI  60

LAENAAWDFS KEHGIDMIAI NPGMVTGPFL QPSATLSAEV ILPSKCGRYC VVERTAGCCE 120

LIRILTELFP TLQLPDKYSN GSPLIQLKYD VSNEKVKGLG IEFMPLEVSL KDTIESFIEM 180

KLV                                                             183
<212> Type: PRT
<211> Length: 183
SequenceName: CcCAD4p partial protein Sequence (SEQ ID NO: 26)
<213> OrganismName: Coffea canephora
<400> PreSequenceString:
MSGAGKVVCV TGASGYIASW LIKMLLHRGY TVKASVRDLN DPKKTEFLMA LDGAKERLHL  60

FHANLLEDGS FDAIVDGCEG VFHTAS                                     86
<212> Type: PRT
<211> Length: 86
SequenceName: CcCAD5p partial protein Sequence (SEQ ID NO: 27)
<213> OrganismName: Coffea canephora
<400> PreSequenceString:
MSGAGKVVGV TGASGYVASW LVKLLLERGY TVKASVRDLN DPDNTEHLIS LDGAKERLHL  60

FVADLMKDGS FDEMVDGCEG VFHTASPFKP VVSDPEAELL DPAVKGTLNV LQSCARVSSV 120

KRVVVTSSIA SVAYNREAKD GVVVDESWFS EPSYCEERKL WYVLSKTLAE TAAWKFSKEH 180

GIDMITIHPS WIIGPHLQPS INTSVQLILN LLNGDESFPY A                   221
<212> Type: PRT
<211> Length: 221
SequenceName: CcCAD6p partial protein
```

-continued

Sequence (SEQ ID NO: 28)
<213> OrganismName: Coffea canephora
<400> PreSequenceString:

```
FEFDRRHIKA VLVDLLTAAM DTTATTVEWI LAELLKNPRV MKKVQQELDE KVGLHRMVEE    60

SELENLTYLD MVVKEALRLH PVVPLLLPHA ALEDCIVDGF HIPKDSRVTI NAWTIGRDPN   120

AWSDPEKFTP ERFIGSNIDV RGHDFQLIPF GSGRRICPGM QLGLTVVRLM LARMVHCFNW   180

ELPNGMLPSE LDMTEEFGLV MTRAKHLMAI PTYRLSK                           217
```
<212> Type: PRT
<211> Length: 217
SequenceName: CcF5Hp partial protein The present invention is not limited to the embodiments described and exemplified above, but is capable of variation and modification within the scope of the appended claims.

---

What is claimed is:

1. A nucleic acid molecule isolated from coffee (*Coffea* spp.), having a coding sequence that encodes a caffeic acid O-methyltransferase enzyme, wherein the caffeic acid O-methyltransferase enzyme comprises an amino acid sequence at least 90% identical to one or more of SEQ ID NOs: 16-18.

2. The nucleic acid molecule of claim 1, wherein the caffeic acid O-methyltransferase enzyme comprises an amino acid sequence greater than 95% identical to SEQ ID NO:16.

3. The nucleic acid molecule of claim 1, wherein the caffeic acid O-methyltransferase enzyme comprises an amino acid sequence greater than 95% identical to SEQ ID NO:17.

4. The nucleic acid molecule of claim 1, wherein the caffeic acid O-methyltransferase enzyme comprises an amino acid sequence greater than 95% identical to SEQ ID NO:18.

5. The nucleic acid molecule of claim 1, wherein the coding sequence is an open reading frame of a gene, or a mRNA, or a cDNA.

6. The coding sequence of the nucleic acid molecule of claim 1, contained within a vector.

7. The vector of claim 6, which is an expression vector selected from the group of vectors consisting of plasmid, phagemid, cosmid, baculovirus, bacmid, bacterial, yeast and viral vectors.

8. The vector of claim 6, wherein the coding sequence of the nucleic acid molecule is operably linked to a constitutive promoter, or an inducible promoter, or a tissue-specific promoter.

9. The vector of claim 8, wherein the tissue specific promoter is a seed specific promoter.

10. The vector of claim 9, wherein the seed specific promoter is a coffee seed specific promoter.

11. A host cell transformed with the vector of claim 6.

12. The host cell of claim 11, which is a plant cell selected from the group of plants consisting of coffee, tobacco, *Arabidopsis*, maize, wheat, rice, soybean, barley, rye, oats, sorghum, alfalfa, clover, canola, safflower, sunflower, peanut, cacao, tomatillo, potato, pepper, eggplant, sugar beet, carrot, cucumber, lettuce, pea, aster, begonia, chrysanthemum, delphinium, petunia, zinnia, and turfgrasses.

13. A fertile plant produced from the plant cell of claim 12.

14. A method of modulating flavor or aroma of coffee beans, comprising modulating production or activity of one or more caffeic acid O-methyltransferase enzymes within coffee seeds, wherein the caffeic acid O-methyltransferase enzyme comprises an amino acid sequence at least 90% identical to one or more of SEQ ID NOs: 16-18.

15. The method of claim 14, comprising increasing production or activity of the one or more caffeic acid O-methyltransferase enzymes.

16. The method of claim 14, comprising decreasing production or activity of the one or more caffeic acid O-methyltransferase enzymes.

* * * * *